US007267978B1

(12) United States Patent
Carey et al.

(10) Patent No.: US 7,267,978 B1
(45) Date of Patent: Sep. 11, 2007

(54) CHIMERIC TRANSCRIPTIONAL REGULATORY ELEMENT COMPOSITIONS AND METHODS FOR INCREASING PROSTATE-TARGETED GENE EXPRESSION

(75) Inventors: Michael F. Carey, Sherman Oaks, CA (US); Arie S. Belldegrun, Los Angeles, CA (US); Lilly Wu, Northridge, CA (US)

(73) Assignee: The Regents of the University of California, Oakland, CA (US)

( * ) Notice: Subject to any disclaimer, the term of this patent is extended or adjusted under 35 U.S.C. 154(b) by 590 days.

(21) Appl. No.: 10/110,681

(22) PCT Filed: Oct. 13, 2000

(86) PCT No.: PCT/US00/28444

§ 371 (c)(1),
(2), (4) Date: Apr. 15, 2002

(87) PCT Pub. No.: WO01/27256

PCT Pub. Date: Apr. 19, 2001

Related U.S. Application Data

(60) Provisional application No. 60/159,730, filed on Oct. 15, 1999, provisional application No. 60/159,691, filed on Oct. 14, 1999.

(51) Int. Cl.
*C12N 15/00* (2006.01)
(52) U.S. Cl. .................................. 435/320.1
(58) Field of Classification Search ............. 435/320.1; 424/93.2
See application file for complete search history.

(56) References Cited

U.S. PATENT DOCUMENTS

| | | | |
|---|---|---|---|
| 5,698,443 | A | 12/1997 | Henderson et al. |
| 5,830,686 | A | 11/1998 | Henderson |
| 5,871,726 | A | 2/1999 | Henderson et al. |
| 6,051,417 | A | 4/2000 | Henderson et al. |
| 6,057,299 | A | 5/2000 | Henderson |
| 6,110,702 | A * | 8/2000 | Pang et al. ................. 435/69.1 |
| 6,120,994 | A * | 9/2000 | Tam .............................. 435/6 |

FOREIGN PATENT DOCUMENTS

| | | |
|---|---|---|
| WO | WO95/19434 A1 | 7/1995 |
| WO | WO96/14875 | 5/1996 |
| WO | WO97/01358 A1 | 1/1997 |

OTHER PUBLICATIONS

Cleutjens et al., Molecular Endocrinology 11:148-161, 1997.*
Pang, Shen, et al., *Identification of a Positive Regulatory Element Responsible for Tissue-specific Expression of Prostate-specific Antigen*, Cancer Research, vol. 57, pp. 495-499, Feb. 1, 1997.

Riegman, P.H.J., et al., *The Promoter of the Prostate-Specific Antigen Gene Contains a Functional Androgen Responsive Element*, Molecular Endocrinology, vol. 5, No. 12, pp. 1921-1930 (1991).
Zhang, S., et al. *Defining a Functional Androgen Responsive Element in the 5' Far Upstream Flanking Region of the Prostate-Specific Antigen Gene*, Biochemical and Biophysical Research Communications, No. 231, pp. 784-788 (1997).
Huang, Weibiao, et al., *Cooperative Assembly of Androgen Receptor into a Nucleoprotein Complex that Regulates the Prostate-specific Antigen Enhancer*, Journal of Biological Chemistry, vol. 274, No. 36, pp. 25756-25768 (1999).
Bacchetti, S. et al., "Transfer of the gene for thymidine kinase to thymidine kinase-deficient human cells by purified herpes simplex viral DNA," *PNAS USA*, 74:1590-1594 (1977).
Carey, M., "The Enhanceosome and Transcriptional Synergy," *Cell*, 92:5-8 (1998).
Cleutjens, K. et al., "Two Androgen Response Regions Cooperate in Steroid Hormone Regulated Activity of the Prostate-specific Antigen Promoter," *J. Biol. Chem.*, 271:6379-6388 (1996).
Cleutjens, K. et al., "A 6-kb Promoter Fragment Mimics in Transgenic Mice the Prostate-Specific and Androgen-Regulated Expression of the Endogenous Prostate-Specific Antigen Gene in Humans," *Mol. Endocrinol.*, 11:1256-1265 (1997).
Dannull, J. et al., "Development of gene therapy for prostate cancer using a novel promoter of prostate-specific antigen," *British J. of Urol.*, 79:97-103 (1997).
El-Shirbiny, A.M., "Prostate Specific Antigen," *Adv. Clin. Chem.*, 31;99-133 (1994).
Gotoh, A. et al., "Development of Prostate-Specific Antigen Promoter-Based Gene Therapy for Androgen-Independent Human Prostate Cancer," *J. of Urol.*, 160:220-229 (1998).
Herman, J.R. et al., "In Situ Gene Therapy for Adenocarcinoma of the Prostate: A Phase I Clinical Trial," *Human Gene Therapy*, 10:1239-1249 (1999).
Kasper, S. et al., "Cooperative Binding of Androgen Receptors to Two DNA Sequences is Required for Androgen Induction of the Probasin Gene," *J. of Biol. Chem.*, 269:31763-31769 (1994).

(Continued)

*Primary Examiner*—Brian Whiteman
(74) *Attorney, Agent, or Firm*—Townsend and Townsend and Crew LLP

(57) ABSTRACT

Disclosed are compositions and methods for achieving successful treatment of disorders of the human prostate. In preferred embodiments, methods and compositions are provided that improve the specificity and safety of gene delivery vectors, and improve the prostate-specificity and activity of genetic constructs targeted for prostate-specific expression. Also disclosed are methods utilizing a variety of therapeutic genes, including those encoding tumor-specific therapeutics, e.g., TRAIL, tumor suppressors, cytotoxins, and the like, for the treatment of proliferative disorders of the prostate, and in particular, prostatic hyperplasia, prostate cancer and prostatic tumors. In preferred embodiments genetic constructs are disclosed comprising one or more prostate-specific chimeric enhancer elements in combination with one or more wildtype core enhancer elements and a prostate-specific proximal promoter that increase expression of selected heterologous genes operably positioned under their control.

53 Claims, 18 Drawing Sheets

OTHER PUBLICATIONS

Kay, A.B. et al., "Messenger RNA Expression of the Cytokine Gene Cluster, Interleukin 3 (IL-3), IL-4, IL5, and Granulocyte/Macrophage Colony-stimulating Factor, in Allergen-induced Late-hase Cutaneous Reactions in Atopic Subjects," *J. Exp. Med.*, 173:775-778 (1991).

Li, Y. et al., "Proinflammatory Cytokines Tumor Necrosis Factor-α And IL-6, But Not IL-1, Down-Regulate The Osteocalcin Gene Promoter," *J. of Immun.*, 148:788-794 (1992).

Lu, Y. et al., "Delivery of adenoviral vectors to the prostate for gene therapy," *Cancer Gene Therapy*, 6:64-72 (1999).

Pang, S. et al., "Prostate Tissue Specificity of the Prostate-Specific Antigen Promoter Isolated from a Patient with Prostate Cancer," *Human Gene Therapy*, 6:1417-1426 (1995).

Scheller, A. et al., "Multiple Receptor Domains Interact to Permit, or Restrict, Androgen-specific Gene Activation," *J. of Biol. Chem.*, 273:24216-24222 (1998).

Schuur, E.R. et al., "Prostate-specific Antigen Expression Is Regulated by an Upstream Enhancer," *J. of Biol. Chem.*, 271:7043-7051 (1996).

Steiner, M.S. et al., "In vivo expression of prostate-specific adenoviral vectors in a canine model," *Cancer Gene Therapy*, 6:456-464 (1999).

Vile, R.G. et al., "Systemic Gene Therapy of Murine Melanoma Using Tissue Specific Expression of the HSVtk Gene Involves an Immune Component," *Cancer Research*, 54:6228-6234 (1994).

Wei, C. et al., "Tissue-specific expression of the human prostate-specific antigen gene in transgenic mice: Implications for tolerance and immunotherapy," *Proc. Natl. Acad. Sci. USA*, 94:6369-6374 (1997).

Zhang, J. et al., "Identification of two novel cis-elements in the promoter of the prostate-specific antigen gene that are required to enhance androgen receptor-mediated transactivation," *Nucleic Acids Research*, 25:3143-3150 (1997).

* cited by examiner

FIG. 1A

5' – CCATGGTAACCGGGGGATCCCTCTAGAACTAGTGGATCTGC [AGAACAGCAAGTGCT] ——ARE₁
(SEQ ID NO:1, REVERSE)

AGCTGATCAGCT [AGCACTTGCTGTGTTCT] GCAAGATCAGCT [AGCACTTGCTGTGTTCT] ——ARE₂ ——ARE₃
(SEQ ID NO:1, FORWARD) (SEQ ID NO:1, FORWARD)

GCAAGCTCAGCT [AGCACTTGCTGTGTTCT] GCAAGATCCCCCGGGCCCATGG – 3' ——ARE₄
(SEQ ID NO:1, FORWARD)

FIG. 1C

CHIMERIC TRANSCRIPTIONAL REGULATORY ELEMENT COMPOSITIONS AND METHODS FOR INCREASING PROSTATE-TARGETED GENE EXPRESSION

This application is a National Stage of International Application No. PCT/US00/28444, filed Oct. 13, 2000 which claims the benefit under 35 U.S.C §119(e) of U.S. Provisional Application No. 60/159,691, filed Oct. 14, 1999 and also of U.S. Provisional Application No. 60/159,730, filed Oct. 15, 1999, the entire contents of each of which is incorporated herein by reference in its entirety without disclaimer.

The United States government has certain rights in the present invention pursuant to Grant No. PC970515 from the Department of the Army.

1.0 BACKGROUND OF THE INVENTION

1.1 Field of the Invention

The present invention relates generally to the fields of molecular biology and genetics. More particularly, it concerns novel chimeric transcriptional regulatory elements that improve the transcriptional activity of naturally occurring transcriptional regulatory elements, and methods for their use in gene therapy and in particular, prostate-targeted gene expression.

1.2 Description of the Related Art

The prostate specific antigen (PSA) enhancer and promoter can confer exquisite prostate-specific expression of linked reporter gene, with strong androgen stimulation in in vitro transfection of PSA producing prostate cells. Detailed genetic and biochemical analysis of the PSA enhancer core region, −4326 to −3935 with respect to transcriptional start site at +1, clearly established the functional importance of AR binding in this region. Moreover, the cooperative and synergistic binding of AR to the multiple AREs contribute greatly to the androgen responsive transcriptional activity of the PSA enhancer region.

However, when inserted into viral vectors capable of efficient in vivo gene delivery, the native PSA enhancer and promoter activity is low (Pang et al., 1997).

1.3 Deficiencies in the Prior Art

A major obstacle to contemporary cancer treatment using gene therapy is the problem of selectivity; that is, the ability to inhibit the multiplication of tumor cells, while leaving unaffected the function of normal cells. The therapeutic ratio (ratio of tumor cell killing to normal cell killing) of traditional tumor chemotherapy is only 1.5:1, clear evidence that more effective methods for the treatment and prophylaxis of prostatic hyperplasias and neoplasias are needed.

Thus, there remains a need for the development of improved expression vectors, and genetic constructs that can be used to effect high-level expression of selected therapeutic genes in a tissue-specific manner in the mammalian prostate. Also desirable are gene therapy vectors, and in particular viral and liposomal-mediated vectors for administering such therapeutic constructs to an animal in need thereof. The need also exists for effective treatment regimens for prostate cancer, and in particular, prostate tumors that circumvent the toxic side effects of existing therapies and provide more specific gene expression of the therapeutic constructs directly in the cells of the affected prostate. Tissue-specific enhancers and promoters that are active in prostate cells, and particularly in neoplastic or hyperplastic prostate cells, would represent a significant advance for those of skill in the oncologic arts, and would facilitate the creation of genetic expression constructs suitable for therapeutic ablation of prostate tissue, especially neoplastic prostate epithelium.

2.0 SUMMARY OF THE INVENTION

The present invention overcomes one or more of these and other shortcomings in the art by providing improved methods for the specific transcription of genes in prostate cells and tissues. Genetic constructs are provided that facilitate enhanced tissue-specific expression of heterologous therapeutic genes in mammalian prostate cells. The genetic constructs provided by the present invention facilitate preferential enhancement of transcription in cells having transcription factors that recognize the enhancer element sequences provided by these constructs.

The present invention provides transcriptional regulatory elements, such as enhancers and promoters, which facilitate elevated transcription of cis-linked sequences in prostate cells in a tissue-specific manner. Such elements, when operably positioned on genetic constructs that comprise one or more heterologous therapeutic genes, are expressed preferentially in prostate cells but substantially not expressed in other cell types.

To overcome the limitations that a variety of genetic constructs (including the aforementioned native PSA enhancer and promoter constructs) have placed on the development of viral vectors capable of efficient in vivo gene delivery, the present invention provides improved, second-generation genetic constructs that comprise a prostate-specific promoter (e.g., the PSA promoter) and one or more artificial regulatory elements (composed e.g. of tandem copies of naturally-occurring or synthetic ARE elements), and that have greatly increased transcriptional activity of operatively linked heterologous polynucleotide sequences. Exemplary constructs of the invention are schematically depicted in FIG. 1A and FIG. 1B. One category of such artificial regulatory elements includes enhancer elements that are composed of a plurality of native or artificial ARE elements linked in tandem. An exemplary such artificial enhancer comprises the ARE4 enhancer (SEQ ID NO:5). This enhancer comprises 4 tandem copies of the ARE element shown in SEQ ID NO:1. This element displayed >100-fold androgen inducible activity in transfection assays (FIG. 1C).

In one embodiment, the invention provides polynucleotides that comprise at least a first transcriptional regulatory element that activates transcription of cis-linked sequences in prostate cells such as neoplastic or hyperplastic prostate cells, and a first prostate-specific promoter sequence, operably linked to at least a first sequence region (e.g., a cDNA sequence, a genomic fragment, a minigene, or an antisense oligonucleotide) to form a transcription unit. This transcription unit generally comprises one or more therapeutic nucleic acid segments operably linked to the prostate-specific promoter and operably positioned relative to one or more prostate-specific enhancer elements as described herein. Such enhancer elements may be comprised of one or more copies of a native enhancer (for example, the native PSA core enhancer depicted in FIG. 1A), or alternatively, may be comprised of one or more copies of an artificial enhancer element such as the ARE4 element depicted in FIG. 1C and shown in SEQ ID NO:5. Preferably, the transcriptional units and genetic constructs of the present invention comprise one or more native enhancer elements in combination with one or more artificial enhancer elements. These chimeric enhancers will preferably comprise at least one native PSA core enhancer operably positioned in relation to one or more artificial enhancer sequences such as the ARE4 element of SEQ ID NO:5, or operably positioned in relation to an artificial enhancer that is comprised of at least 2 AREs selected from the group consisting of SEQ ID NO:1, SEQ ID NO:2, SEQ ID NO:3, and SEQ ID NO:4. In an illustrative embodiment, the transcriptional unit will preferably comprise 1 copy of the PSA core enhancer and one copy of the ARE4 artificial enhancer. In a related embodiment, the transcriptional unit will preferably comprise 2 copies of the PSA core enhancer and one copy of the ARE4 artificial enhancer. Likewise, the transcriptional unit may preferably comprise 1 copy of the PSA core enhancer and two or more copies of the ARE4 sequence.

Turning to FIG. 1B, the schematic is shown for various embodiments of the artificial enhancer sequences that may be employed in the practice of the invention. For example, when four copies of the AREI element are present in tandem, the motif for the element may be denoted:

$N_{x1}$AGAACAGCAAGTGCT$N_{x2}$AGAACAGCAAGTGCT
$N_{x2}$AGAACAGCAAGTGCT$N_{x2}$AGAACAGCAAGTGCT
$N_{x3}$ (SEQ ID NO:65), where N=C, A, T, or G, and $X_1$ is from 1 to about 39; $X_2$ is from 1 to about 20; and $X_3$ is from 1 to about 39.

Likewise, when three copies of the AREI element are present in tandem, the motif for the element may be denoted:

$N_{x1}$AGAACAGCAAGTGCT$N_{x2}$AGAACAGCAAGTGCT
$N_{x2}$AGAACAGCAAGTGCT$N_{x3}$ (SEQ ID NO:66), where N=C, A, T, or G, and $X_1$ is from 1 to about 39; $X_2$ is from 1 to about 20; and $X_3$ is from 1 to about 39.

Or, when five copies of the AREI element are present in tandem, the motif for the element may be denoted:

$N_{x1}$AGAACAGCAAGTGCT$N_{x2}$AGAACAGCAAGTGCT
$N_{x2}$AGAACAGCAAGTGCT$N_{x2}$AGAACAGCAAGTGCT
$N_{x2}$AGAACAGCAAGTGCT$N_{x3}$ (SEQ ID NO:67), where N=C, A, T, or G, and $X_1$ is from 1 to about 39; $X_2$ is from 1 to about 20; and $X_3$ is from 1 to about 39.

The operably linked therapeutic nucleic acid segment may encode one or more beneficial polypeptide products that interfere with, or eliminate the hyperproliferation of prostate cells. Alternatively, the nucleic acid segment may encode one or more antisense oligonucleotides that specifically bind to one or more mRNA sequences produced by a hyperproliferative prostate cell, and thereby reduce or decrease the level of the polypeptide encoded by such an mRNA that causes, or contributes to, the hyperproliferation of such cells. Alternatively, the nucleic acid segment may encode one or more catalytic RNA molecules (ribozymes) that specifically cleave one or more mRNA sequences produced by a hyperproliferative prostate cell, and thereby reduce or decrease the level of the polypeptide encoded by such an mRNA that causes, or contributes to, the hyperproliferation of such cells.

In the case of heterologous polypeptides, the nucleic acid segment will preferably encode an anti-cancer, cytotoxic, or cytostatic polypeptide that will decrease, prevent, or reduce the rate, size, or clinical significance of the cell into which the polypeptide is introduced. When expressed in a tissue-specific manner, in a targeted prostate cell or tissue, these constructs would result in the death or ablation of such prostate cells or prostatic tissue. Delivery of such polynucleotides to neoplastic or hyperplastic prostate cells, including those prostate cancer cells that have metastisized to other areas of the body, results in specific ablation of undesired prostate cells for therapy or prophylaxis of benign prostatic hypertrophy, prostate neoplasia, metastatic prostate tumors, and the like.

In one embodiment, the invention provides a method for treating or preventing benign prostatic hypertrophy. The method generally comprises providing to a mammal suspected of having, or at risk for developing, BPH, an effective amount of a genetic construct that comprises at least a first therapeutic heterologous gene, such as a cytotoxic gene, operably linked to at least a first prostate-specific transcriptional regulatory element as described herein, wherein the expression of the therapeutic heterologous gene is preferentially active in neoplastic or hyperplastic prostate cells, but not in other non-prostate cells of the mammal, and further wherein the expression of such a heterologous nucleic acid segment is sufficient to treat or prevent the BPH in the affected or at risk mammal.

Alternatively, the method may comprise providing to the mammal, an effective amount of a genetic construct in which the heterologous gene does not encode a cytotoxic polypeptide, but instead, encodes one or more antisense oligonucleotide sequences, transcription factors, catalytic RNA molecules (ribozymes), telomerase modulator, ribosome modulator, which, when expressed in hyperproliferative prostate cells, reduce, eliminate, or ameliorate the symptoms of benign prostatic hypertrophy in the affected, or at risk, individual.

In another embodiment, the invention provides a method for treating or preventing prostatic neoplasia. The method generally comprises providing to a mammal suspected of having, or at risk for developing prostatic neoplasia, an effective amount of a genetic construct that comprises at least a first therapeutic heterologous gene, such as a cytotoxic gene, operably linked to at least a first prostate-specific transcriptional regulatory element as described herein, wherein the expression of the therapeutic heterologous gene is preferentially active in neoplastic or hyperplastic prostate cells, but not in other non-prostate cells of the mammal, and further wherein the expression of such a heterologous nucleic acid segment is sufficient to treat or prevent the prostatic neoplasia.

Alternatively, the method for treating or preventing prostatic neoplasia may comprise providing to the mammal, an effective amount of a genetic construct in which the heterologous gene does not encode a cytotoxic polypeptide, but instead, encodes one or more antisense oligonucleotide sequences, transcription factors, catalytic RNA molecules (ribozymes), telomerase modulator, ribosome modulator, which, when expressed in hyperproliferative prostate cells, reduce, eliminate, or ameliorate the symptoms of prostatic neoplasia in the affected, or at risk, individual.

Likewise, in another embodiment, the invention provides a method for reducing or preventing hyperproliferation of a prostate cell. The method generally comprises providing to such a prostate cell, an effective amount of a genetic construct that comprises at least a first therapeutic heterologous gene, such as a cytotoxic gene, operably linked to at least a first prostate-specific transcriptional regulatory element as described herein, wherein the expression of the therapeutic heterologous gene is preferentially activated or increased in the prostate cell, and further wherein the expression of such a heterologous nucleic acid segment is sufficient to reduce or prevent the hyperproliferation of the prostate cell.

Alternatively, this method for reducing or preventing hyperproliferation of a prostate cell may comprise providing to the cell, an effective amount of a genetic construct in which the heterologous gene does not encode a cytotoxic polypeptide, but instead, encodes one or more antisense oligonucleotide sequences, transcription factors, catalytic RNA molecules (ribozymes), telomerase modulator, ribosome modulator, which, when expressed in hyperproliferative prostate cells, reduce or prevent the hyperproliferation of such a prostate cell.

The invention provides methods for treating prostate hypertrophy, hyperproliferative disorders, and prostate neoplasia that generally involve administration of one or more of the prostate-specific genetic constructs described herein using one or more of the standard methods known to those of skill in the art for the administration of genetic constructs to animal cells. Means for the administration of such constructs, either in the form of naked DNA, lipid-DNA complexes, polycation-condensed polynucleotides, or as viral-vectored nucleic acid constructs or by ligand-mediated mechanisms are described in the Illustrative Embodiments hereinbelow. Alternatively, ex situ methods may be employed, including the transfection or transformation of hypertrophic or neoplastic prostate cells explanted from the animal body with one or more of the disclosed polynucleotide constructs, which is then followed by reintroduction of the cells into the animal (typically at the site of original explant) to elicit an immune response in the animal that is directed against the transformed prostate tumor cells themselves.

In related embodiments, the invention further provides methods and compositions for the creation of transgenic non-human animals that comprise one or more of the therapeutic prostate-specific genetic constructs disclosed herein. Such transgenic animals express the heterologous nucleic acid sequence operably positioned under the control of the regulatory elements present in the construct preferentially only in prostate cells. A variety of nucleic acid segments can be delivered to such transgenic animals, including, for example, structural genes encoding polypeptides such as activated oncogene or T antigens, which produce transgenic animals having an increased propensity for developing prostate neoplasia. Such non-human transgenic animals provide the skilled artisan with disease model systems to facilitate both the study of hyperproliferative disorders of the prostate, including BPH and prostatic carcinoma, and the screening of anti-cancer therapeutics.

Examples of such heterologous genes for use in the above-described methods include those nucleic acid sequences that encode a lymphokine that activates an anti-tumor immune response (e.g., increased NK activity) in the transformed cells expressing the genetic construct. Exemplary lymphokines include but are not limited to: IL-1, IL-2, IL-12, GM-CSF, IFNα, IFNβ, IFNγ, and the like.

Exemplary toxin genes include, but are not limited to, diphtheria toxin A-chain gene (DTA), ricin A chain gene (Ric), herpesvirus thymidine kinase gene (tk), and *Pseudomonas* exotoxin gene (PE). Other suitable toxin genes will be apparent to those of skill in the art, such as suitable nucleases and proteases that, when expressed intracellularly as cytoplasmic proteins, lead to cell death. Alternatively, genes encoding a defective mutant of an essential cell protein (e.g., a housekeeping gene such as GAPDH) may kill cells by acting as competitive or noncompetitive inhibitors of the cognate normal protein (s).

The polynucleotide sequence, genetic constructs, therapeutic genes, and compositions of the present invention may be prepared in a variety of compositions, and may also be formulated in appropriate pharmaceutical vehicles for administration to human or animal subjects to affect the expression of the therapeutic gene in mammalian prostate cells. The compounds of the present invention, and compositions comprising them provide new and useful therapeutics for the treatment, control, and amelioration of symptoms of a variety of prostate disorders including prostate hypertrophy, prostate dysfunction, and diseases of the prostate, including hyperproliferative disorders such as cancers of the prostate, prostate tumors, and prostate hyperplasia. Moreover, pharmaceutical compositions comprising one or more of the nucleic acid compounds disclosed herein, provide significant advantages over existing conventional therapies—namely, (1) their reduced side effects, (2) their increased efficacy for prolonged periods of time, (3) their ability to provide prostate-specific expression of the selected therapeutic gene, and thereby provide high level expression of the therapeutic polypeptide directly to the tissues and cells of the prostate.

The present methods also avoid many of the untoward side effects of conventional therapies, avoid invasive surgical procedures, and are effective in lower, less frequent administration of the selected therapeutic.

The invention involves the synergy of individual regulatory elements within a gene's control region (i.e., a promoter or enhancer) to augment the transcriptional activity of that region. Site I was taken from the PSA promoter region and multimerized it and placed it upstream of a heterologous core promoter, the E4 promoter of adenovirus, creating the ARE4 construct. The artificial enhancer exhibited significant androgen-dependent activity. In contrast, the core region of the natural enhancer contained weaker androgen responsive activity but it was reported to be prostate specific in the literature by Trapman and colleagues. The invention involves an artificial enhancer fused to a natural enhancer resulting in an extremely potent ARE4 construct that would provide high activity and synergize with the AREs within the natural. This resulted in a chimera that retained specificity. Such a construct would be valuable as a prostate specific regulatory region for use in gene therapy.

2.1 Prostate-Specific Enhancer Elements

Preferred prostate-specific enhancer elements for use in construction of the disclosed genetic constructs preferably comprise one or more androgen response elements (ARE). The AREs may be native, site-specifically mutated, or completely, or partially-synthetic response elements. Particularly preferred prostate-specific enhancer elements comprise a plurality of 3, 4, 5, 6, 7, 8, 9, or even 10 or more ARE elements. The elements may be positioned within the polynucleotide sequence preferably in tandem, either in direct tandem, or inverted tandem fashion. When a plurality of AREs are present in the enhancer element, all of the elements may be in direct tandem fashion, or one or more of the elements may be present in inverted tandem fashion relative to the other AREs present on the particular construct. The plurality of ARE elements are preferably spaced such that there are no more than about 4 to 25 or so intervening nucleotides between each of the elements. The actual number of the intervening nucleotides is not critical, so long as the activity of the construct is maintained, and the intervening nucleotides may comprise any of the standard or substituted nucleotides, such as, e.g., C, A, T, or G.

A schematic illustration of the relative positioning of the elements of the genetic constructs of the invention, including those comprising two or more ARE elements is shown in FIG. 1A.

Particularly preferred prostate-specific enhancer elements are those that comprise one or more copies of the AREI element (AGAACAGCAAGTGCT; SEQ ID NO:1), a high-affinity AR binding site that is known to be functional in the context of the PSA gene. It is at position −170 of gene. The functional activity of AREI was first discussed by Riegman et al. (*Molec. Endocrinol.*, 5:1921-30, 1991). The region of the promoter bearing AREI was sequenced before AREI was functionally identified as an AR site. These sequences were by Klobeck et al.; GenBank Accession No. M14810) and by Lundwall (1989; GenBank Accession No. M27274).

Although the AREI sequence of Pang et al., (1995; Intl. Pat. Appl. Publ. No. WO 96/14875, specifically incorporated herein by reference in its entirety, 1996) differs by one nucleotide (AGAACAGCAAGTACT; SEQ ID NO:2), the inventors contemplate that it may also serve as a ARE element and may comprise all or part of the prostate-specific enhancer element. Likewise, other AREs including AREIII (GGAACATATTGTATT; SEQ ID NO:3; U.S. Pat. No. 6,110,702, specifically incorporated herein by reference in its entirety) are also expected to work in the present invention, since its affinity is close to AREI and it is located the PSA regulatory region, as is the AREIII element (GGAA-CATATTGTATC; SEQ ID NO:4) described in Schuur et al., (1997; GenBank Accession No. U37672).

As described above, these and other suitable AREs may be used in any combination to make up the final prostate-specific enhancer sequence, so long as the desired biological activity of the prostate-specific enhancer sequence is maintained. Likewise, as described above, each of the particular AREs that comprise such an enhancer may be present on the genetic construct in either direct, or inverted tandem fashion relative to the other AREs present, and each of the AREs may be separated by a sequence of intervening nucleotides so long as the desired biological activity of the prostate-specific enhancer sequence is maintained.

An illustrative chimeric enhancer element is shown in FIG. 1C and comprises the sequence shown in SEQ ID NO:5.

2.2 Gene Therapy Vectors

Currently, viral vectors show the greatest efficiency in gene transfer (reviewed in Anderson, 1998; Verma and Somia, Nature, 1997). For correction of genetic diseases such that persistent gene expression is required, retrovirus or lentivirus or AAV based vectors are desirable due to the integrating nature of the viral life cycle. However, for cancer therapy persistent expression is not needed and integration into host chromosomes is probably not desirable. Thus, adenovirus based vector is probably most suitable. The main advantages of adenovectors are high viral titers (not attainable with other viruses) that facilitate in vivo gene delivery and transfer. Adenovectors are the most frequently utilized in human cancer gene therapy trials.

Procedures for creating first generation adenovectors have been well-documented (Hitt et al., 1995). Gutless adenovector is the most advanced adenovirus derived vector where all viral coding sequences are deleted. This vector should be less immunogenic and several studies have documented improved and prolonged in vivo gene transduction in animal studies (Schiedner et al., 1998; Zou et al., 2000). Potential interference of proper functioning of the prostate specific promoter from residual adenoviral regulatory sequences is also minimized in a gutless adenovector (Steinwaerder and Lieber, 2000).

Non-viral vectors such as liposomal or particle mediated gene transfer is an emerging field with high industrial interest. If and when in vivo gene transfer can be consistently documented, then non-viral methods should be the method of choice. It is because this method should allow facile large-scale production without DNA therapeutic gene size limitation and reduced concerns of eliciting an immune response.

2.3 Biological Functional Equivalents

Modification and changes may be made in the structure of the polynucleotides and polypeptides of the present invention and still obtain a functional molecule that encodes a polypeptide with desirable characteristics, or still obtain a genetic construct with the desirable expression specificity and/or properties. As it is often desirable to introduce one or more mutations into a specific polynucleotide sequence, various means of introducing mutations into a polynucleotide or polypeptide sequence known to those of skill in the art may be employed for the preparation of heterologous sequences that may be introduced into the selected cell or animal species. In certain circumstances, the resulting encoded polypeptide sequence is altered by this mutation, or in other cases, the sequence of the polypeptide is unchanged by one or more mutations in the encoding polynucleotide. In other circumstances, one or more changes are introduced into the promoter and/or enhancer regions of the polynucleotide constructs to alter the activity, or specificity of the expression elements and thus alter the expression of the heterologous therapeutic nucleic acid segment operably positioned under the control of the elements.

When it is desirable to alter the amino acid sequence of one or more of the heterologous polypeptides encoded by the expression construct to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |

TABLE 1-continued

| Amino Acids | | | Codons | | | | | |
|---|---|---|---|---|---|---|---|---|
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those that are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

2.4 Definitions

In accordance with the present invention, nucleic acid sequences include and are not limited to DNA (including and not limited to genomic or extragenomic DNA), genes, RNA (including and not limited to mRNA and tRNA), nucleosides, and suitable nucleic acid segments either obtained from native sources, chemically synthesized, modified, or otherwise prepared by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

A, an: In accordance with long standing patent law convention, the words "a" and "an" when used in this application, including the claims, denotes "one or more".

Expression: The combination of intracellular processes, including transcription and translation undergone by a coding DNA molecule such as a structural gene to produce a polypeptide.

Proximal Promoter: an expression control element immediately upstream of a core promoter sequence that binds one or more regulatory polypeptides that regulate transcription by RNA polymerase bound at the core promoter.

Distal Enhancer: a non-contiguous expression control element located either upstream of the proximal promoter at sometimes great distance, or downstream, also sometimes at great distance, and sometimes within an intron.

Core Promoter: an expression control element for a structural gene to which RNA polymerase and its ancillary factors bind and initiate DNA transcription of the downstream gene; this term has been classically referred to in the literature as a "promoter."

Promoter: a term used to generally describe the region or regions of a DNA sequence that regulates transcription.

Regulatory Element: a term used to generally describe the region or regions of a DNA sequence that regulates transcription.

Structural gene: A gene that is expressed to produce a polypeptide.

Transformation: A process of introducing an exogenous DNA sequence (e.g. a vector, a recombinant DNA molecule) into a cell or protoplast in which that exogenous DNA is incorporated into a chromosome or is capable of autonomous replication.

Transformed cell: A cell whose nucleic acid complement has been altered by the introduction of one or more exogenous polynucleotides into that cell.

Transgenic cell: Any cell derived or regenerated from a transformed cell or derived from a transgenic cell.

Transgenic animal: An animal or progeny thereof derived from a transformed animal cell, wherein the animal's DNA contains an introduced exogenous nucleic acid molecule not originally present in a native, wild type, non-transgenic animal of the same species. The terms "transgenic animal"

and "transformed animal" have sometimes been used in the art as synonymous terms to define an animal, the DNA of which contains an exogenous DNA molecule.

Vector: A nucleic acid molecule, typically comprised of DNA, capable of replication in a host cell and/or to which another nucleic acid segment can be operatively linked so as to bring about replication of the attached segment. A plasmid or a virus is an exemplary vector.

The terms "substantially corresponds to", "substantially homologous", or "substantial identity" as used herein denotes a characteristic of a nucleic acid sequence, wherein a nucleic acid sequence has at least about 70 or about 75 percent sequence identity as compared to a reference sequence, typically at least about 80 or about 85 percent sequence identity, and more preferably at least about 90, 91, 92, 93, 94, or 95 percent sequence identity as compared to a reference sequence, and more preferably still, often at least about 96, 97, 98, or 99 percent identical. The percentage of sequence identity may be calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. Desirably the extent of similarity between the two sequences will be at least about 80%, preferably at least about 90%, and more preferably about 95% or higher, in accordance with the FASTA program analysis (Pearson and Lipman, 1988).

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

3.0 BRIEF DESCRIPTION OF THE DRAWINGS

The invention may be understood by reference to the following description taken in conjunction with the accompanying drawings, in which like reference numerals identify like elements, and in which:

FIG. 1A shows a schematic illustration of various combinations of the enhancer and promoter elements that may be present on the polynucleotide constructs described herein for the tissue-specific expression of heterologous nucleic acid sequences in the mammalian prostate.

FIG. 1B shows a schematic of the arrangement of ARE elements within the prostate-specific enhancer sequence of the invention. The elements may be preceded or succeeded by a nucleotide sequence of from about 1 to about 39 nucleotides, and the intervening space between each of the elements will typically vary of from about 1 to about 20 nucleotides. Any practical number of ARE elements may be present, and this figure exemplifies enhancers that comprise 2, 3, or 4 tandem ARE elements. As indicated, the orientation of the elements may be the same or they may be different. For example, they may all be direct tandem elements, or they may all be inverted tandem elements, or they may have a mixed configuration with one or more in the "forward" orientation, and one or more in the "reverse" orientation. The ARE elements may all be the same (e.g., 2, 3 or 4 copies, respectively of SEQ ID NO:1, SEQ ID NO:2, SEQ ID NO:3, or SEQ ID NO:4), or alternatively, they may represent a combination of two or more different elements (e.g., a 4 tandem enhancer may be comprised of 1 copy of SEQ ID NO:1+3 copies of SEQ ID NO:2, or 1 copy of SEQ ID NO:2 and 3 copies of SEQ ID NO:1, or two copies each of elements comprising the sequence of SEQ ID NO:3 and SEQ ID NO:4, etc.).

FIG. 1C shows a preferred enhancer element of the invention. Shown is the sequence of the full length of ARE4 (SEQ ID NO:5) the artificial enhancer comprising four tandem copies of the PSA AREI element (SEQ ID NO:1), the first in the reverse orientation, the next three in the forward orientation. According to the general structure shown in FIG. 1B, this element can be represented as a four-tandem repeat, where $X_1=39$, $X_2=12$, and $X_3=22$; and $ARE_1$=SEQ ID NO:1 (reverse), $ARE_2$, $ARE_3$, and $ARE_4$=SEQ ID NO:1 (forward). For clarity, the AREs have been bracketed and shown in bold, and the 3' and 5' NcoI sites and the 5' BstEII site have been underlined.

Figure 4A:
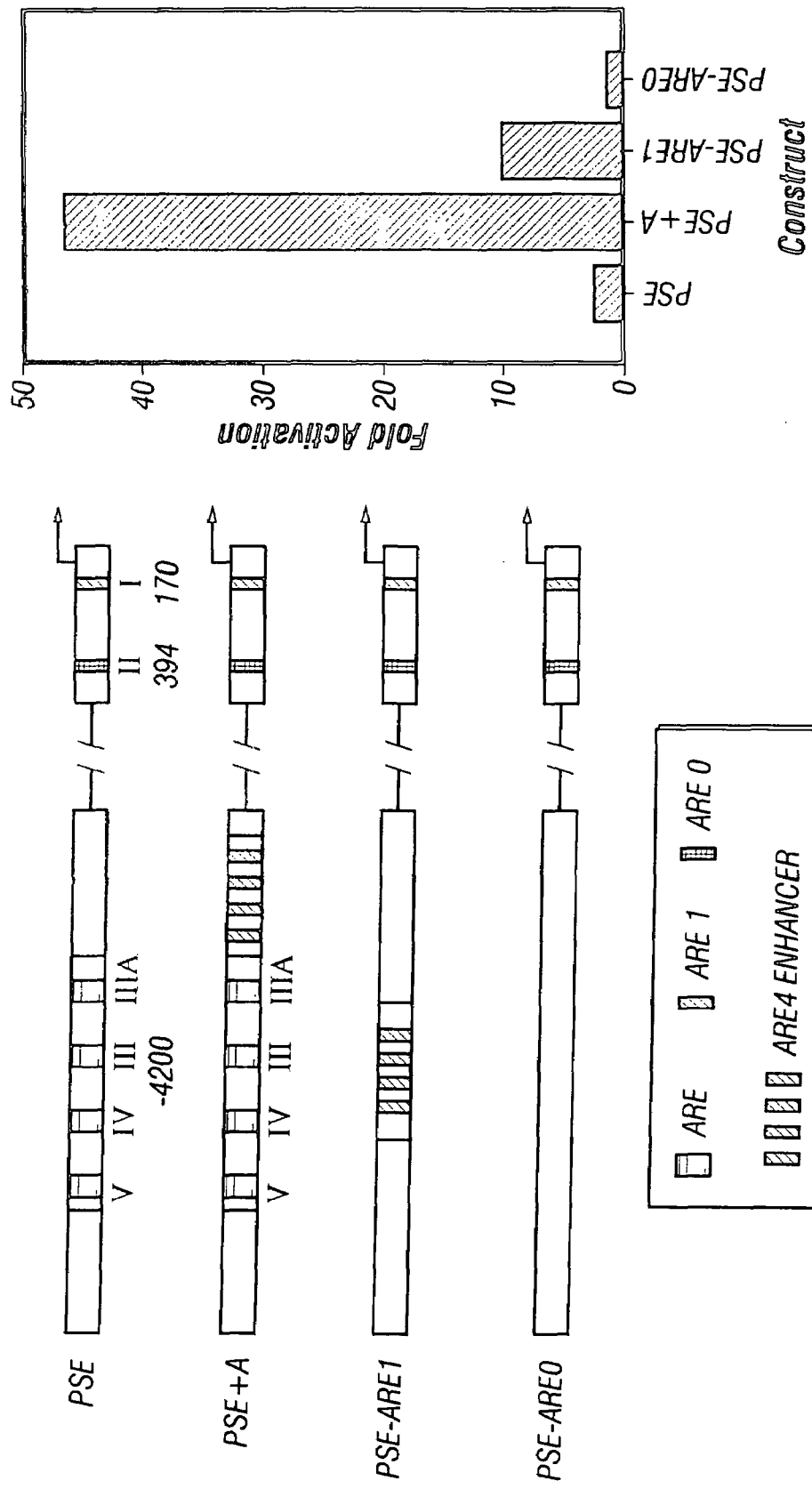

FIG. 4A shows 200 ng of each of the constructs were compared by co-transfection into f-LNCaP cells using Tfx-50 reagent. Fold activation in the presence of R1881 was measured. Clearly the activity of PSA-bearing both the wild type and natural enhancers in what is known as the (−) orientation was greater than the activity of either the natural PSA enhancer (PSE) or a chimera bearing ARE4 in place of the enhancer (ARE1).

Figure 4B:
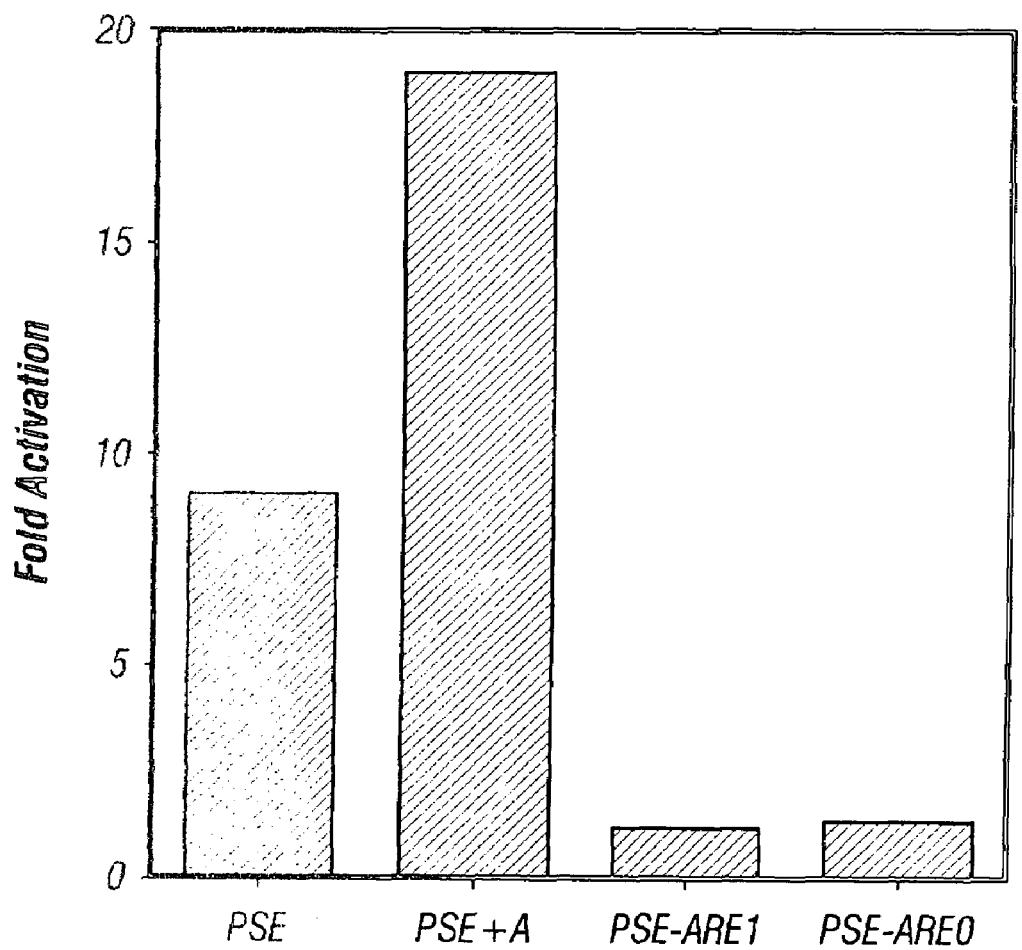

FIG. 4B shows a histogram showing the fold activation of the luciferase reporter gene in an androgen-inducible transcription assay comparing LAPC4 cells carrying various artificial enhancer constructs, such as PSE, PSE+A, PSE-ARE1, and PSE-ARE0.

Figure 4C:
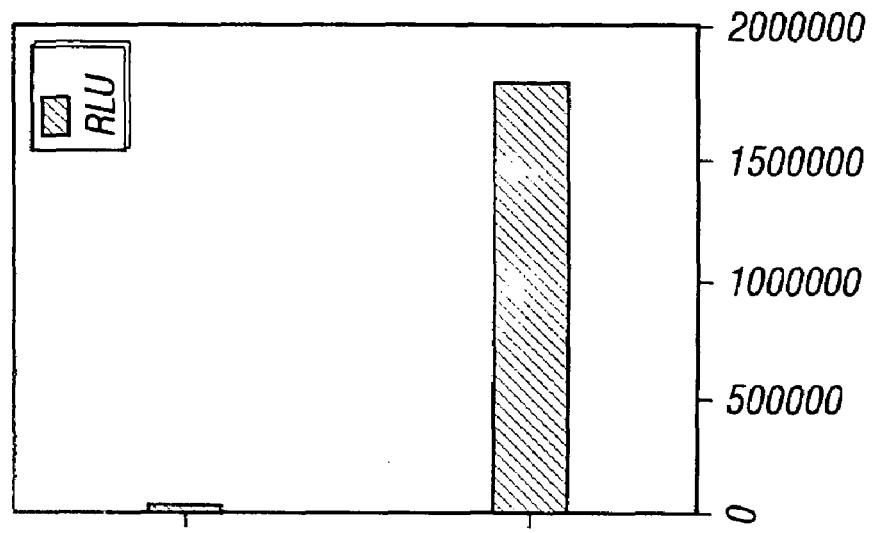
Figure 4C:
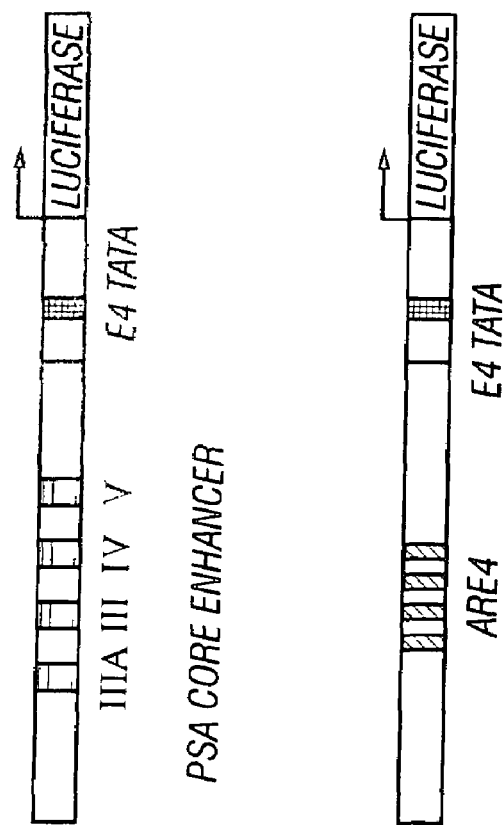

FIG. 4C shows a comparison of ARE4 vs. the core PSA enhancer. The histogram shows the relative luciferase units (RLU) detected in an androgen-inducible transcription assay comparing f-LNCaP cells that do not contain the artificial enhancer sequence construct (e.g., wild type) with the f-LNCaP cells carrying the artificial enhancer construct ARE 4E4T. These data are from a study where ARE4 upstream of a reporter containing the E4 core promoter in pGL3 (Promega) was compared with the construct bearing the wild type enhancer upstream of E4 in pGL3. Drawings of each construct are shown. 200 ng of each vector was transfected in f-LNCaP cells (see Huang et al., 1999) in the presence and absence of the androgen analogue R1881. Androgen inducible luciferase activity was measured and the relative light units of luciferase from the assay were directly compared. The fold activation relative to basal activity is not necessarily relevant but is 6-fold for wild type core enhancer and 4213-fold for the ARE4.

Figure 5:
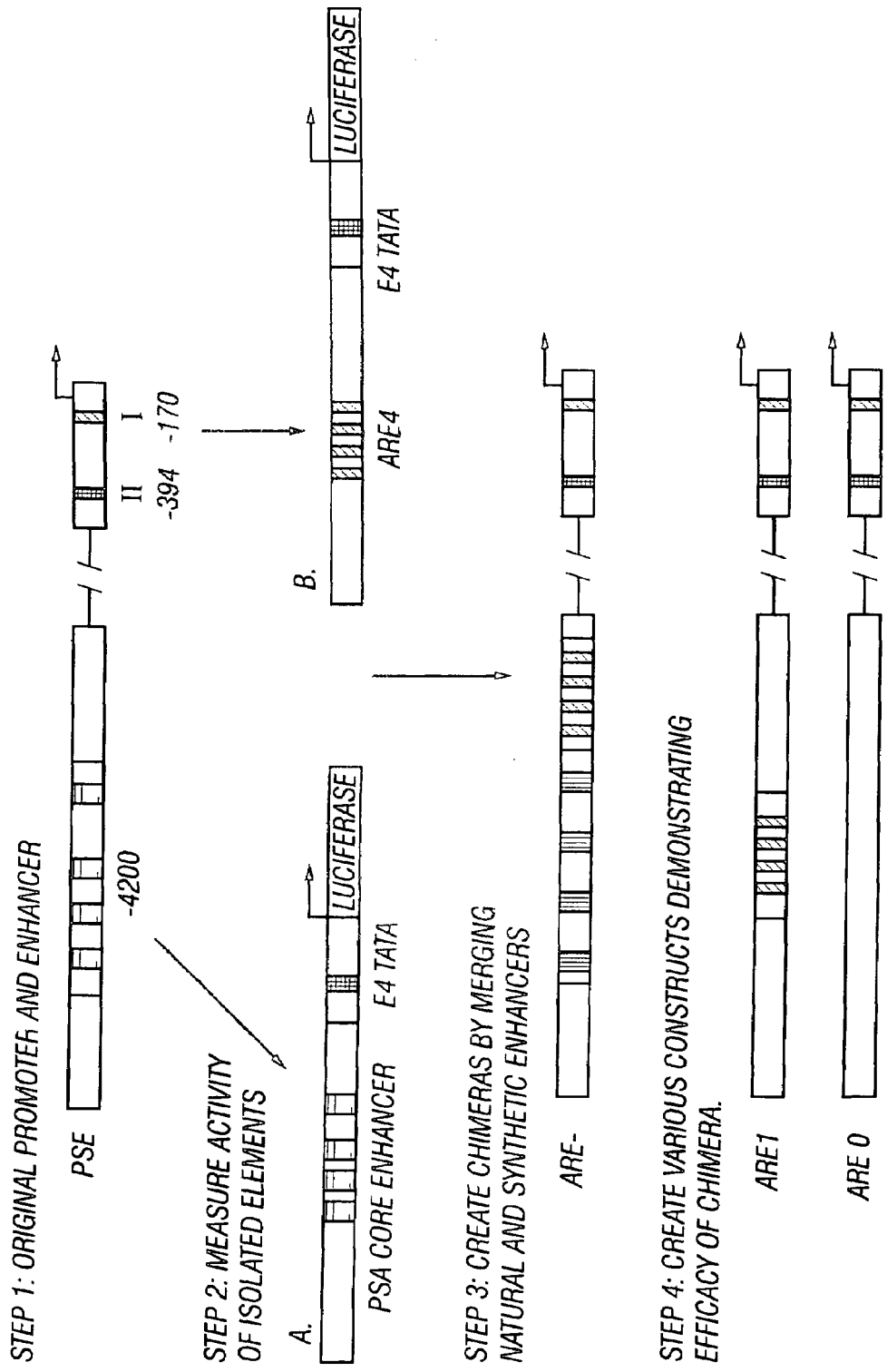

FIG. 5 outlines schematically the steps leading to the development of the initial illustrative genetic constructs of the invention. Step 1 began with the natural PSA enhancer and promoter. Step 2A utilized the core enhancer identified by Trapman and colleagues bearing multiple AREs as shown by Huang et al. for cloning upstream of a heterologous promoter (E4) to measure its activity in isolation. Step 2B involved placing ARE4 upstream of the same element and measuring its activity in a side-by-side comparison. Step 3 fused the artificial ARE4 to the natural core enhancer in the context of the entire natural PSA promoter and enhancer. Controls in which the natural enhancer was removed and replaced by ARE4 were also constructed to demonstrate that the synergy was necessary for the augmented activity of the chimera.

Figure 6:
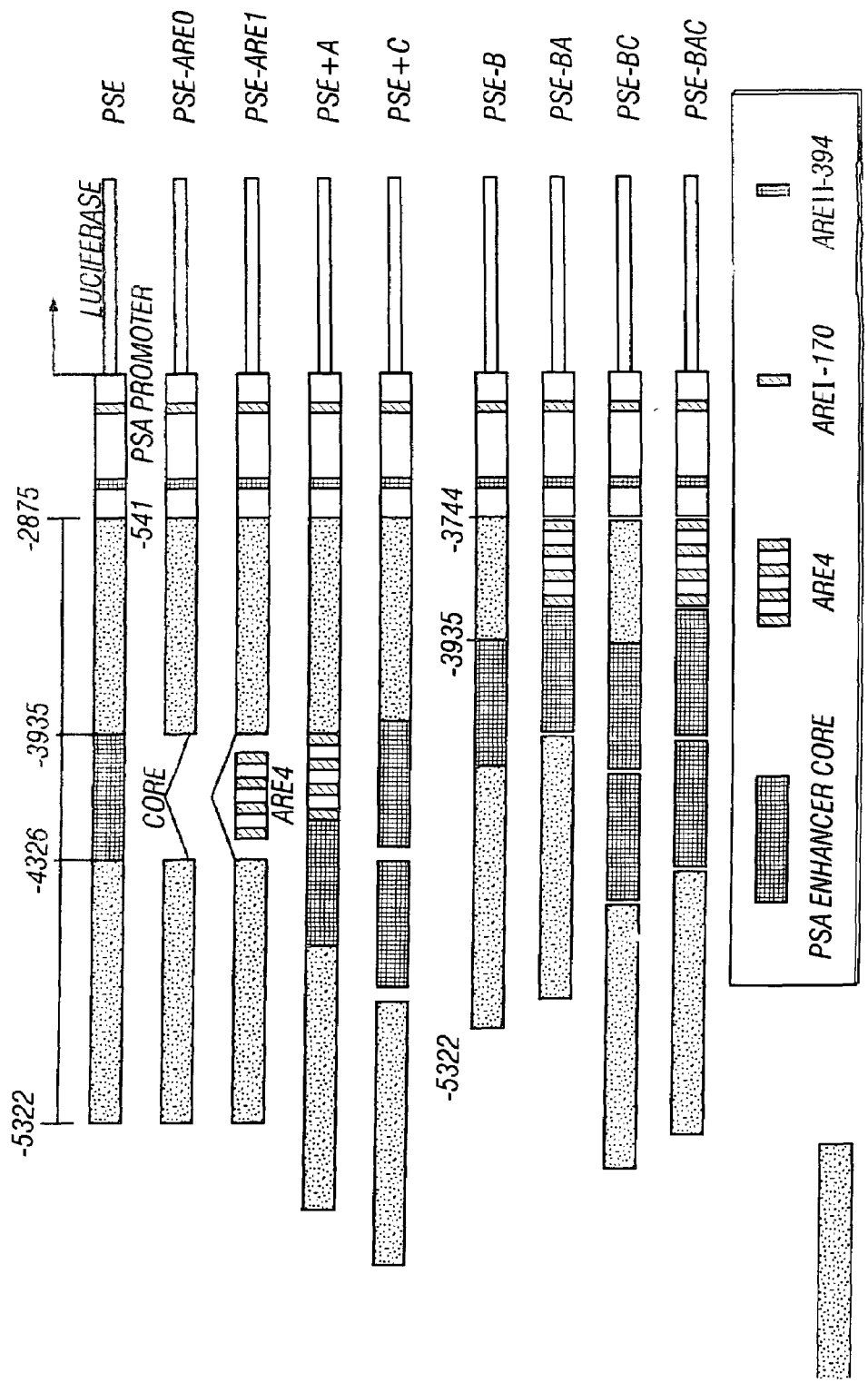

FIG. 6 shows various PSA enhancer/luciferase constructs that have been developed in connection with one aspect of the present invention. PSE represents the starting construct defined in Pang et al., (1997) bearing the ~2.4 Kb enhancer and 541 bp promoter. Core indicates the region between the BstEII and NcoI sites and bears the key ARE elements defined in Huang et al. (1999). ARE4 indicates the sequences defined in SEQ ID NO:5. The results demonstrated first, that combining ARE4 and core, or duplicating the core, generated a synergistic effect—augmenting activity while maintaining specificity. The constructs testing this are the PSE plus ARE4 (PSE+A) and PSE plus an additional copy of core (PSE+C). Controls for the effects are PSE alone, (PSE); PSE lacking the core (PSEARE0) and PSE containing ARE4 in place of the core (PSEARE1). The data shown in subsequent figures show that PSE+C and PSE+A are considerably more active that PSE alone or PSEARE1. These results also showed that moving the enhancer closer to the promoter would up-regulate activity. This set of constructs is termed the PSE-B series. These removed sequences between either −3935 to −2875 or −3744 to −2875. These alterations were shown to further augment activity.

Figure 7:
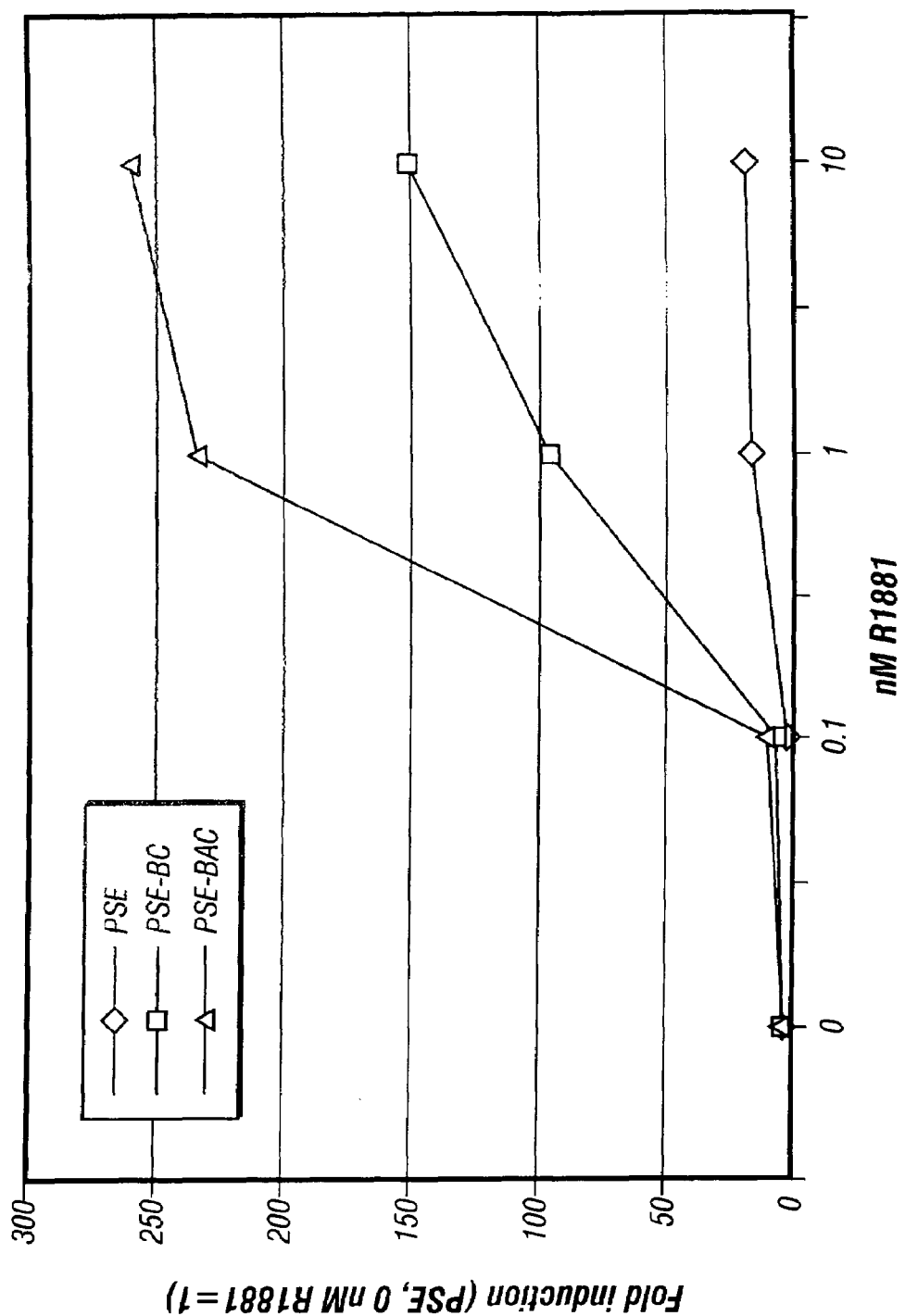

FIG. 7 demonstrates the androgen induction of several of the PSA enhancer constructs. The activity of the PSE, PSEBC and PSEBAC constructs, each bearing a downstream luciferase reporter gene, was assayed by transfection using the lipid reagent Lipofectamine Plus (Gibco) into LNCaP cells and varying concentrations of R1881 were added. The androgen inducibility of the chimeric constructs is greater than that of PSE. The vertical axis represents fold induction versus PSE measured in the absence of R1881.

Figure 8:
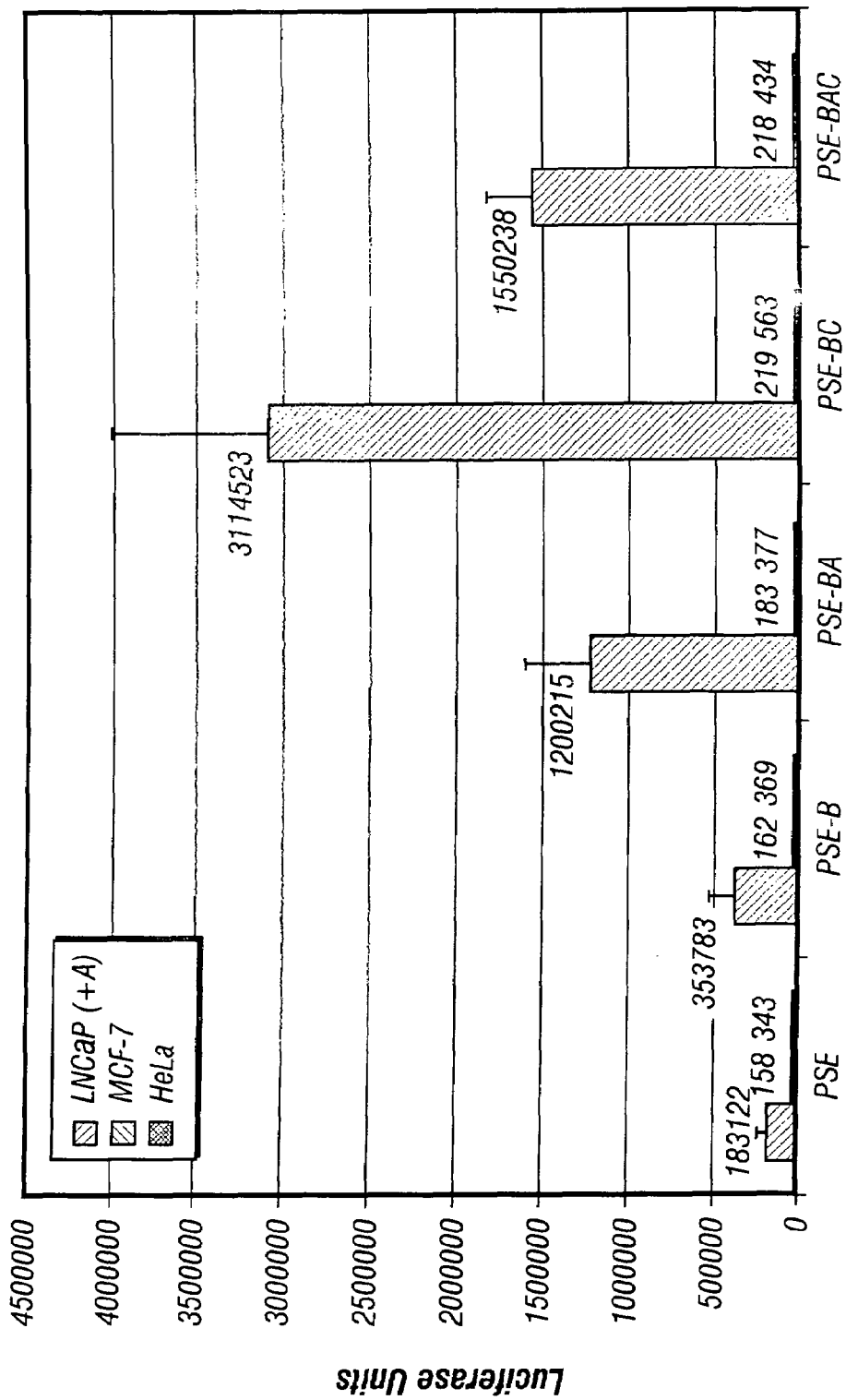
Figure 9:
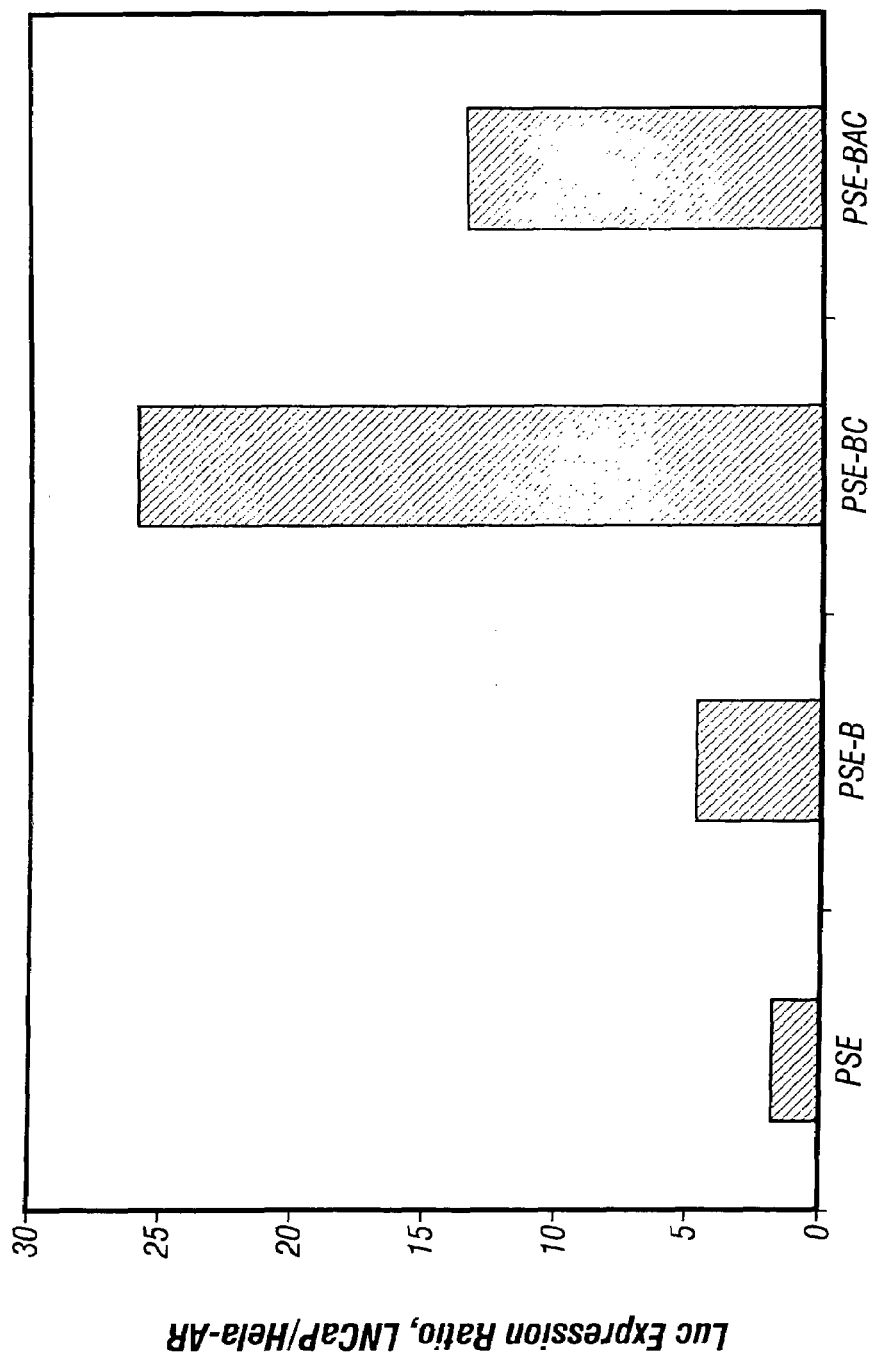

FIG. 8 shows the tissue specificity of the PSA enhancer constructs. Comparing parallel transfections into LNCaP and other non-prostate cells; MCF-7=breast cancer line; Hela=cervical carcinoma line. The experiment was done in the presence of R1881. The vertical axis represents absolute luciferase units. It was necessary to perform the comparison using Luc units because specificity is defined as the absolute activity of a construct in a cell line and absolute activities can only be compared directly or against an internal standard like CMV luciferase. Here absolute numbers were used, but the data have been plotted relative to CMV. The numbers above the bars show the absolute activities FIG. 9 shows the prostate specific expression of the PSA enhancer constructs. The chimeric constructs still retained specificity even when excess androgen receptor (AR) was expressed in non-prostate cells. Hela-AR is a cervical carcinoma cell line that stably expresses high-levels of AR (Huang et al, 1999). The chimeric constructs express in LNCaP prostate cells at levels even higher than the artificial setting in Hela-AR.

Figure 10A:
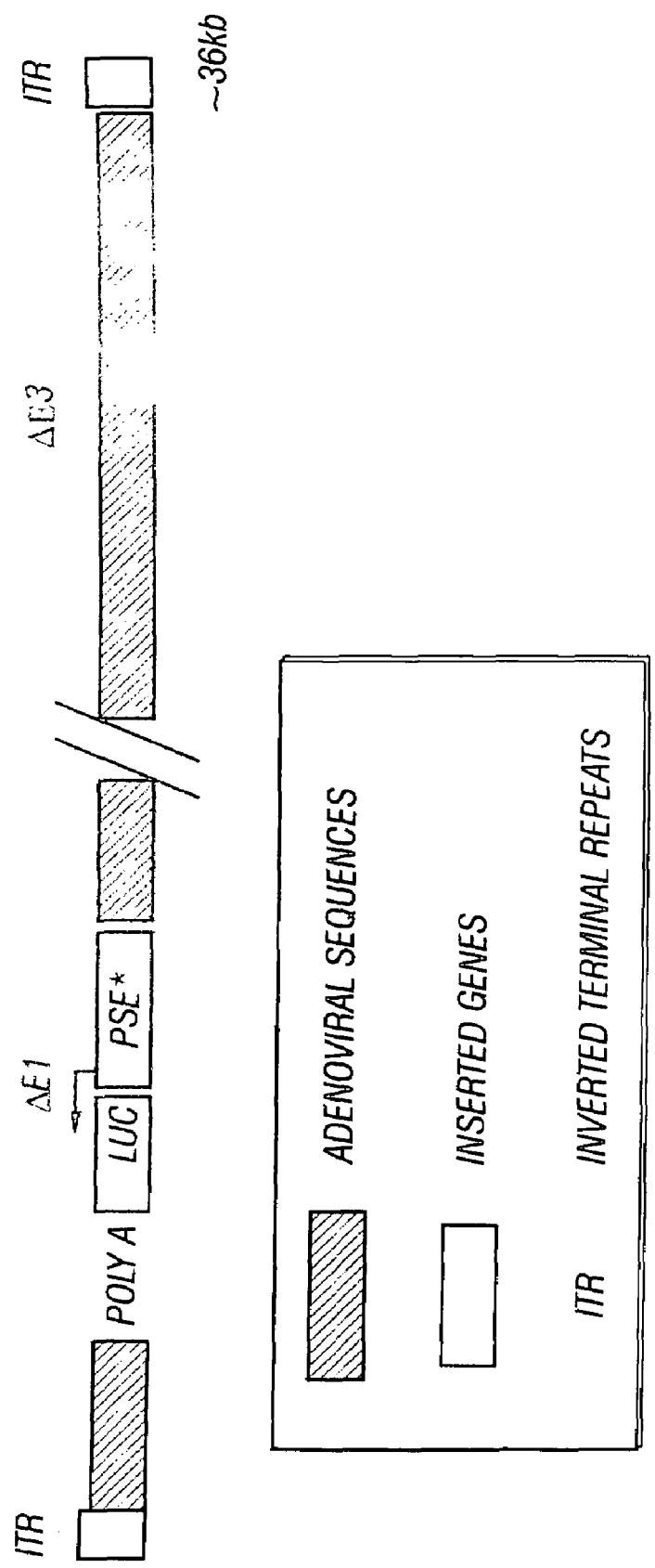

FIG. 10A shows the use of adenovector to evaluate new PSE promoter constructs, and the genomic structure of a viral vector construct, AdPSE*-Luc. Recombinant Ad is a viral vector that was demonstrated to be capable of in vivo gene transfer. To assess the activity of various chimeric enhancer constructs in vivo in a model setting, recombinant Ad were prepared that contained the regulatory elements driving the luciferase reporter gene. In particular, Ad PSE-B luc was created because the PSE-B construct is similar to the regulatory region used in the Calydon virus CN706 which is currently used in clinical trials (That enhancer is −5322 to −3738 plus promoter −541 to +12. The PSE-B construct is −5322 to −3744 plus promoter −541 to +12. The two regions also differ slightly in sequence as indicated in the published DNA sequences. In addition, Ad PSE-BC luc was also generated in which the luc expression cassette replaced the deleted E1 Ad sequence from 453 to 3323. This viral deletion renders the virus replication defective.

Figure 10B:
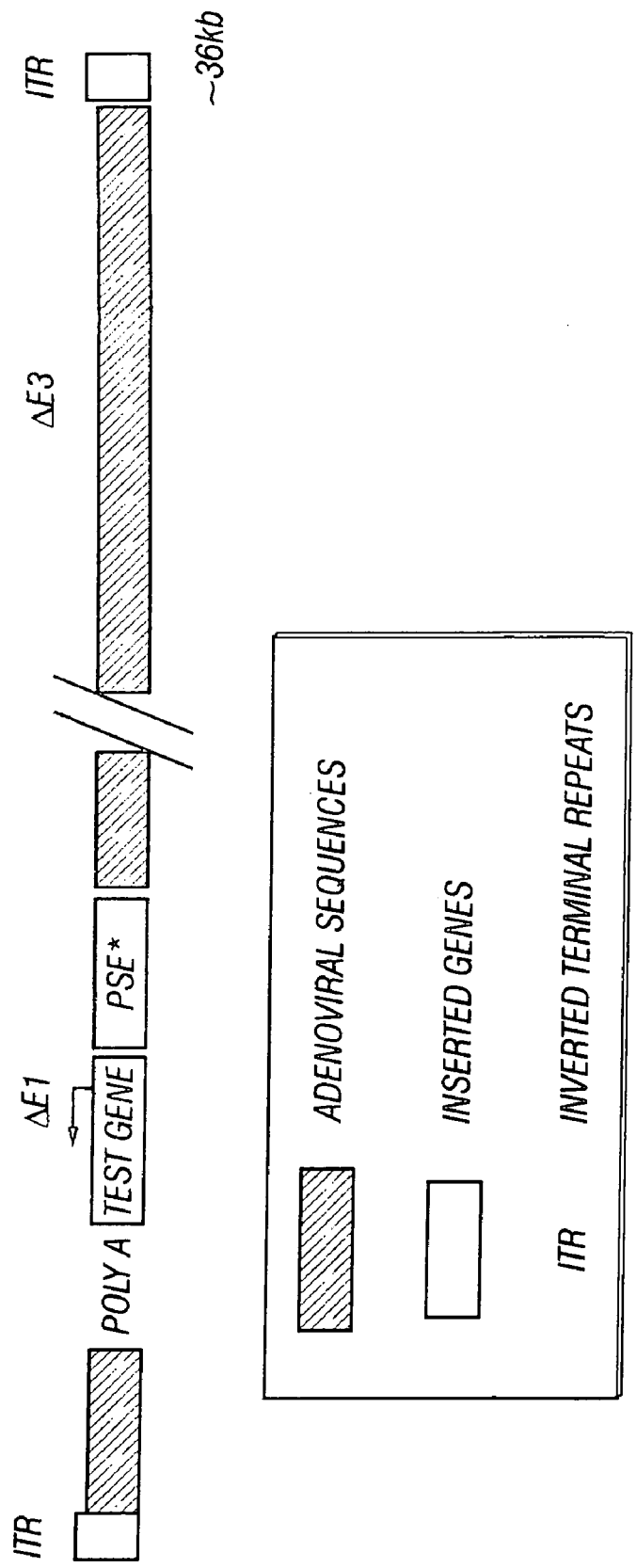

FIG. 10B shows the adaptation of the viral construct in FIG. 10A where the reporter gene, luciferase is replaced by a therapeutic gene of interest in the genetic construct.

Figure 11:
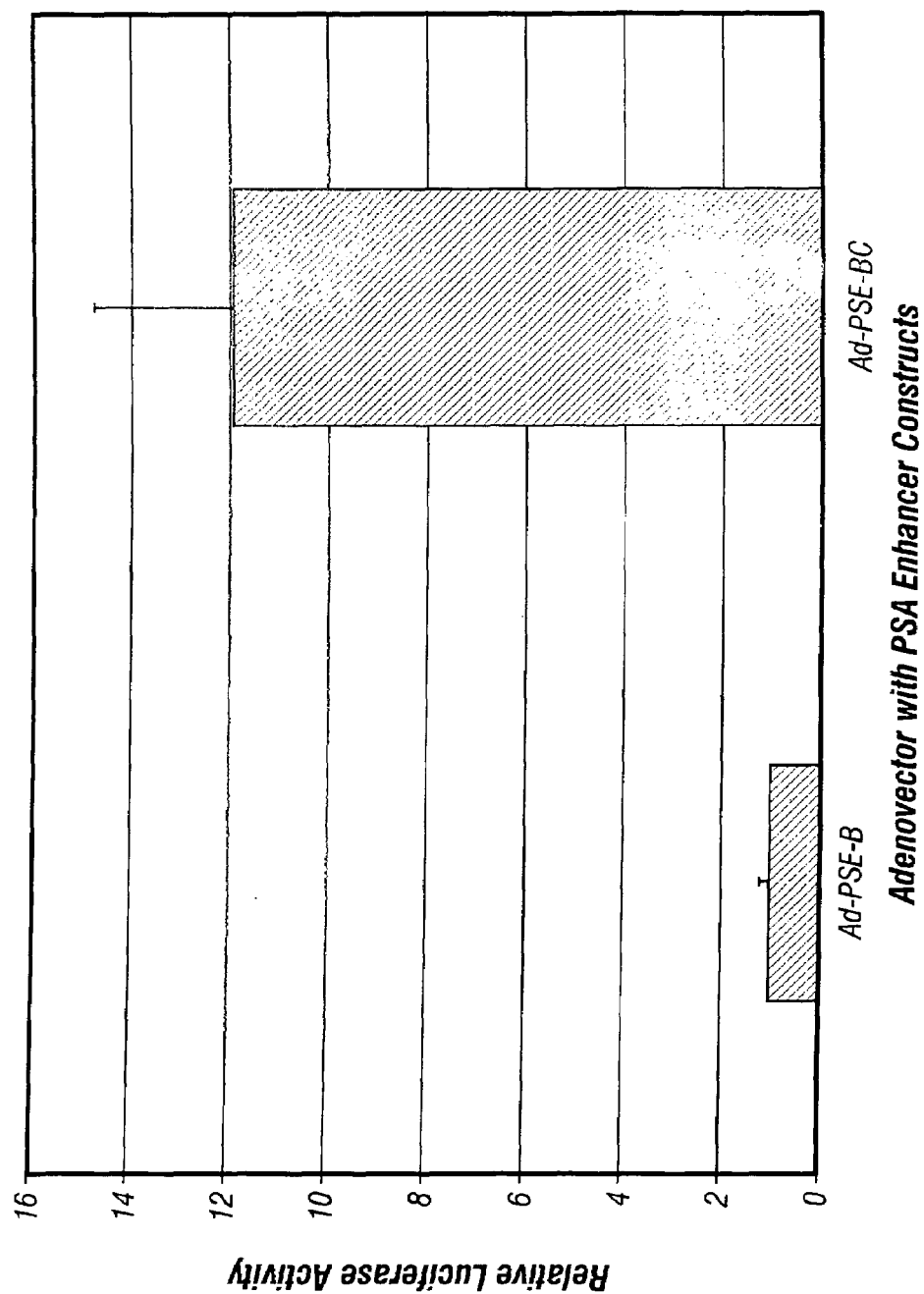

FIG. 11 shows the relative luciferase activity of the adenoviral vector PSA enhancer constructs in prostate cells, LNCaP. The luciferase activity from AdPSE-BCluc infected LNCaP cells are 12-fold higher then equivalently infected with AdPSE-Bluc. The result represented in this figure hold the luciferase units from AdPSE-Bluc infected cells arbitrary at 1

Figure 12:
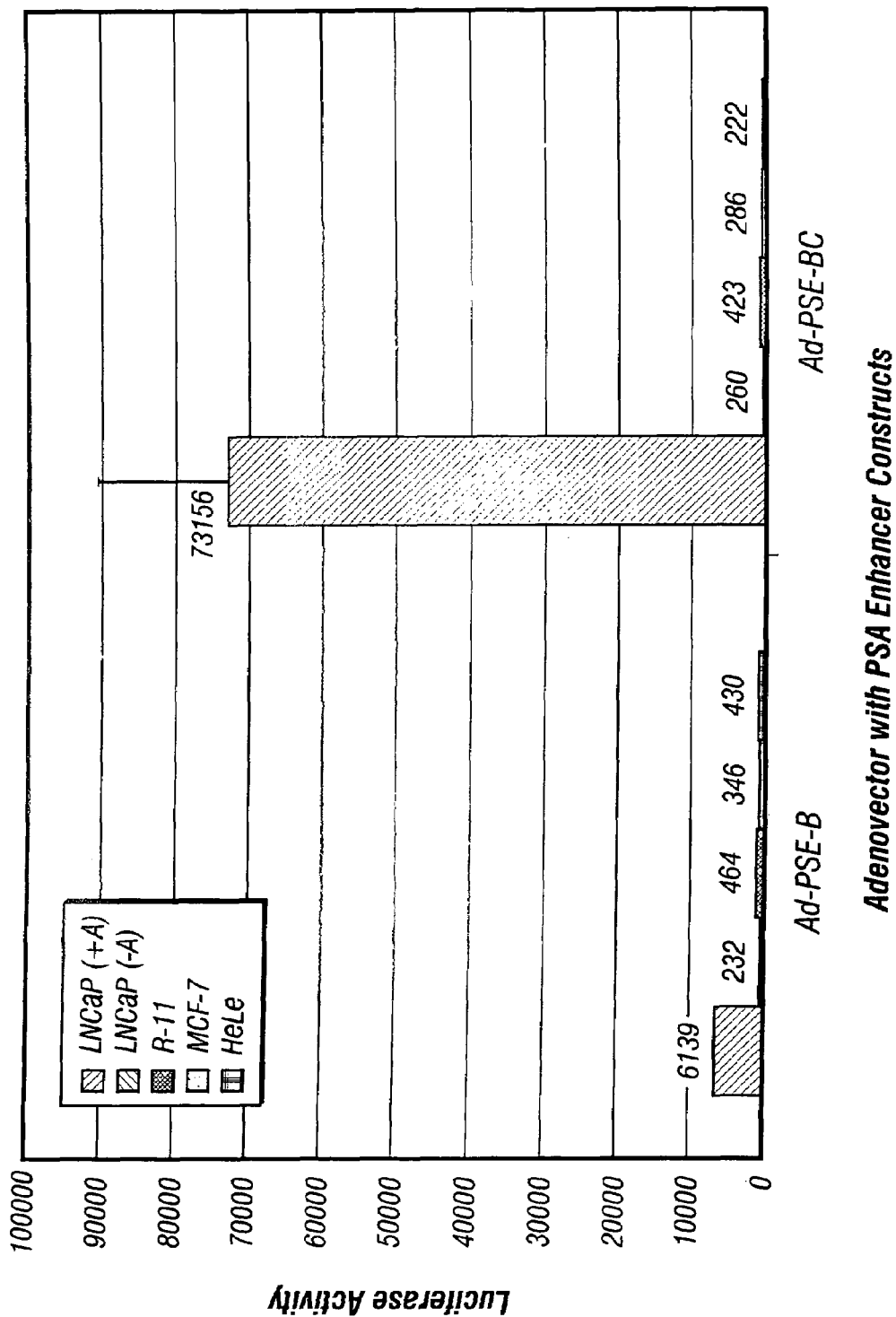

FIG. 12 shows the relative luciferase activity of the adenoviral vector PSA enhancer constructs following Ad infection. Specificity and androgen response was retained in AdPSE-BC. Different cell types were infected with AdPSE-Bluc or AdPSE-Bcluc equivalently at an MOI 5. LNCaP cells were first maintained for 24 hrs prior to infection in RPMI media with 10% charcoal treated FBS (to remove androgen). After infection, LNCaP cells were replaced with either this same media (−A) or with 1 nM R1881 added (+A). All other cells are maintained in media containing 1 nM R1881. R-11 is a renal carcinoma line. MCF-7 and Hela cells are as described above.

Figure 13:
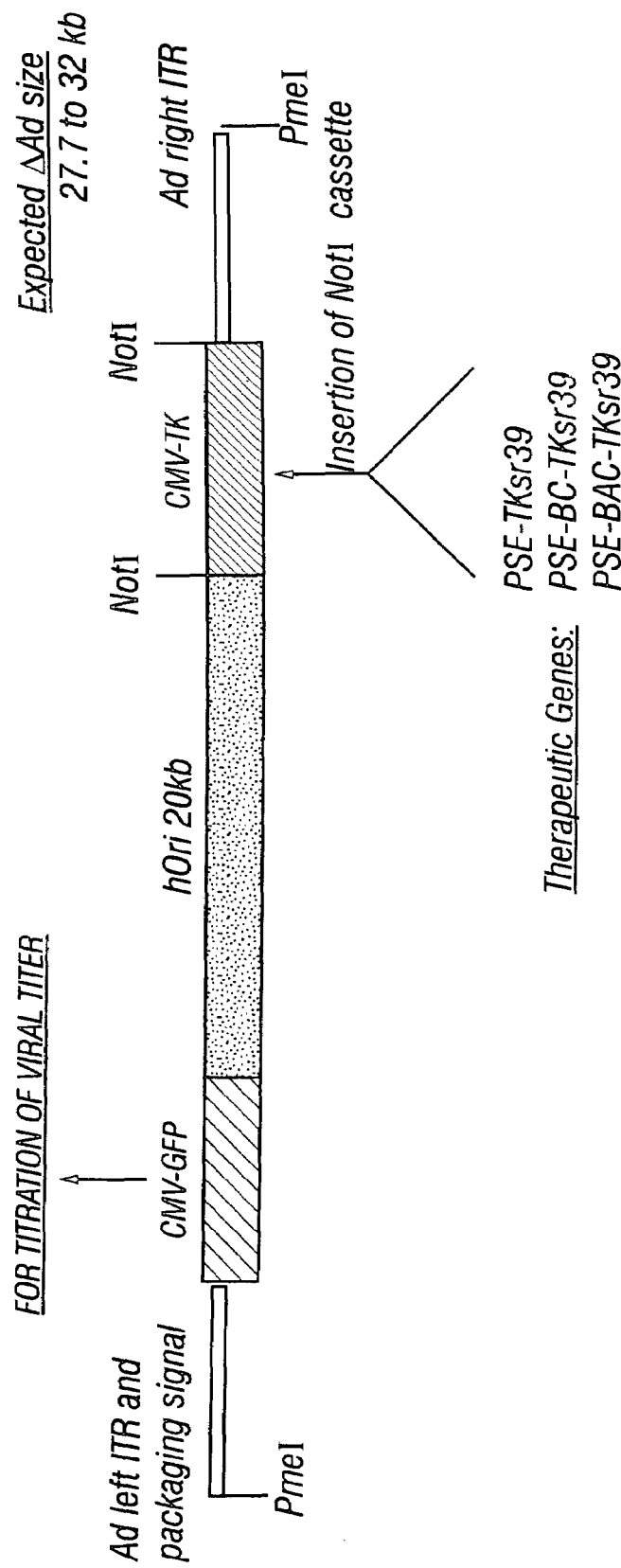

FIG. 13 shows a schematic diagram of the gutless adenoviral vector system in which the prostate-specific expression cassettes of the present invention may be cloned for administration of the constructs to a mammal. In this illustration, the SR39 variant of the thymidine kinase gene is shown as the selected therapeutic gene.

4.0 DETAILED DESCRIPTION OF THE INVENTION

In order that the invention herein described may be more fully understood, the following description is set forth.

4.1 Diseases of the Prostate

Three significant diseases of the prostate have been described: benign prostatic hyperplasia (BPH), prostate cancer, and prostatitis. Prostate cancer has claimed the lives of more than 40,000 Americans, and BPH represents one of the most significant diseases of men over the age of fifty.

4.1.1 Benign Prostatic Hyperplasia

Some degree of BPH exists in almost 80% of the male population over the age of 80, and causes urinary obstruction that results in urinary incontinence. Unregulated dihydrotestosterone has been implicated in the development of hyperplastic prostate growth by older males. Therapy and treatment of the disorder focus primarily on relaxing prostate smooth muscle (alpha blockade) and decreasing total prostate volume (androgen suppression). For example, finasteride, a 4-aza steroid (Proscar® Merck & Co.), inhibits 5-α-reductase, the enzyme responsible for the intracellular conversion of testosterone to dihydrotestosterone in the stroma of the prostate. Since dihydrotestosterone is the most potent androgen in the prostate, its elimination causes regression of prostate cancer by as much as 40% in volume (Mocellini et al., 1993). Surgical intervention represents another treatment modality, with transurethral resection of the prostate (TURP) being utilized in almost a million cases annually. An unfortunate side effect of the surgery, however, is impotence in almost 90% of surgical patients.

4.1.2 Prostate Cancer

Cancer of the prostate (CaP) is the most common diagnosed non-skin cancer among men, and the second most common cause of cancer death in American males, exceeded only by lung cancer. A latent disease, many men have prostate cancer cells long before overt signs of the disease are apparent. Prostate cancer is newly diagnosed in slightly over 100,000 men in the U.S. each year of which over 40,000 will die of the disease. Cancer metastasis to the lymph nodes is an early stage complication of the disease, while metastasis to bone in its late stages is common and often associated with uncontrollable pain, and significant morbidity and mortality.

Nearly a third of newly diagnosed patients already have locally advanced or metastatic disease. Androgen deprivation therapy forms the basis of endocrine therapy for the majority of patients with advanced cancer. However, currently available treatments for metastatic CaP are not curative (Jones et al., 1995). The mechanisms of progression of CaP cells to hormone independence under androgen ablation therapy remain unclear. Whether cancer progression to an androgen independent stage involves tumor adaptation to the androgen withdrawal or selective outgrowth of preexisting androgen independent clones is unknown. To adequately investigate the factors and mechanisms that underlie the development of androgen resistance and metastasis, a reliable in vivo model that closely resembles human CaP progression is essential. Moreover, it is critical that this tumor model mirrors the pathology, cellular and molecular characteristics of advanced CaP if it is to serve as a useful tool for basic research, drug screening or for the evaluation of new therapeutic strategies.

A highly aggressive hormone-independent CaP tumor model has been developed in, the mouse, which was derived from the slow growing, poorly tumorigenic, androgen-dependent LNCaP cell line. CL1 was established by pre-ex-vivo selection of androgen-independent variants under androgen deprivation conditions (Thalmann et al., 1994). This developed into a fast-growing HRPC cell line and a tumor model in SCID mice was subsequently developed. The tumor growth was rapid and required no additional growth supplement to establish itself in mice. When transfected with the *Aequorea Victoria* green fluorescence protein gene (CL1-GFP) and transplanted orthotopically in SCID mice, extensive metastatic spread from the primary tumor was identified in various organs using fluorescence microscopy. This model was defined based on histologic appearance, biological behavior and molecular characterization and these results were compared to the features of the advanced CaP. Details of this model are provided in the examples that follow.

4.2 Prostate Specific Antigen

Diagnosis and management of the disease has been simplified with the development of tests that measure serum levels of prostate-specific antigen. Prostate specific antigen (PSA) is a kallikrein protease involved in semen liquification but may also be involved in tumor cell activity. Normal, hyperplastic and malignant prostate epithelia (Aumüller et al., 1990) specifically express PSA, of which the serum level is widely used clinically as a marker for diagnosis and management of prostate cancer (Catalona et al., 1991; Young et al., 1992). The regulatory regions of PSA gene are prime candidates to direct prostate-specific expression given their strong tissue-specificity (Schuur et al., 1996; Cleutjens et al., 1997a; Pang et al., 1997). Moreover, these regulatory regions display dramatic androgen-responsiveness consistent with the observation that these regions contain androgen receptor (AR) binding sites (called AREs). The PSA gene represents a model for studying AR-mediated gene expression during prostate cancer (Young et al., 1990) as it is upregulated as a function of tumor burden both in the androgen-dependent and early independent stages of cancer growth.

4.3 The PSA Promoter and Enhancer

Recent studies have established that the 6-kb region upstream of the PSA gene contained all the genetic information to direct androgen responsive and prostate specific expression in a transgenic mouse model (Cleutjens et al., 1997b; Wei et al., 1997). The PSA promoter, a region approximately 600 bp immediately upstream of transcription initiation site, contains a TATA box and two androgen responsive elements or AREs (Riegman et al., 1991; Pang et al., 1995; Cleutjens et al., 1996; Zhang et al., 1997a; Zhang et al., 1997b; Luke and Coffey, 1994). The region is capable of directing tissue specific expression in vitro. However, this promoter alone was shown to be insufficient to direct prostate specific reporter gene (Cleutjens et al., 1997b) or Ha-rasT24 oncogene expression (Schaffner et al., 1995) in transgenic mice studies.

Several groups had undertaken extensive biochemical and genetic analysis of the PSA regulatory region in an effort to streamline and define the minimal regulatory region that would cooperate synergistically with the proximal promoter to augment prostate specific transcription. At least three upstream androgen-responsive putative regulatory factor binding sites were mapped based on DNase I footprinting studies (Cleutjens et al., 1997a) with an high affinity ARE identified in a 440-bp core region centered at −4.2 kb upstream. Mutation of this ARE apparently inactivates the activity of this core (Cleutjens et al., 1997a; Zhang et al., 1997a; Zhang et al., 1997b). The enhancer fragment was originally identified in the literature as a 2086-bp fragment containing putative recognition sites of androgen receptor, AP-1, CREB and fos (Schuur et al., 1996). Subsequent studies have streamlined the enhancer activity to an 822-bp fragment (Pang et al., 1997) inclusive of the core region. The enhancer when fused to the promoter confers not only a high level of prostate specificity, assayed by linked reporter gene transfections (Schuur et al., 1996; Cleutjens et al., 1997a; Pang et al., 1997; Zhang et al., 1997a; Zhang et al., 1997b), but also dramatic androgen inducibility of over 100 fold in prostate cancer cells.

To further delineate the mechanism of PSA enhancer function, detailed genetic and biochemical dissection of the enhancer core region has been performed (Huang et al., 1999). It has been shown that the enhancer is much more complex and contains a cluster of six low-affinity, non-consensus AREs, which bind AR cooperatively and act synergistically to stimulate transcription. Recent studies in the gene expression field have established that nucleoprotein structures called enhanceosomes are the driving force behind tissue specific expression from an enhancer. In an enhanceosome multiple activators engage in specific, cooperative and often combinatorial interactions that lead to the assembly of a highly stable nucleoprotein structure that governs the specificity of transcription (Bruhn et al., 1997; Carey, 1998; Falvo et al., 1995; Thanos and Maniatis, 1995). It is plausible that AR forms such a structure on the PSA enhancer.

4.4 Androgen Receptor

Androgen receptor (AR) plays a central role in prostate cancer progression. Depletion of androgens by surgical or chemical treatments slows cancer growth. AR activates transcription of the gene encoding the kallikrein protease prostate-specific antigen (PSA) and other genes involved in secretory epithelial cell metabolism. Serum PSA levels parallel oncogenic growth in the initial androgen-dependent cancer. The prostate specificity of the PSA transcriptional regulatory region has made it an ideal reagent for use in gene therapy trials (Cheng et al., 1996; Rodriguez et al., 1997; Pang et al., 1997; Gotoh et al., 1998).

Biochemical and genetic studies have led to the cloning and partial genetic dissection of the PSA promoter and enhancer (Pang et al., 1997; Pang et al., 1995; Cleutjens, 1997a; Schuur et al., 1996; Cleutjens et al., 1996, Riegman et al., 1991). Both the enhancer and promoter display androgen responsiveness consistent with the observation that both regions contain androgen response elements (AREs) (Pang et al., 1997; Pang et al., 1995; Schuur et al., 1996; Cleutjens et al., 1996; Luke and Coffey, 1994; Zhang et al., 1997a; Zhang et al., 1997b; Sun et al., 1997). The proximal promoter has been delineated to an ~630-bp fragment containing a core TATA box (Pang et al., 1995) and two AREs, ARE I and ARE II (Cleutjens et al., 1996). AR activates transcription synergistically from these AREs (Cleutjens et al., 1996). Although the promoter plays an important role in PSA expression, an experiment in transgenic mice has shown that it is insufficient to confer strong androgen responsiveness and cell type specificity in vivo. In the same experiment, however, a 6-kb region encompassing the promoter and extending further upstream was able to mediate proper regulation (Cleutjens et al., 1997b).

An enhancer element, centered at approximately −4.2 kb, is located within this 6-kb region (Cleutjens, 1997a). The enhancer was originally identified as a 1.6-kb fragment containing, by sequence analysis, sites recognized by the androgen receptor, AP-1, cAMP-responsive element binding protein, and Fos (Schuur et al., 1996). Two studies further delineated the enhancer to an 822-bp fragment (Pang et al., 1997) and a 455-bp minimal core region encompassing an androgen-responsive DNase I-hypersensitive site (Cleutjens, 1997a). The role of the single identified ARE, termed ARE III, within this minimal core enhancer is not entirely clear. In one study, mutation of ARE III eliminated enhancer activity in transfection assays (Cleutjens, 1997a). In a different study, however, mutation of ARE III in combination with ARE I of the promoter was required to abolish androgen responsiveness (Zhang et al., 1997a; Zhang et al., 1997b).

AR is a 110-kDa protein containing an amino-terminal transcriptional activation domain (AF-1) spanning amino acids 141-338 (Doesburg et al., 1997; Chamberlain et al., 1996; Hong et al., 1996; Rundlett et al., 1990; Kuiper et al., 1993; Langley et al., 1995; Chang et al., 1988a), a zinc finger DNA binding domain from amino acids 556-623, and a carboxyl-terminal hormone/ligand binding domain from amino acids 666-918 (Chang et al., 1995). AR is a member of the nuclear receptor superfamily. The remarkable homology of the conserved domains suggests that family members will activate transcription using conceptually similar mechanisms (Evans, 1988). The ligand-binding domain contains an additional activation domain (AF-2) by virtue of its homology to similar regions in related receptors and its ability to interact with co-activators (Glass et al., 1997). Interaction between the amino- and carboxyl-terminal activation domains is thought to be important for full activity of AR (Doesburg et al., 1997; Wong et al., 1993). The regulatory functions of AR in transcription have been demonstrated both in vivo and in vitro (Rundlett et al., 1990; Limonta et al., 1995; De Vos et al., 1994; Warriar et al., 1993; Snoek et al., 1996).

The DNA binding domain of AR is a dimer and exhibits strong sequence homology with the progesterone (PR) and glucocorticoid (GR) receptors (Chang et al., 1988b; Hollenberg et al., 1985; Misrahi et al., 1987; Lubahn et al., 1988). Expression of androgen-responsive genes is regulated by binding of ligand-activated AR to androgen response elements (AREs). Characterization of different AREs indicates that there are two classes of sites (Chang et al., 1995). One group contains the 15-bp near-dyad, consensus sequence: GG(A/T)ACAnnnTGTTCT (SEQ ID NO:6). The consensus also binds to and mediates transactivation by GR and PR. A second class of sites, however, has been identified with sequences that diverge considerably from the consensus. It is likely that these non-consensus sites contribute to specific binding by AR (Huang et al., 1999; Cleutjens et al., 1996; Claessens et al., 1996; Scheller et al., 1998; Kasper et al., 1994).

AREs are found in promoters of genes expressed in different tissues including prostate, brain, kidney, liver, and testis (Chang et al., 1995). It is unlikely therefore, that AR alone regulates cell-type specificity of PSA gene expression. Indeed, DNase I footprinting and gel shift studies have identified several binding sites for prostate-specific and ubiquitous transcription factors within the PSA enhancer and promoter (Schuur et al., 1996; Riegman et al., 1991; Sun et al., 1997). It is likely that a combination of AR and cell-specific factors confers tissue selectivity. One of the hallmarks of such regulation is the formation of nucleoprotein complexes that use cooperative DNA binding and transcriptional synergy to elicit specific patterns of gene expression (Carey, 1998).

In an effort to understand the regulation of the PSA gene as a model for AR-mediated gene expression during prostate cancer, the core enhancer has been analyzed in detail biochemically. DNase I footprinting has been employed to demonstrate that the enhancer contains a cluster of six closely spaced putative AREs differing in affinity for recombinant AR DNA binding domain (ARDBD). Systematic mutation of these sites demonstrated that at least four of the six sites were physiologically relevant in conferring response to AR in co-transfection assays into BHK and LNCaP cells. A retroviral construct encoding a FLAG-tagged version of AR was developed and introduced into HeLa and LNCaP cells, and the receptor was isolated by immunoaffinity chromatography. Transactivation, nuclear translocation, and DNA binding assays demonstrated that the FLAG-tagged AR was biologically active in vivo and in vitro. Purified fAR bound cooperatively to the four core sites in the enhancer and responded to ARE mutants in a manner that roughly paralleled the in vivo transcriptional analysis. Conversely, PR did not substantially activate transcription from the core enhancer but did activate from a reporter-bearing tandem AREs.

4.5 Prostate Specific Gene Therapy Studies

Several in vitro transfection studies have utilized the PSA regulatory region to drive therapeutic gene such as p53 (Lee et al., 2000), sodium iodide symporter (Spitzweg et al., 1999), or herpes simplex Thymidine Kinase (Gotoh et al., 1998). Overall, these studies illustrated that PSA promoter can mediate some level of prostate specific and androgen responsive expression, which is consistent with results, established with linked marker gene studies. Although therapeutic responses measured by tumor cell killings were established, the in vivo gene delivery and responses could not be assessed by these studies.

Very few studies have evaluated the PSA promoter and enhancer function in a vector that has documented gene transfer efficacy in an in vivo model. Recombinant adenovirus vectors (adenovectors) have the capacity to deliver gene efficiently in vivo and especially intra-prostatically (Steiner et al., 1999). Currently several on-going human prostate cancer clinical trials have utilized the adenovectors (Herman et al., 1999; Rodriguez et al., 1997). Two groups have proceeded to use the PSA regulatory regions in adenovectors to direct prostate-specific expression of cytotoxic HSV TK (Gotoh et al., 1998) or viral E1A (Rodriguez et al., 1997) to induce lytic viral replication. However, compared to plasmid transfections both adenovectors (Gotoh et al., 1998; Rodriguez et al., 1997) appeared to exert reduced discriminatory expression in permissive cells, i.e., PSA producing cells, over non-permissive cells. The Ad-PSA-TK expressed TK enzyme in LNCaP cells was approximately 10-fold higher than in non-permissive WH bladder cells and the androgen induction was less than 10-fold (Gotoh et al., 1998). Studies have illustrated that the native PSA enhancer and promoter (PSE, consisted of −5322 to −2875 and −541 to +11 of PSA gene) inserted into adenovector indeed can direct tissue specific and androgen-inducible expression in PSA expressing cells, but its transcriptional activity is drastically lower than the constitutive CMV promoter.

Most recently Latham et al. (2000) had achieved a modest four-fold increased in the activity of PSA promoter and enhancer by duplicating a 1455-bp PSA enhancer sequence (−322 to −3869) (E2-PSA) compared to the construct with the enhancer duplication. This enhanced promoter construct appeared to mediate proper tissue-specific nitroreductase protein expression in an adenovector construct as evaluated by infecting cultured cells.

The constructs of the present invention, PSE-BC and PSE-BAC, mediated significantly higher (20 to 60 fold) activity over the native PSE construct. In contrast, the E2-PSA construct of Latham et al. provided only 4-fold increase over its corresponding native E1 construct.

In an adenovector construct, again the present invention construct, PSE-BC, had at least 12-fold higher activity than the corresponding PSE-B Ad construct. Based on transfection studies the PSE-BAC vectors displayed similar efficacies, when compared to their corresponding wildtype sequences.

4.6 Gene Delivery Vectors

Figure 1A:
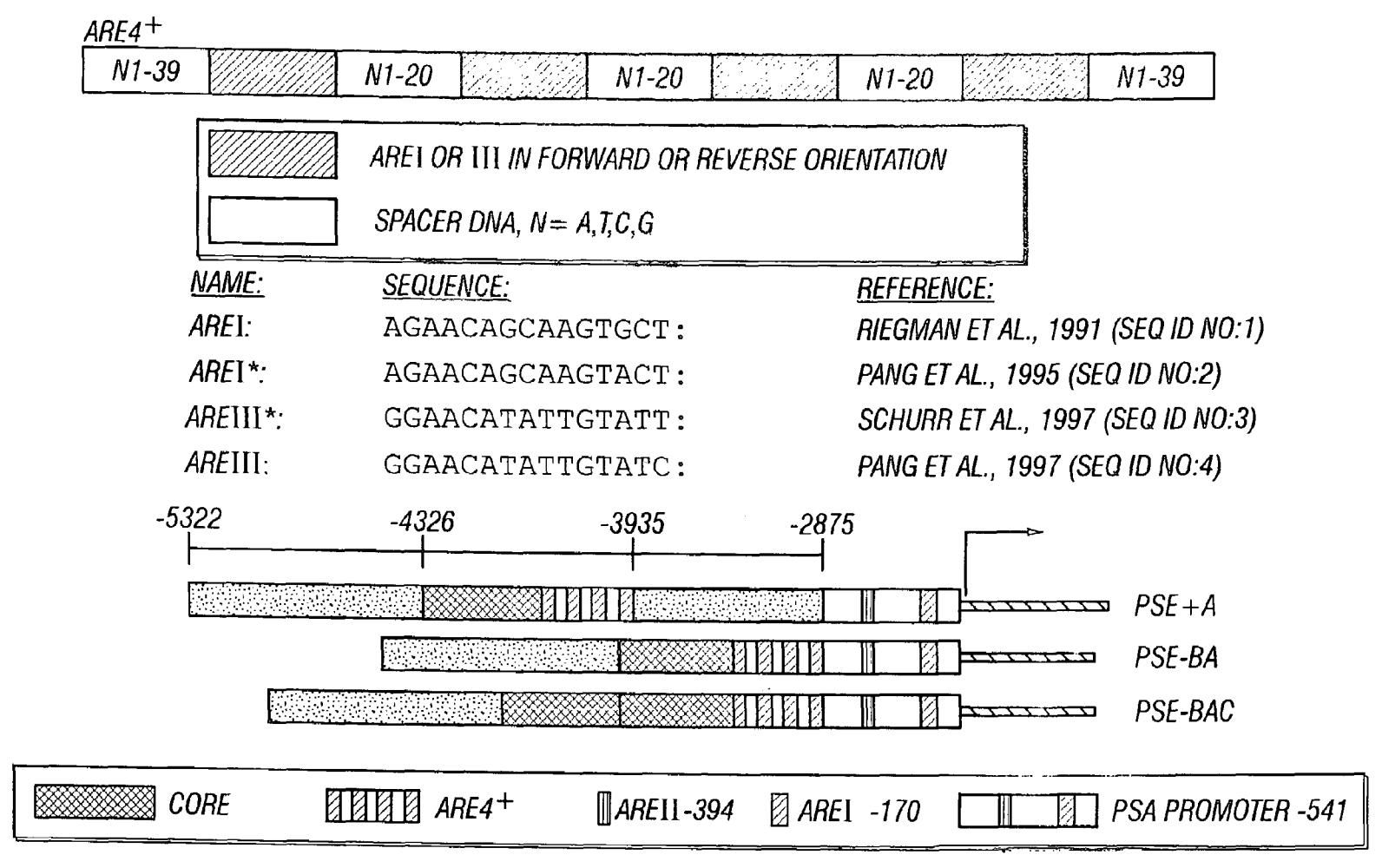
Figure 1B:
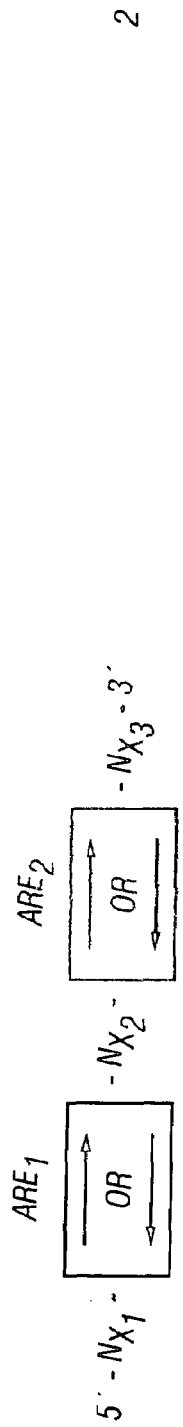
Figure 1B:
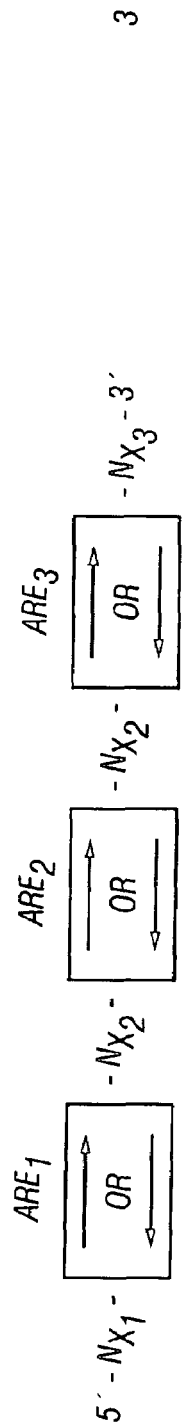
Figure 1B:
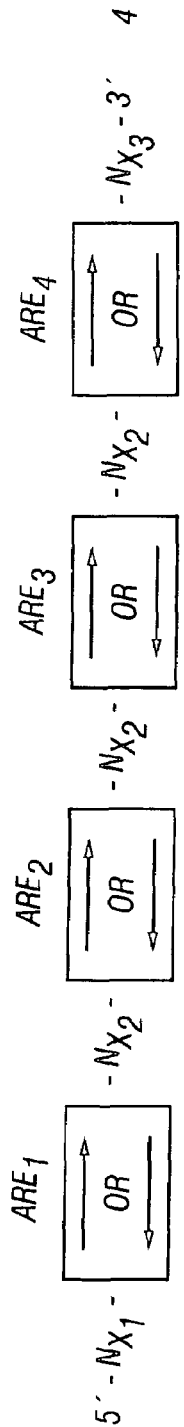
Figure 2:
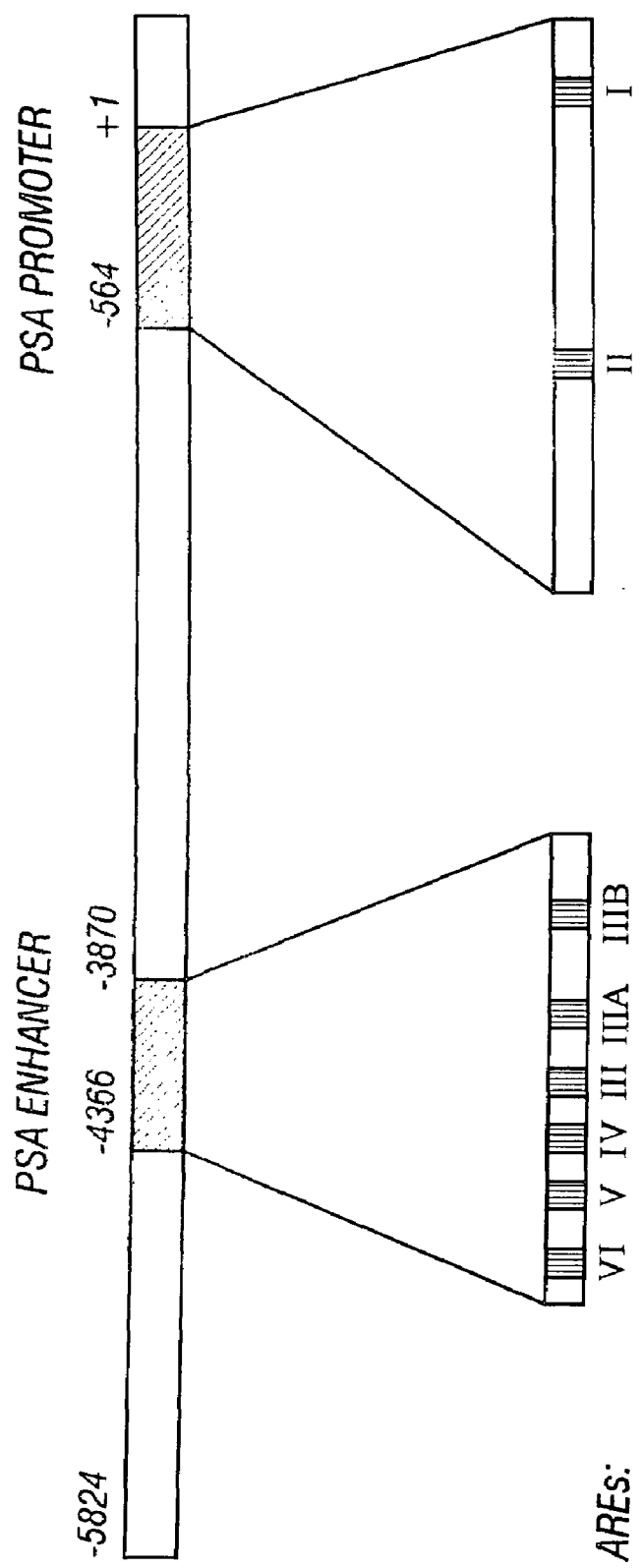
FIG. 2 is a schematic of the regulatory region of the PSA gene.
Figure 3:
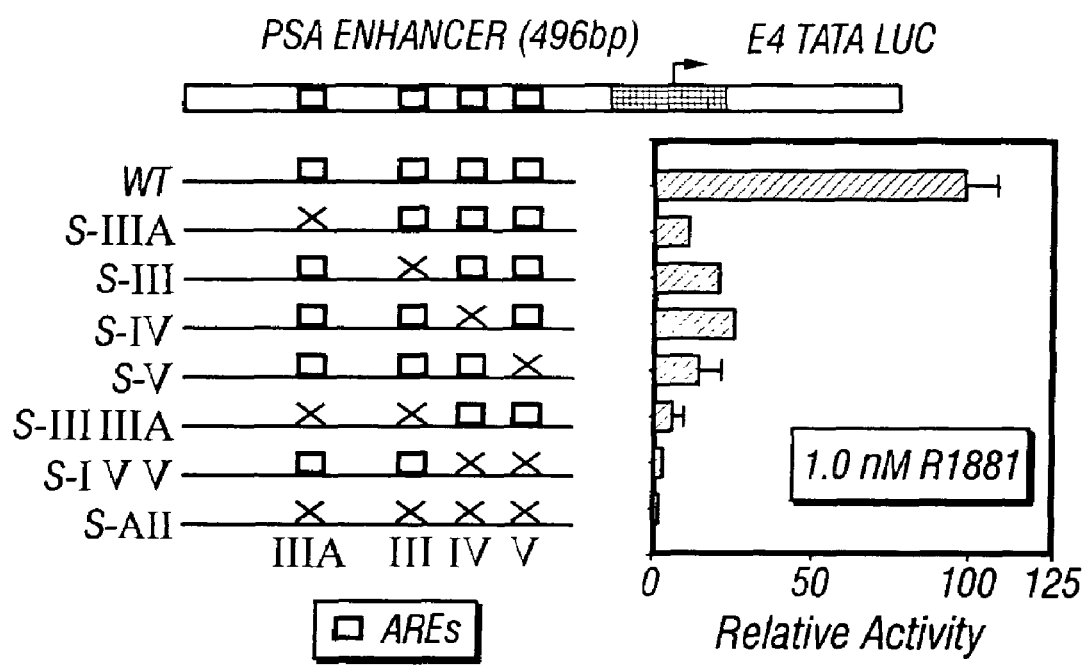
FIG. 3 is a schematic illustrating that the AREs in the PSA enhancer synergistically stimulate transcription.

Among the currently available vectors, first generation E1 and E3 deleted adenovector (Ad) is the most popular for cancer treatment. Its dominant role, as reflected in on-going clinical trials (NCI CancerNet), stems from the ease of large-scale production and genetic manipulation (Hitt et al., 1995). More importantly, Ad seems better suited for in vivo cancer gene therapy than retroviral vector because it can efficiently infect a broad spectrum of cell types, even non-dividing ones. Use of Ad for the relative slow-growing prostate cancer is logical. At least 3 on-going prostate cancer clinical trials utilize Ad (Alemany et al., 1999). Several pre-clinical studies (Lu et al., 1999) have documented efficient in vivo Ad mediated gene transfer into prostate tissue or tumor (see FIG. 1). Moreover, recombinant Ad capable of tissue specific expression in liver, smooth muscle, neuron, breast tissue and prostate cells have been generated (Pastore et al., 1999; Kim et al., 1997; Anderson et al., 1999; Gotoh et al., 1998; Navarro et al., 1999). Use of a gutless Ad (ΔAd) with all viral coding sequences removed (Parks et al., 1996; Hardy et al., 1997; Schiedner et al., 1998; Lieber et al., 1996) will further improve the safety and utility of the vector. Comparing to the first generation vector, these ΔAd mediate prolonged expression by minimizing in vivo antiviral immune responses (Pastore et al., 1999; Schiedner et al., 1998) and allow expanded spaces, >30 kb, for multiple transgenes and regulatory regions. Data indicate that use of tissue specific promoters to express a transgene provides synergy to vector improvements in further diminishing immune clearance of vector mediated gene transfer (Pastore et al., 1999; Kim et al., 1997; Jooss et al., 1998; Morsy et al., 1998). ΔAd with prostate-specific promoter-controlled transgene expression appears to be the most appropriate vector for prostate cancer, as it should mediate both efficient and specific gene expression with minimal viral induced antigenicity.

4.7 Transcriptional Targeting with Prostate Specific Promoters Restrict Therapeutic Transgene Expression to Target Tissue The regulatory regions of prostate specific antigen (PSA) gene are prime candidates to direct prostate-specific expression given their strong tissue-specificity (Schuur et al., 1996, Cleutjens et al., 1997a; Pang et al., 1997) and documented activity in transgenic mice (Cleutjens et al., 1997b; Wei et al., 1997). Normal, hyperplastic and malignant prostate epithelia (Deguchi et al., 1993) specifically express PSA, of which the serum level is widely used clinically as a marker for diagnosis and management of prostate cancer (Catalona et al., 1991; Young et al., 1992). The PSA promoter, a region about 600 bp upstream of transcription initiation, processes some prostate specificity in vitro (Pang et al., 1995; Cleutjens et al., 1996), but it is insufficient to direct prostate specific expression (Cleutjens et al., 1997b) in transgenic mice. An enhancer, located approximately 4-kb upstream, when fused to the PSA promoter, confers not only dramatic androgen inducibility, but also a high level of prostate specificity (Schuur et al., 1996; Cleutjens et al., 1997a; Pang et al., 1997; Zhang et al., 1997a; Zhang et al., 1997b).

The PSA regulatory regions have been utilized in Ad to direct prostate-specific expression of cytotoxic HSV TK (Gotoh et al., 1998) or viral E1A (Rodriguez et al., 1997) to induce lytic viral replication. The prostate specific transcription mediated by the 5.8-kb or 2.9-kb PSA regulatory region was not directly evaluated, nor was the tissue specificity or safety of in vivo administration investigated. However, compared to plasmid transfections both Ad appeared to exert reduced discriminatory expression in permissive cells (i.e., PSA producing cells) over non-permissive cells. The Ad-PSA-TK expressed TK enzyme in LNCaP cells was approximately 10-fold higher than in non-permissive WH bladder cells and the androgen induction were less than 10-fold (Gotoh et al., 1998). These results are much lower than the usual 100-fold tissue specific discrimination and 1000-fold androgen induction observed in transfection studies (Schuur et al., 1996; Cleutjens et al., 1997a; Pang et al., 1997).

4.8 Modifying the PSE Promoter to Achieve High Level of Expression in Androgen Independent Prostate Cancer Although patients with aggressive AI disease should be the targeted population to develop a new and effective treatment, few good AI prostate cancer models (Wu et al., 1994), especially ones amenable to in vitro manipulation, are available. An important and useful AI model to investigate the mechanism of progression of human prostate cancer (CaP) cells after androgen ablation has been developed. A highly aggressive AI tumor line with distinct cellular and molecular properties, designated CL cell, was selected and expanded from the androgen-dependent (AD) LNCaP cell line by androgen depletion of growth media (Patel et al., 2000). CL cells acquired significant resistance to radiation and to anti-cancer cytotoxic agents (Taxol, Vinblastine, and Etoposide). In contrast to the poorly tumorigenic parental LNCaP cells, CL lines proved highly tumorigenic, exhibiting invasive and metastatic characteristics in male or female mice within a short period of 3-4 weeks without any growth supplements (e.g., Matrigel). The aggressive dissemination pattern is elegantly demonstrated by the CL1-GFP clone that stably expresses marker GFP. CL cells thus provide an excellent AI CaP tumor model for the development of new AI prostate specific promoters.

Expression of androgen responsive gene such as PSA is regulated by binding of ligand-activated AR to AREs in the regulatory region. Both the PSA promoter and enhancer contain AREs (Schuur et al., 1996; Cleutjens et al., 1997a; Pang et al., 1997; Pang et al., 1995; Cleutjens et al., 1996; Zhang et al., 1997a; Zhang et al., 1997b). AR binds to multiple AREs in a cooperative manner and contributes greatly to the activity of PSA enhancer core (Huang et al., 1999). Most AI prostate tumors can continue to express the androgen- and AR-dependent PSA gene despite being androgen-depleted. Several investigations have focused on alterations in AR level or function as a mechanism of altered regulation in AI stage (Taplin et al., 1995; Gaddipati et al., 1994; Koivisto et al., 1997a; 1997b), which appeared to account for a minority of cases. Recent reports indicated that androgen-independent activation of AR function can be achieved by over expression of HER-2/neu (Craft et al., 1999), indicating modulation of AR function by other signaling pathways (Sadar, 1999). HER-2/neu mRNA expression is slightly up-regulated in CL cells when compared to LNCaP cells.

Recently, a novel prostate specific Ets-family transcription factor, PDEF, was isolated (Oettgen et al., 2000). It binds to a GGAT specific sequence element, and several sites exist in the PSA enhancer region. PDEF can activate PSA promoter activity in the absence of androgen and AR, but it can also interact with AR to enhance androgen-mediated activation of PSA promoter. PDEF expression is retained in CL cells.

4.9 Pharmaceutical Compositions

In certain embodiments, the present invention concerns formulation of one or more of the polynucleotide compositions disclosed herein in pharmaceutically acceptable solutions for administration to a cell or an animal, either alone, or in combination with one or more other modalities of anti-cancer therapy.

It will also be understood that, if desired, the nucleic acid segment, RNA, or DNA compositions disclosed herein may be administered in combination with other agents as well, such as, e.g., proteins or polypeptides or various pharmaceutically-active agents. As long as the composition comprises at least one of the genetic expression constructs disclosed herein, there is virtually no limit to other components that may also be included, given that the additional agents do not cause a significant adverse effect upon contact with the target cells or host tissues. The RNA- or DNA-derived compositions may thus be delivered along with various other agents as required in the particular instance. Such RNA or DNA compositions may be purified from host cells or other biological sources, or alternatively may be chemically synthesized as described herein. Likewise, such compositions may comprise substituted or derivatized RNA or DNA compositions. Such compositions may include one or more therapeutic gene constructs, either alone, or in combination with one or more modified peptide or nucleic acid substituent derivatives, and/or other anticancer therapeutics.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, intravenous, intraprostatic, intratumoral, intramuscular administration and formulation.

4.9.1 Injectable Delivery

For example, the pharmaceutical compositions disclosed herein may be administered parenterally, intravenously, intramuscularly, or even intraperitoneally as described in U.S. Pat. No. 5,543,158, U.S. Pat. No. 5,641,515 and U.S. Pat. No. 5,399,363 (each specifically incorporated herein by reference in its entirety). Solutions of the active compounds as free-base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, Hoover, 1975). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions may be prepared by incorporating the gene therapy constructs in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The polynucleotide compositions disclosed herein may be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

4.9.2 Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the polynucleotide compositions of the present invention into suitable host cells. In particular, the polynucleotide compositions of the present invention may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-lives (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567, 434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars, and drugs.

Alternatively, the invention provides for pharmaceutically acceptable nanocapsule formulations of the polynucleotide compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1980; 1988; zur Muhlen et al., 1998; Zambaux et al. 1998; Pinto-Alphandry et al., 1995 and U.S. Pat. No. 5,145, 684, specifically incorporated herein by reference in its entirety). In particular, methods of polynucleotide delivery to a target cell using either nanoparticles or nanospheres (Schwab et al., 1994; Truong-Le et al., 1998) are also particularly contemplated to be useful in formulating the disclosed compositions for administration to an animal, and to a human in particular.

4.10 Therapeutic and Diagnostic Kits

The invention also provides one or more of the prostate-specific gene expression constructs formulated with one or more pharmaceutically acceptable excipients, carriers, diluents, adjuvants, and/or other components for administration to an animal in need thereof. In addition to the disclosed gene constructs, additional anticancer agents, polynucleotides, peptides, antigens, or other therapeutic compounds as may be employed in the formulation of particular polynucleotide or vector formulations, and in the preparation of anticancer agents or prostate therapies for administration to the affected mammal.

As such, preferred animals for administration of the pharmaceutical compositions disclosed herein include mammals, and particularly humans. Other preferred animals include primates, sheep, goats, bovines, equines, porcines, lupines, canines, and felines, as well as any other mammalian species commonly considered pets, livestock, or commercially relevant species. The composition may include partially or significantly purified polynucleotide compositions, either alone, or in combination with one or more additional active ingredients, which may be obtained from natural or recombinant sources, or which may be obtainable naturally or either chemically synthesized, or alternatively produced in vitro from recombinant host cells expressing nucleic acid segments encoding such additional active ingredients.

Therapeutic kits may also be prepared that comprise at least one of the polynucleotide disclosed herein and instructions for using the composition as a therapeutic agent. The container means for such kits may typically comprise at least one vial, test tube, flask, bottle, syringe or other container means, into which the polynucleotide composition(s) may be placed, and preferably suitably aliquoted. Where a second anticancer agent is also provided, the kit may also contain a second distinct container means into which this second composition may be placed. Alternatively, the plurality of anticancer compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained. Where a radiolabel or fluorogenic label or other such detecting means is included within the kit, the labeling agent may be provided either in the same container as the polynucleotide composition, or may alternatively be placed in a second distinct container means into which this second composition may be placed and suitably aliquoted. Alternatively, the polynucleotide composition and the label may be prepared in a single container means, and in most cases, the kit will also typically include a means for containing the vial(s) in close confinement for commercial sale and/or convenient packaging and delivery.

4.11 Methods of Nucleic Acid Delivery and DNA Transfection

In certain embodiments, it is contemplated that one or more RNA or DNA and/or substituted polynucleotide compositions disclosed herein will be used to transfect an appropriate host cell. Technology for introduction of RNAs and DNAs, and vectors comprising them into suitable host cells is well known to those of skill in the art.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984; Suzuki et al., 1998; Vanbever et al., 1998), direct microinjection (Capecchi, 1980; Harland and Weintraub, 1985), DNA-loaded liposomes (Nicolau and Sene, 1982; Fraley et al., 1979; Takakura, 1998) and lipofectamine-DNA complexes, cell sonication (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

A bacterial cell, a yeast cell, or an animal cell transformed with one or more of the disclosed expression vectors represent an important aspect of the present invention. Such transformed host cells are often desirable for use in the expression of the various DNA gene constructs disclosed herein. In some aspects of the invention, it is often desirable to modulate, regulate, or otherwise control the expression of the gene segments disclosed herein. Such methods are routine to those of skill in the molecular genetic arts. Typically, when increased or over-expression of a particular gene is desired, various manipulations may be employed for enhancing the expression of the messenger RNA, particularly by using an active promoter, and in particular, a tissue-specific promoter such as those disclosed herein, as well as by employing sequences, which enhance the stability of the messenger RNA in the particular transformed host cell.

Typically, the initiation and translational termination region will involve stop codon(s), a terminator region, and optionally, a polyadenylation signal. In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism or eukaryotic host, but will usually be included with a DNA sequence involving a marker, where the second DNA sequence may be joined to the expression construct during introduction of the DNA into the host.

Where no functional replication system is present, the construct will also preferably include a sequence of at least about 40 or 50 basepairs (bp) or so, preferably at least about 90 to about 100 or so bp, and usually not more than about 500 to about 1000 or so bp of a sequence homologous with a sequence in the host. In this way, the probability of legitimate recombination is enhanced, so that the gene will be integrated into the host and stably maintained by the host. Desirably, the regulatory regions of the expression construct will be in close proximity to (and also operably positioned relative to) the selected therapeutic gene providing for complementation as well as the gene providing for the competitive advantage. Therefore, in the event that the therapeutic gene is lost, the resulting organism will be likely to also lose the gene providing for the competitive advantage, so that it will be unable to compete in the environment with the gene retaining the intact construct.

The selected therapeutic gene can be introduced between the transcriptional and translational initiation region and the transcriptional and translational termination region, so as to be under the regulatory control of the initiation region. This construct may be included in a plasmid, which will include at least one replication system, but may include more than one, where one replication system is employed for cloning during the development of the plasmid and the second replication system is necessary for functioning in the ultimate host, in this case, a mammalian host cell. In addition, one or more markers may be present, which have been described previously. Where integration is desired, the plasmid will desirably include a sequence homologous with the host genome.

Genes or other nucleic acid segments, as disclosed herein, can be inserted into host cells using a variety of techniques that are well known in the art. Five general methods for delivering a nucleic segment into cells have been described: (1) chemical methods (Graham and VanDerEb, 1973); (2) physical methods such as microinjection (Capecchi, 1980), electroporation (U.S. Pat. No. 5,472,869; Wong and Neumann, 1982; Fromm et al., 1985), microprojectile bombardment (U.S. Pat. No. 5,874,265, specifically incorporated herein by reference in its entirety), "gene gun" (Yang et al., 1990); (3) viral vectors (Eglitis and Anderson, 1988); (4) receptor-mediated mechanisms (Curiel et al., 1991; Wagner et al., 1992); and (5) bacterial-mediated transformation.

For example, a large number of cloning vectors comprising a replication system in *E. coli* and a marker that permits selection of the transformed cells are available for preparation for the insertion of foreign genes into higher organisms, including animals. The vectors comprise, for example, plasmids (such as pBR322, pUC series, M13mp series, pACYC184, etc), cosmids, phage, and/or phagemids and the like. Accordingly, the disclosed polynucleotides can be inserted into a given vector at a suitable restriction site. The resulting plasmid may be used, for example, to transform bacterial cells such as *E. coli*. The bacterial cells are then cultivated in a suitable nutrient medium, harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the host cells and tissues, other DNA sequences may be necessary.

4.11.1 Electroporation

The application of brief, high-voltage electric pulses to a variety of animal cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by electroporation is well-known to those of skill in the art (see e.g., U.S. Pat. No. 5,324,253, specifically incorporated herein by reference in its entirety). In this method, certain cell wall-degrading enzymes, are employed to render the target recipient cells more susceptible to transformation by electroporation than untreated cells. Alternatively, recipient cells are made more susceptible to transformation, by mechanical wounding. One would partially degrade the cell walls of the chosen cells by exposing them to cell membrane degrading enzymes or mechanically wounding in a controlled manner. Such cells would then be the recipient of DNA transfer by electroporation, which may be carried out at this stage, and transformed cells then identified by a suitable selection or screening protocol dependent on the nature of the newly incorporated DNA.

4.11.2 Microprojectile Bombardment

A further advantageous method for delivering transforming DNA segments to suitable host cells and tissues is microprojectile bombardment. In this method, particles may be coated with nucleic acids and delivered into cells by a propelling force. Exemplary particles include those comprised of tungsten, gold, platinum, and the like.

An illustrative embodiment of a method for delivering DNA into host cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust several of the bombardment parameters in small-scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.12 Expression Vectors

The present invention contemplates an expression vector comprising at least one prostate-specific genetic expression construct of the present invention. Thus, in one embodiment an expression vector is constructed with a specific DNA molecule orientated such that one or more of the disclosed promoter/enhancer constructs is operatively linked to the molecule to direct the expression of the selected DNA molecule in a suitable host cell.

As used herein, the term "operatively linked" means that a promoter is connected to a functional DNA in such a way that the transcription of that functional DNA is controlled and regulated by that promoter. Means for operatively linking a promoter to a functional DNA are well known in the art. Preferably the DNA segment operably positioned under the control of the genetic expression element encodes one or more therapeutic polypeptides whose expression in prostate cells in a tissue-specific manner confers to the cells a therapeutic benefit.

The choice of which expression vector and ultimately to which promoter a polypeptide coding region is operatively linked depend directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the therapeutic gene when it is operably linked to the prostate-specific genetic expression construct disclosed herein.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.13 In Vivo Delivery and Treatment Protocols

When it is desirable to employ the disclosed genetic constructs in therapeutic regimens, it is necessary to administer them in pharmaceutical formulations using one or more of the conventional methods of polynucleotide delivery to animal cells. To introduce the polynucleotide constructs to cells in vivo, one of any number of conventional ways may be employed. These methods include the viral-mediated delivery methods described above that utilize retroviral, adenoviral, or adeno-associated viral vectors, which are well known to those of skill in the gene therapy arts.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

AAV (Ridgeway, 1988; Hermonat and Muzyczka, 1984) is a parvovirus, discovered as a contamination of adenoviral stocks. It is a ubiquitous virus (antibodies are present in 85% of the U.S. human population) that has not been linked to any disease. It is also classified as a dependovirus, because its replication is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene encodes proteins responsible for viral replications, whereas the cap gene encodes the capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

Other viral vectors may also be employed as expression constructs in the present invention for the delivery of selected therapeutic polynucleotide sequences to a host cell. Vectors derived from viruses such as vaccinia virus (Ridgeway, 1988; Coupar et al., 1988), lentiviruses, polioviruses and herpesviruses may be employed. They offer several attractive features for various mammalian cells (Friedmann, 1989; Ridgeway, 1988; Coupar et al., 1988; Horwich et al., 1990).

In order to effect prostate-specific expression of the polynucleotide sequences of the present invention, the expression construct must be delivered into a cell. This delivery may be accomplished in vitro, as in laboratory procedures for transforming cells lines, or in vivo or ex vivo, as in the treatment of certain disease states, and in particular, in the treatment of prostate cancers and related hyperproliferative disorders of the prostate. As described above, the preferred mechanism for delivery is via viral infection where the expression construct is encapsidated in an infectious viral particle.

Once the expression construct has been delivered into the cell the polynucleotide sequences may be positioned and expressed at different sites. In certain embodiments, the nucleic acid encoding the polynucleotide construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct comprising one or more therapeutic polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

In a further embodiment of the invention, the expression construct may be entrapped in one or more nanocapsules, liposomes, or other lipid based DNA delivery agent. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures, and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs that may be employed to deliver a polynucleotide into a target cell include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Eur. Pat. Appl. Publ. No. EP0273085, specifically incorporated herein by reference in its entirety).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

4.14 Transformed Animal Cells and Transgenic Non-Human Animals

In one embodiment, the invention provides a transgenic non-human animal having incorporated into its genome a transgene that encodes a selected heterologous polypeptide operably positioned under the transcriptional control of the PSA promoter and the prostate-specific enhancer elements disclosed herein. A further aspect of the invention is a transgenic non-human animal having incorporated into its genome a transgene that encodes such a heterologous polypeptide. Other embodiments of the invention also concern the progeny of such a transgenic animal, as well as subsequent generation offspring derived from such a transgenic animal.

The invention also discloses and claims host cells, both native, and genetically engineered, which express one or more genes encoding all or substantially all of a heterologous polypeptide to produce the encoded polypeptide(s) in a suitably transformed host cell, and in particular, in a transformed animal cell, and ultimately, in one or more cells of a transgenic animal.

In yet another aspect, the present invention provides methods for producing a transgenic animal that expresses one or more of the genetic constructs described herein. The process of preparing transgenic animals once a particular genetic construct is obtained is generally a straightforward process. In general, the method comprises transforming a suitable host cell with one or more nucleic acid segments, vectors, virus, or genetic expression constructs that contains at least a first prostate-specific enhancer element, and a first prostate-specific promoter operatively linked to at least a first coding region that encodes one or more selected heterologous polypeptides, peptides, or ribozymes. In some embodiments, the coding region may further be operatively linked to one or more transcription-terminating region(s), whereby the promoter is capable of driving the transcription of the coding region in the cell, and hence providing the cell the ability to produce the recombinant polypeptide in vivo.

Alternatively, in instances where it is desirable to control, regulate, or decrease the amount of a particular recombinant protein expressed in a particular transgenic cell, the invention also provides for the expression of an antisense oligonucleotide or other nucleic acid sequences that are complementary to the mRNA that encodes the expressed polypeptide. The use of antisense mRNA as a means of controlling or decreasing the amount of a given protein of interest in a cell is well known in the art. The use of antisense constructs are particularly contemplated to be useful in the reduction of mRNAs that encode a polypeptide that causes, exacerbates, or controls, hyperproliferation of prostate cells, or leads to one or more disorders of the prostate, including prostatic hyperplasia and prostatic neoplasia.

As used herein, the term "transgenic animal" is intended to refer to a non-human animal that has incorporated DNA sequences, including but not limited to genes which are perhaps not normally present, DNA sequences not normally transcribed into RNA or translated into a polypeptide ("expressed"), or any other genes or DNA sequences which one desires to introduce into the non-transformed animal, such as genes which may normally be present in the non-transformed animal but which one desires to either genetically engineer or to have altered expression.

It is contemplated that in some instances the genome of a transgenic animal of the present invention will have been augmented through the stable introduction of one or more transgenes, either native, synthetically modified, or mutated. In some instances, more than one transgene will be incorporated into the genome of the transformed host animal cell. Such is the case when more than one DNA segment is incorporated into the genome of such an animal. In certain situations, it may be desirable to have one, two, three, four, or even more heterologous proteins (either native or recombinantly-engineered) incorporated and stably expressed in the transformed transgenic animal.

Such transgenic animals may be desirable for the production of heterologous polypeptides in selected animal species.

5.0 EXAMPLES

The following examples are included to demonstrate preferred embodiments of the invention. However, those of skill in the art should, in light of the present disclosure, appreciate that many changes can be made in the specific embodiments which are disclosed and still obtain a like or similar result without departing from the spirit and scope of the invention described in the appended claims.

5.1 Example 1—Construction of the ARE4 Enhancer Element

In one embodiment, the invention concerns the creation of an artificial enhancer sequence. One such sequence is the ARE4 synthetic 160-bp regulatory element containing 4 tandem copies of ARE sequence was derived from the AREI element of PSA promoter located at −170 (shown in FIG. 1C; SEQ ID NO:5).

5.2 Example 2—Cooperative Assembly of Androgen Receptor into a Nucleoprotein Complex that Regulates the Prostate-Specific Antigen Enhancer

5.2.1 Experimental Procedures

5.2.1.1 Plasmids pET11dHis$_6$ARDBD was constructed by insertion of a polymerase chain reaction (PCR™) DNA fragment, encoding the DNA binding domain of human AR, from amino acids 549-650, into the BamHI site of pET11dHis$_6$heart muscle kinase (provided by R. Hori). The construct generated a 127-amino acid protein with a His$_6$ tag on the amino terminus and heart muscle kinase phosphorylation site on the carboxyl terminus.

The wild-type PSA enhancer-E4CAT reporter vector was constructed by PCR™ subcloning a 496-bp PSA enhancer region from the 2.4-kb enhancer described by Belldegrun and colleagues (Pang et al., 1997) in reverse orientation into HindIII/XbaI sites upstream of E4 TATA box of pE4TCAT (Emami and Carey, 1992). The PSA enhancer-E4LUC reporter vector was constructed by PCR™ amplification and subcloning of the PSA enhancer-E4 TATA region (up to +38) into SacI/XhoI sites of pGL3-Basic vector (Promega). All constructs were sequenced to confirm their integrity. The constructs contained several notable point mutations vs the published sequence by Henderson and colleagues. These point mutations were present in the original sequence and were not introduced inadvertently by PCR™. The DNA sequence of ARE III, −4150 GGAAGAtatTGTATC −4136 (SEQ ID NO:7), was altered to GGAACAtatTGTTATT (SEQ ID NO:8), a change that brings the sequence into better alignment with the ARE consensus. Furthermore, the sequence of ARE VI, −4303 GGATGCtgtGCAGAA −4289 (SEQ ID NO:9), was altered to GGATGCtgtGCACAC (SEQ ID NO:10). Two other mutations outside of identifiable AREs were also detected within this region.

Enhancer mutant vectors were constructed by a two-step overlap PCR™ method where AREs were replaced by GAL4-binding sites and restriction enzyme cleavage sites to conserve phasing of the DNA (below, the replacement sequence is in capitals).

ARE internal replacement primers were constructed as follows:

ARE VI:
5'-CTGCAGCGGAGTACTGTCCTCCGgtttgtgccactggtgag-3' (SEQ ID NO:11) and 5'-CGGAGGACAGTACTCCGCTGCAGgactgctctggtcaccct-3' (SEQ ID NO:12);

ARE V:
5'-GTCGACGGAGTACTGTCCTCCGcctgctcagcctttgtc-3', (SEQ ID NO:13) 5'-CGGAGGACAGTACTCCGTCGACgattgaggattcctaatc-3' (SEQ ID NO:14), 5'-actgTTCAaacttgcaaacctgc-3' (SEQ ID NO:15), 5'-gcaggtttgcaagttTGAAcagt-3' (SEQ ID NO:16), 5'-actgggacGGACtgcaaacctgc-3' (SEQ ID NO:17), 5'-gcaggtttgcaGTCCgtcccagt-3' (SEQ ID NO:18), 5'-actgggacaacttgcGGGActgc-3' (SEQ ID NO:19), and 5'-gcagTCCCgcaagttgtcccagt-3' (SEQ ID NO:20).

ARE IV:
5'-GTCGACGTCGACCGGAGTACTGTCCTCCGTCGACgaaaacagacctactct-3' (SEQ ID NO:21) and
5'-GTCGACGGAGGACAGTACTCCGGTCGACGTCGACgacaaaggctgagcagg-3' (SEQ ID NO:22);

ARE III:
5'-CGGAGTACTGTCCTCCGattgtccttgacagtaaac-3' (SEQ ID NO:23) and 5'-CGGAGGACAGTACTCCGccagagtaggtctgtttc-3' (SEQ ID NO:24);

ARE IIIA:
5'-CTGCAGCGGAGTACTGTCCTCCGctgagagagatatcatct-3' (SEQ ID NO:25) and 5'-CGGAGGACAGTACTCCGCTGCAGgataataaagataatgtc-3' (SEQ ID NO:26);

ARE IIIB:
5'-CTGCAGCGGAGTACTGTCCTCCGacgtgacagaaccatgga-3' (SEQ ID NO:27) and 5'-CGGAGGACAGTACTCCGCTGCAGacagcaacaccttttttt-3' (SEQ ID NO:28).

FLAG-tagged AR was constructed in two steps. In the first step a primer encoding the FLAG peptide fused to the sequences encoding the amino-terminal 5 amino acids of AR (5'-GCTCTAGACCACCATGGACTACAAGGAC-GACGACGACAAGGCCGAAGTGCAGTTA GGGC-3' (SEQ ID NO:29)) was used in combination with an internal AR primer (5'-CCCTCTAGACGGCCGAGGGTAGAC-CCT-3' (SEQ ID NO:30), encoding amino acids 9-14), to obtain a DNA fragment from amino acids 1-14 of AR. This fragment was digested with XbaI and inserted into the XbaI site of pBluescriptKS (Stratagene). The resulting plasmid was digested with EagI, and an EagI fragment of the AR cDNA, encoding the remaining sequences from amino acids 10-919, was cloned in. The FLAG-tagged full-length AR (fAR) cDNA was then excised from the pBluescriptKS vector by XbaI digestion and placed into the XbaI site of pSRα (Sawyers et al., 1992) to generate pSRαfAR.

5.2.1.2 ARDBD Purification

The *Escherichia coli* strain BL21(DE3) was transformed with pET11dHis$_6$ARDBD. 0.1 liter of cells was grown to an $A_{600}$ of 0.6 and induced with 0.5 mM isopropyl-1-thio-β-D-galactopyranoside and 10 μM ZnCl$_2$ for 3 h. After harvesting, cells were resuspended in 5 ml of Buffer A (20 mM HEPES, pH 7.9, 20% glycerol, 10 μM ZnCl$_2$, 0.5 mM phenylmethylsulfonyl fluoride) containing 0.1 M KCl and lysed by sonication. The supernatant was incubated with 1.5 ml of Ni-NTA-agarose (Qiagen) resin in batch, rocked gently for 30 min at 4° C., and then loaded on to a small Bio-Rad Econo-column. After successively washing the resin with 15 ml of Buffer A containing 0.1 M KCl, and 15 ml of Buffer A containing 0.1 M KCl and 20 mM imidazole, ARDBD was eluted with Buffer A containing 0.1 M KCl and 150 mM imidazole. Peak fractions were combined and loaded onto a 1-ml ARE affinity column prepared by binding 1 mg of a biotinylated ARE containing double-stranded oligonucleotide (5'-tttccttgcAGTACAgcaTGTTCTagc-3' (SEQ ID NO:31) to 1 ml of packed streptavidin beads. The column was washed with 10 ml of Buffer A containing 0.1 M KCl, 10 ml of Buffer A containing 0.5 M KCl, and ARDBD was eluted with Buffer A containing 0.8 M KCl. The fractions were analyzed by SDS-polyacrylamide gel electrophoresis and Coomassie Blue staining. Peak fractions were combined, dialyzed against Buffer D (20 mM HEPES, pH 7.9, 20% glycerol, 0.1 M KCl, 0.2 mM EDTA, 0.5 mM dithiothreitol, 0.5 mM phenylmethylsulfonyl fluoride), and concentrated on Centricon-10 columns. The final preparation contained 100 μg/ml ARDBD.

5.2.1.3 Expression and Purification of Flag-Tagged AR

20 μg of pSRαfAR was transfected with helper virus φ into a 10-cm dish of 293T cells at 50% confluency using calcium phosphate transfection (Muller et al., 1991). One day after transfection, virus was collected in Iscove media containing 10% FBS at 12-h intervals for 48 h. Virus was isolated by filtration of the culture supernatant through a 0.45 μM filter. 2-3 ml of virus supernatant was incubated with HeLa and LNCaP cells at 10-30% confluency (LNCaP cells 20-30%, HeLa cells 10-20%) in the presence of 8 μg/ml Polybrene for 4 h or overnight. 10 ml of medium (DMEM for HeLa cells, RPMI 1640 for LNCaP cells) was added, and cells were passaged for 24 h. 800 μg/ml G418 (Life Technologies, Inc.) was then added. After 2 weeks, individual clones were isolated and expanded, and levels of expression were compared by immunoblotting with FLAG monoclonal antibodies (Sigma). The clone expressing the highest level of fAR was chosen for large-scale preparation.

Nuclear extracts from both HeLa and LNCaP cells expressing fAR were prepared as described previously (Dignam et al., 1983). Although the scale of the purification varied among the different preparations, on average, 1 ml of nuclear extract was incubated with 20 μl of agarose beads conjugated with FLAG monoclonal antibodies (Sigma) at 4° C. for 6 h. The beads were washed three times with 0.5 ml of Buffer D containing 0.3 M KCl, 0.05% Nonidet P-40, 0.5 mM phenylmethylsulfonyl fluoride, and 0.5 mM dithiothreitol and eluted twice, 20 min each, with 20 μl of Buffer D containing 0.2 mg/ml FLAG peptide (Eastman Kodak Co.).

5.2.1.3 Western Blotting

Immunoblotting was performed according to standard procedures. Briefly, proteins were separated on a 12% SDS-polyacrylamide gel and transferred to a Hybond C Extra membrane (Amersham Pharmacia Biotech). The membrane was blocked with phosphate-buffered saline containing 5% nonfat milk for 30 min, incubated sequentially with primary and secondary antibodies for 30 min each, and then developed using ECL reagents from Amersham Pharmacia Biotech. Antibodies against the amino terminus of AR were purchased from Santa Cruz Biotechnology. Monoclonal antibodies against the FLAG tag of AR were purchased from Kodak through Sigma. Secondary rabbit and mouse antibodies were from Bio-Rad.

5.2.1.4 DNase I Footprinting

The binding reactions for DNase I footprinting were as described previously (Chi et al., 1995). Indicated amounts of recombinant AR DNA binding domain (ARDBD), FLAG-tagged AR, and crude nuclear extracts from f-LNCaP cells were incubated in 13 μl of buffer containing 12.5 mM HEPES, pH 7.9, 12.5% glycerol, 5 mM MgCl$_2$, 70 mM KCl, 0.2 mM EDTA, 60 mM mercaptoethanol, 0.5 mg/ml bovine serum albumin, and 200 ng of poly(dG-dC). After 45 min at 30° C., DNase I was added to the reactions. The cleavage reactions were terminated after 1 min by addition of 100 μl of stop buffer containing 400 mM sodium acetate, pH 5.2, 0.2% SDS, 10 mM EDTA, 50 μg/ml yeast tRNA, and 100 μg/ml proteinase K. The mixtures were incubated at 50° C. for 15 min, extracted with phenol/chloroform, and the products precipitated with ethanol. Precipitates were dissolved in formamide loading buffer and analyzed on 8% polyacrylamide/urea sequencing gels. The cleavage ladders were visualized by exposure to XAR-5 film or by PhosphorImager analysis.

5.2.1.5 Cell Culture and Transfections

BHK 21 cells were grown in DMEM (Life Technologies, Inc.) supplemented with 10% FBS, L-glutamine, and antibiotics (penicillin/streptomycin). $2.5 \times 10^5$ cells per well were plated into 6-well plates in phenol red-free DMEM (Mediatech) supplemented with 10% charcoal/dextran-treated FBS (Omega Scientific) 24 h prior to transfections. Transfection of BHK 21 cells was performed using the calcium phosphate method or Tfx-10 reagent (Promega). 200 ng of reporter plasmid and 50 ng of CMV-AR or CMV-PR were used in transfections. AR and PR were induced with 1 nM R1881 and 10 nM progesterone, respectively. 48 h after transfection, the cells were harvested and CAT or luciferase assays were performed according to standard procedures.

LNCaP cells were grown in RPMI 1640 (Life Technologies, Inc.) supplemented with 10% FBS, L-glutamine, and antibiotics (penicillin/streptomycin). $2.5 \times 10^5$ cells per well were plated into 6-well plates 24 h prior to transfections. At this point, the cells were in phenol red-free RPMI 1640 (Mediatech) supplemented with 10% charcoal/dextran-treated FBS (Omega Scientific), L-glutamine, and antibiotics. LNCaP cells were transfected using Tfx-50 reagent (Promega). 200 ng of reporter plasmid was used in transfections. After 48 h, reporter gene expression was determined using a luciferase assay kit (Promega).

5.2.2 Results

5.2.2.1 The Enhancer Region

To understand the molecular basis for the androgen responsiveness of the core PSA enhancer, a 496-bp DNA fragment bearing the minimal 455-bp minimal enhancer (Cleutjens, 1997a) was amplified by PCR™, confirmed by DNA sequencing, and cloned upstream of the adenovirus E4 core promoter (−38 to +38) fused to either CAT or luciferase reporters. The E4 reporter was used in transfection studies because it is highly inducible by activators and has been employed in numerous studies to examine the properties of mammalian enhancers (Emami and Carey, 1992). Furthermore, transfection experiments revealed that the E4 promoter alone did not respond to AR in the absence of upstream AREs. The resulting PSA-E4 template was employed both in DNA binding analyses with recombinant AR and in transfection studies with endogenous AR or AR expressed from the CMV enhancer/promoter.

5.2.2.2 Identification of a cluster of low affinity AREs in the PSA Enhancer The enhancer region was first subjected to DNase I footprinting analysis using the AR DNA binding domain (ARDBD), amino acids 549-650. The ARDBD was expressed as a $His_6$ fusion protein from a modified pET11d (Novagen) T7 expression vector in E. coli. The E. coli lysate was bound to a Ni-NTA resin, and ARDBD was eluted with imidazole as described. To purify active ARDBD away from inactive protein, the Ni-NTA eluate was subjected to an ARE-DNA affinity column chromatography. The final protein was >95% homogeneous as measured by Coomassie Blue staining of SDS-polyacrylamide gels.

An initial experimental objective was to confirm the presence of a single published AR-binding site in the PSA enhancer using DNase I footprinting analysis. This site, termed ARE III, is centered at −4200 (Cleutjens, 1997a) or −4143 (Schuur et al., 1996; Zhang et al., 1997a; Zhang et al., 1997b) depending on the numbering system used in different laboratories. The high specific activity of the ARDBD, however, allowed the detection of five additional binding sites within the enhancer region, each footprint approximately 23 bp in size. The additional sites were denoted AREs IIIB, IIIA, IV, V, and VI with respect to their position relative to ARE III.

The affinity of the sites varied considerably. Among the six sites, site III had the highest affinity consistent with the study by Trapman and colleagues (Cleutjens, 1997a). Overall, however, the AREs were 15-60-fold lower affinity than the consensus. This observation may bear on the tissue specificity of PSA expression.

The observation that the affinities of AREs in the enhancer are significantly lower than the consensus raised the issue of their physiological relevance. Indeed, inspection of the DNA sequences within the footprinted region revealed few matches to the consensus ARE. Even ARE III diverged from the consensus by two nucleotides. To investigate this issue in more detail, three experiments were performed. First, the enhancer AREs were subjected to substitution mutagenesis to determine which sites were important in co-transfection experiments with AR into BHK cells. The key constructs were then compared by transfection into a more physiological prostate cancer cell line, LNCaP. Finally, a procedure was developed to purify intact AR to homogeneity from mammalian cells and employed the intact AR to study binding to the enhancer and its substitution mutants.

5.2.2.3 Enhancer Mutagenesis and Transfection Analysis

To establish the physiological validity of the new AR-binding sites, they were mutagenized individually and in select pairwise combinations. The AREs were replaced by GAL4-binding sites using PCR™ mutagenesis techniques. The substitutions were constructed based on the positioning of the footprints. In creating the substitution mutants, it was attempted in some cases to remove precisely the site and in others it was attempted to disrupt both the target site and putative adjacent sites. In all cases the original spacing was preserved by replacing the enhancer sequences with an equal number of bases. The 17-bp GAL4 sites were preserved because GAL4 is a yeast transcriptional activator, and numerous studies have shown that in the absence of GAL4, or its derivatives, the sites have no endogenous transcriptional activity in mammalian cells (Emami and Carey, 1992). The DNase I footprint analysis demonstrated that mutants lacking either ARE III, ARE IV, or ARE V no longer bind the ARDBD but instead bind to the GAL4 DNA binding domain.

To determine whether the AREs contributed to the AR response, co-transfection assays were performed in the baby hamster kidney (BHK) cell line. BHK cells were chosen because they contained low amounts of endogenous AR (i.e., relative to LNCaP) as measured by immunoblotting and were unlikely to contain prostate-specific transcription factors. This experimental scenario permitted the direct assessment of the contribution of co-transfected AR, and its interaction with AREs, to enhancer activity. The transcriptional activity of the enhancer was dependent upon co-transfected AR and the addition of 1 nM R1881. Sites IIIA, III, IV, and V contributed significantly to enhancer activity because, when these sites were mutated, transcription decreased by 50-75% relative to wild type. In contrast, mutation of sites IIIB and VI had only marginal effects.

The wild type and mutant enhancer constructs containing a luciferase reporter were transfected into an LNCaP cell line. By differing the concentration of ligand it was possible to observe differences in the effects of particular mutants, i.e., different mutants might be sensitive to the concentration of active AR. At 1 nM R1881 the individual site mutants all retained low activity averaging about 20% that seen with wild type. However, the effects of S-III and S-IV mutants were consistently more severe at 0.3 nM ligand. Furthermore, the residual, but reproducible, activity of the four-site mutant (S-All) at 1 nM ligand disappeared at 0.3 nM. Remarkably, the S-IIIA and S-V mutants retained much of their activity at the lower concentration of ligand. In all cases the sites appeared to act synergistically in LNCaP cells as removal of any site elicited a disproportional decrease in activity. The transcriptional activities of the mutants were similar to those observed in BHK cells, although the deleterious effects of individual mutations were more pronounced in LNCaP. The more severe effect in LNCaP might be attributed to the fact that the LNCaP line expresses physiological levels of AR, whereas the CMV-driven AR is likely to accumulate at high levels in BHK cells. Alternatively, the presence of prostate-specific factors may modulate the response to AR in LNCaP.

To verify further that AR binding to individual AREs is responsible for induction of the enhancer activity, three point mutations were created targeted to site V, a novel site identified in this study. Site V was chosen because its sequence matched the consensus more clearly than sites IIIA and IV, and site III has already been validated as an authentic ARE by point mutagenesis in other studies. Furthermore, AR apparently binds sites III and V in footprinting experiments with LNCaP extracts. Among the three point mutants, mutants, MV1 and MV3 were inactive for AR binding whereas mutant MV2 retained AR binding activity comparable with that of wild-type site V as determined by DNase I footprinting and gel shift assays. When tested for enhancer activity by transfection into in LNCaP cells, the activity of these mutants correlated with their AR binding activity. The activity of MV1 and MV3 is significantly reduced while the activity of MV2 is comparable with that of the wild-type enhancer.

Since hormone-responsive elements are conserved among different nuclear receptors, it is possible that the PSA enhancer activity might not be AR-specific. To address the receptor specificity issue, the responsiveness of this enhancer was tested to progesterone receptor (PR). The study was performed in BHK cells as the AR in LNCaP cells contains a mutation in AF-2 that renders it activable by numerous ligands. Such an effect would preclude measuring the specificity and contributions of PR to enhancer activity. Both AR and PR, when co-transfected with a reporter template containing four ARE sites upstream of the luciferase gene, were able to strongly induce activity in a ligand-dependent fashion. However, co-transfection of AR but not PR had a significant effect on PSA enhancer activity.

5.2.2.4 Synthesis and Purification of Intact AR

The tandem arrangement of low affinity AREs was reminiscent of many eukaryotic promoters where cooperative DNA binding by activators is an important mechanism for ensuring specificity in gene expression. The DNA binding experiments were performed with ARDBD, which, reasoned based on previous studies of GR and AR, could be missing domains necessary for cooperativity. Indeed data demonstrated that ARDBD filled the enhancer sites at widely varying concentrations, whereas cooperative binding is generally characterized by simultaneous site occupancy.

To understand the binding profile of intact AR it was necessary to purify AR to homogeneity. Although AR had been purified previously from the insect baculovirus system (Chang et al., 1992), AR was purified from mammalian cells in the event that AR was post-translationally modified in subtle ways that might influence its activity. AR had also previously been expressed in the mammalian vaccinia system (De Vos et al., 1994). This system was tested, but the high level of overexpression and cytotoxicity of the virus appeared to preclude important modifications, and prevent AR from being used for certain applications.

Thus, AR was stably expressed in both HeLa cells, where AR has been shown to be active in co-transfection assays, and in LNCaP cells, where AR is normally expressed and is essential for normal metabolic growth. Using an approach previously used in the purification of the thyroid receptor (Fondell et al., 1996), a subclone of AR was generated that contained the 8-amino acid FLAG epitope at its amino terminus. The FLAG-tagged AR (fAR) was then introduced into an amphotropic retroviral vector pSRα, packaged into virus, and used to stably transform HeLa and LNCaP cells (Sawyers et al., 1992; Muller et al., 1991).

Stable HeLa cell lines were selected by resistance to G418. Clones expressing fAR were identified by immunoblotting cell extracts against the FLAG epitope. Clone 2, which expressed the highest level of fAR, was chosen for further analysis and scale-up. One caveat of the approach is that fAR may not behave like the endogenous AR due to the addition of the FLAG immunotag. To address this issue fAR was subjected to several biological and biochemical tests. First, a plasmid expressing fAR was transfected into BHK cells and it was shown that it stimulated PSA enhancer activity to the same extent as native AR. Although this test confirmed the efficacy of fAR, it was important to determine whether the stably expressed fAR was functional because it was purified from the cell lines for biochemical analysis. To address this issue a luciferase reporter containing the entire PSA promoter/enhancer region previously shown to be highly AR-responsive (Pang et al., 1997) was transfected into clone 2 HeLa cells. HeLa cells are an ideal assay system because they do not contain appreciable amounts of endogenous AR and therefore allow the direct measurement of the effects of the fAR on transcription.

Data demonstrated that the PSA transcriptional activity was 5-fold higher in the fAR-HeLa cells in the presence of 1 nM of the synthetic androgen agonist R1881 than in its absence. In contrast, R1881-activable enhancer-mediated transcription was undetectable in the parental HeLa cell line. Although the absolute level of stimulation was 5-fold lower than that observed in LNCaP cells, this might be explained by the fact that fAR-HeLa cells do not contain prostate-specific factors that might augment enhancer activity. Nevertheless, the data indicate that fAR is functional for transcriptional activation in vivo. fAR levels were also compared the in nuclear extracts prepared from clone 2 HeLa cells in the absence or presence of R1881. As expected, R1881 was able to stimulate fAR nuclear translocation resulting in approximately 10-fold more fAR in extracts from R1881-treated clone 2 cells vs untreated cells.

To test further the in vivo function of LNCaP fAR, an immunofluorescence assay was performed using FLAG monoclonal antibodies. fAR was localized to the cytoplasm in steroid-depleted medium. However, after treatment with 1 nM R1881, the majority of fAR translocated into the nucleus. Because LNCaP cells contain endogenous AR, it was necessary to determine the ratio of fAR to the endogenous AR. Similar amounts of nuclear extract from the parental and fAR-LNCaP cells were subjected to immunoblot analysis using antibodies against AR. There appeared to be approximately twice as much AR in fAR-LNCaP cells as in the parental cell line, indicating that the expression levels of fAR and endogenous AR are approximately equal. This result was further verified by subjecting the fAR-LNCaP nuclear extracts to immunoprecipitation with anti-FLAG antibody to remove the fAR. Only half of the total AR-specific signal was depleted under conditions where all of the fAR was removed.

Next, anti-FLAG immunoaffinity chromatography was employed to purify fAR from the extracts. The major advantage of the FLAG approach vs standard immunoprecipitation is that the AR can be eluted from the resin with FLAG peptide for subsequent biochemical analyses. A silver-stained gel of the purified FLAG-tagged AR from both fAR-LNCaP and fAR-HeLa cells revealed a prominent band at 110 kDa, the size predicted for AR. To ensure that the band was indeed fAR, extracts from the parental LNCaP and HeLa cell lines were subjected to a mock immunopurification. The 110-kDa band was not observed, and only a low background binding of contaminant proteins was evident on the gel. Furthermore, the highly pure fAR is immunoreactive to polyclonal AR antibodies in blotting analysis.

Purified fAR was then subjected to DNA binding assays to examine its ability to bind the ARE sequence. The gel shift study showed that 10 ng of fAR, purified from nuclear extracts of fAR-HeLa and fAR-LNCaP lines treated with R1881, gives rise to specific gel shift complexes on a $^{32}$P-labeled consensus ARE oligonucleotide but not on a mutant ARE containing a scrambled arrangement of bases in one of the dyad half-sites. Further addition of 100 nM R1881 had little effect on the binding activity either in this study or in a parallel study, where more limiting amounts of AR were added. Mock protein preparations from wild-type HeLa and LNCaP nuclear extracts did not generate shifted complexes nor did protein prepared from cytoplasmic extracts of the FLAG-tagged cells.

5.2.2.5 Cooperative Binding of fAR to the PSA Enhancer

In cases such as the mammalian interferon β promoter (Thanos and Maniatis, 1995), the yeast GAL4-controlled GAL1-10 promoters (Kang et al., 1993), and others, it has been found that small changes in the concentration of limiting activators can cause large changes in transcriptional output. Occupancy of those promoters by their respective activators occurs in a cooperative fashion. The cooperative occupancy is a result of protein-protein interactions between activators bound to adjacent sites. Cooperative binding of AR has previously been observed on the rat probasin and the mouse sex-limited regulatory regions (Scheller et al., 1998; Kasper et al., 1994). These studies prompted the inventors to investigate whether AR binds cooperatively to the sites within the PSA enhancer.

A $^{32}$P-labeled PCR™ fragment from −4309 to −4011 of the enhancer was subjected to DNase I footprinting studies. Increasing concentrations of ARDBD led to gradual protection of the AREs such that 75% occupancy of ARE III and ARE V occurred at 350 nM and 1.4 µM protein, respectively. In contrast, LNCaP fAR occupied several of the sites simultaneously. A 2-fold increase in concentration from 7 to 14 nM led to 60% protection of AREs III, IV, and V. ARE IIIA filled at the slightly higher concentration of 56 nM AR and coincided with greater than 80% occupancy of sites III, IV, and V. More remarkably, fAR protected not only AREs IIIA, III, IV, and V from DNase I cleavage, but also the regions between the sites. The binding is specific because mutation of all four AREs abolished the entire DNase I footprint. Furthermore, one striking similarity between the protection patterns of AR and ARDBD is a distinct DNase I-hypersensitive site upon protection of site V. This observation indicated that AR was binding in a manner similar to that of ARDBD. A weak footprint was also noticed below site V that had not been detected with ARDBD in earlier experiments.

It has been reported that regions outside of the DNA binding domain of AR can contribute to its affinity, and possibly specificity, although the mechanism has not been determined (Kallio et al., 1994). To eliminate the possibility that intact AR has different specificity requirements than the ARDBD alone, the affinities of fAR for AREs III, IV, and V were compared by gel shift. It was found that although the affinity of ARDBD was >10-fold lower than that of AR, both proteins exhibited the same relative affinities for different individual sites. Taken together, the data suggest that the ability of fAR to bind simultaneously to the AREs within the enhancer is an indication that AR binding is cooperative.

In a DNase I footprint study comparing binding of ARDBD to individual mutants in AREs IIIA, III, IV, and V and a mutant removing all four sites, the individual mutants revealed a significant reduction of ARDBD binding only to the mutated site, whereas binding of ARDBD to other sites was unaffected. S-All, on the other hand, completely abolished binding to all four sites.

The binding profiles of fAR were far more complex. Each of the individual site mutants abolished tight binding to that site, although a weaker nonspecific protection over the mutated site was observed in some cases. For example, mutation of AREs III, IV, and V led to a decrease in protection of the site from 75 to 25%. Mutations of ARE IIIA or V had only a small quantitative effect on binding to sites III and IV. The mutation to site V did, however, abolish the additional footprint below site V again arguing for it relevance as an AR-binding site. In contrast, mutations in ARE III and IV clearly diminished cooperative binding to all sites at lower concentrations of fAR. This ARE IV result was surprising because individually it is a much weaker site for AR than ARE III. This observation suggests that the intrinsic affinity of individual AREs does not necessarily correlate with their role in cooperative binding. However, when all four sites were mutagenized, AR binding to the enhancer was largely abolished. The disappearance of the footprint in the S-All mutant suggests that the partial protection seen in the individual site mutants, even over the mutant sites themselves may be due to AR binding nonspecifically through interactions with AR bound specifically at intact neighboring sites.

To demonstrate further the physiological relevance of AR binding to this region, nuclear extracts prepared from LNCaP cells with or without androgen treatment were used to perform footprinting assays on the enhancer. The footprint of LNCaP extracts treated with R1881 was remarkably similar in some respects to that obtained with intact fAR. First, binding to ARE III and V is evidently hormone-dependent although the footprints were not as distinct as those generated by purified fAR. Hormone-dependent weak protection was also observed below site V as with the purified receptor. However, although proteins in the extract apparently bound to sites IV and IIIA, and generated footprints similar to that of intact fAR, the binding was not dependent on hormone. Other factors in the nuclear extracts might bind to these sites, masking the effect of AR binding. Alternatively, the extracts from untreated cells still contain low amounts of AR, and it is plausible that the footprints are due to binding by AR. It is also evident, however, that there are other regions bound by proteins other than AR in the nuclear extract in a hormone-independent fashion.

5.2.3 Discussion

The PSA gene has been employed as a model to understand how AR binds to and activates transcription of a natural target gene expressed during prostate cancer. Although previous studies had revealed the existence of two ARE sites within the proximal PSA promoter, the effect of the proximal promoter alone on the activity and tissue specificity of PSA gene expression is minor (Pang et al., 1997; Cleutjens, 1997a; Schuur et al., 1996). More recent studies led to the view that the major control region is an enhancer centered ~4.2-kb upstream of the PSA gene. Deletion mutagenesis around this region revealed that the androgen responsiveness of the enhancer is conferred by a 455-bp fragment bearing a single, moderate affinity ARE referred to as ARE III (centered at −4143). This region was subcloned upstream of a reporter gene and studied its response to AR. DNase I footprinting results, using both AR DNA binding domain and full-length AR, revealed that there are multiple AREs with varying but low affinities when compared with the consensus ARE. These sites were termed ARE IIIB, IIIA, III, IV, V, and VI and were centered at −3955, −4079, 4143, −4179, −4225, and −4298, respectively.

It was demonstrated that four of these nonconsensus AREs (IIIA, III, IV, and V), regardless of their low intrinsic affinity for AR, contribute significantly to the androgen-responsive transcriptional activity. Removal of these four sites strongly negated enhancer activity in LNCaP and in BHK cells, although the effects were less evident in BHK cells possibly due to high-level overexpression of AR from the co-transfected effector plasmid or a lack of cell-specific factors. It was found that fAR binds cooperatively to these sites in vitro.

The large difference in the size of the protected region by AR vs ARDBD was surprising. This effect could have multiple explanations including the following: (i) the existence of additional AREs that bind cooperatively to intact AR (i.e., such as the weakly protected site below site V); (ii) nonspecific interactions of AR with the intervening DNA, again mediated by cooperative interactions; (iii) finally, either a general distortion of the enhancer fragment or the larger mass of AR vs ARDBD might simply lead to steric inhibition of DNase I cleavage between the sites. The mutagenesis data support the idea that multiple AR molecules are cooperatively binding both specifically and nonspecifically along the DNA to provide a stable androgen-responsive nucleoprotein complex. This oligomerization, however, is dependent upon the identified AREs because mutagenesis of the four main AREs abolishes both specific and nonspecific binding.

Cooperative binding of activators to multiple, adjacent low affinity sites and the resulting synergistic effects on gene expression are a common mechanism for ensuring specificity in the transcriptional response (Carey, 1998). In the case of the PSA enhancer the low affinity AREs may ensure that binding occurs only at a higher concentration of AR. In situ hybridization studies on rat tissues, for example, have shown that prostatic secretory epithelial cells are among two or three cell types expressing the highest levels of AR in the body (Chang et al., 1995).

The presence of multiple AREs also augments the androgen responsiveness of the enhancer through synergy. Synergy is defined as the greater-than-additive transcriptional response to increasing numbers of bound activators. The current view is that synergy results from simultaneous interaction of multiple activators with the transcriptional machinery. These interactions lead to cooperative recruitment of the general machinery and the ensuing synergistic transcriptional response. In the case of the PSA enhancer, simultaneous binding of multiple AR molecules is in part responsible for the synergistic androgen-dependent effect on PSA gene expression (Cleutjens et al., 1996). This effect, when superimposed with a parallel synergistic effect of AR on AREs I and II within the proximal promoter (Schiedner et al., 1998) would, in principle, generate a sensitive and potent response of the gene to androgens.

The use of nonconsensus sites to regulate gene expression has been widely observed in nature. The consensus is an artificial amalgam of sites from various steroid receptor-responsive elements and, as such, binds and mediates response to several related steroid receptors (i.e., AR, GR, mineral corricoid receptor, and PR). The specificity for a particular receptor is likely conferred by contextual interactions between a single site or combinations of sites and the receptor. In line with previous observations that AR and PR share near identical consensus hormone response elements, it was demonstrated that both AR and PR were able to efficiently induce the activity of a construct containing four consensus AREs. However, when tested on a construct containing the PSA enhancer, only AR was able to stimulate the activity. This leads to the conclusion that nonconsensus sequences may play a pivotal role in conferring receptor specificity. Studies on GR, for example, have also established that the DNA sequence of the site influences nuclear receptor activity, possibly through conformational changes in the ligand-binding domain (Starr et al., 1996; Lefstin and Yamamoto, 1998). Furthermore, natural low affinity sites that bind AR are commonplace. In one case, the ARE in the rat probasin gene was shown to display an inherent preference for AR over GR suggesting that nonconsensus changes in DNA sequence may represent a basic mechanism for conferring receptor specificity (Claessens et al., 1996).

Contextual cooperative interactions involving interplay between multiple AREs and domains of AR also regulate specificity. In an elegant study that emphasized the complex nature of receptor DNA binding specificity, Robins and colleagues (Scheller et al., 1998) studied the DNA binding properties of domain-swap chimeras of AR and GR. The target promoters included both a standard array of consensus steroid (hormone) response elements and the natural AR-responsive enhancer of the sex-limited protein (slp) gene of mice. Whereas the different chimeras bound to and functioned from standard steroid response elements (Scheller et al., 1998), AR bound tightly and cooperatively to the nonconsensus slp enhancer AREs. The most efficient cooperativity required the AR DNA binding domain and its natural ligand and amino-terminal domains. The ligand and amino-terminal domains could not be substituted by the analogous domains of GR, which appeared to, in fact, suppress specific enhancer binding. The study implied that contextual AR-AR and AR-DNA interactions occurring within the nucleoprotein complex on the slp enhancer are the key determinants of specificity.

Although contextual, cooperative AR-AR interactions are likely to contribute to the specificity of PSA gene expression, other mechanisms must exist to ensure an accurate, cell-specific transcriptional response. Indeed, DNase I footprinting studies have identified binding sites for prostate-specific and ubiquitous transcription factors within the PSA enhancer and promoter (Schuur et al., 1996; Riegman et al., 1991; Sun et al., 1997). Henderson and colleagues (Schuur et al., 1996) used gel shift analysis to identify several complexes, which were specific to extracts prepared from LNCaP cells. It was speculated that some of these complexes located between −4150 and −4000 were due to binding of AR, a finding supported by the data since this region contains site IIIA. However, other complexes within the enhancer appeared unique and may represent binding of prostate-specific factors. Indeed, Farmer and Freedman recently identified a prostate-specific factor, which appears to bind adjacent to the ARE IV. The footprint assay using crude LNCaP nuclear extracts also demonstrates that in addition to regions around ARE IV, other regions were protected by extracts from both R1881-treated and -untreated cells.

Mechanistic studies on nuclear receptors suggest that they stimulate transcription by direct or indirect communication with the general factors (Hori and Carey, 1994). Direct interactions between the general factors and several nuclear receptors including AR have been detected biochemically (Ing et al., 1992; Jacq et al., 1994; Sadovsky et al., 1995; McEwan and Gustafsson, 1997). In addition to general factor interactions the current view is that the receptor also interacts with ancillary factors called co-activators to increase the recruitment of the transcriptional machinery.

For example, CBP/p300 has been found to support activation by many nuclear receptors including AR (Chakravarti et al., 1996). In addition, co-activators for individual nuclear receptors have been isolated using both biochemical assays and yeast two-hybrid screens. Examples include the TRAPs for the thyroid hormone receptor (Fondell et al., 1996), ARA70 for the androgen receptor (Yeh and Chang, 1996), SRC-1/p160 (Onate et al., 1995) and RIP 140 (Cavailles et al., 1995) for the progesterone, estrogen, and other steroid receptors, and GRIP1 for the glucocorticoid and androgen receptors (Hong et al., 1996). The yeast two-hybrid systems have identified individual interacting molecules, whereas biochemical studies have shown that several co-activators may simultaneously associate with a receptor to form a large multiprotein complex (Chakravarti et al., 1996). For example, the thyroid receptor-associated proteins or TRAPs contain at least 9 polypeptides, which form a transcriptionally active complex with thyroid hormone receptor and play a role as positive co-activators in vitro (Fondell et al., 1996). Vitamin D receptor has also recently been shown to interact with multiple polypeptides, the DRIPs, which are very similar in mass and may be identical to the TRAPs (Rachez et al., 1998). Other systems have revealed that co-activators may also be gene- and site-specific (Kim et al., 1996; Cepek et al., 1996).

5.3 Example 3—Animal Models of Prostate Cancer

A variety of clinically accepted animal models may be employed to demonstrate the facility and utility of the disclosed methods and compositions. A summary of the recognized protocols employed by the inventors in the practice of the present invention is provided in this example.

5.3.1 Human Prostate Cancer Xenografts

These models are derived from human prostate cancer tissues from patients, which were established in immunodeficient mice as xenografts and can be passaged as cell lines in vitro. The most well studied models are listed below:

| Model | Reference | Androgen status/ ai progression | Bone metastasis | Passage In vitro |
|---|---|---|---|---|
| LAPC4 | Klein et al., 1997 | AD/yes | Yes, micro | yes |
| LAPC9 | Craft et al., 1999 | AD/yes | Yes, micro | no |
| CWR22 | Cunningham et el., 1996 | AD/yes | ? | yes |
| LNCaP | Horoszewicz et el., 1983 | AD/yes | ? | yes |
| C4-2 from LNCaP | Thalmann et al., 1994 | AI/yes | yes | no |
| CL1 from LNCaP | Patel et al., 2000 | AI/yes | yes | yes |

5.3.2 Rodent Models of Prostate Cancer

A variety of rodent models of prostate cancer have been developed. These are summarized in the article by Zhau, Li and Chung (2000). This review lists all the accepted rodent models with their respective characteristics. The main advantage of rodent models is that the cancer exists in an intact host immune system. Conversely, these rodent models often do not have all the important disease phenotype of human. For example, none of the rodent prostate cancers metastasize to bone, which is a hallmark of advanced human prostate cancer.

5.4 Example 4—Targeted Gene Therapy for Advanced Prostate Cancer

Patients with advanced prostate cancer have a grim prognosis when tumors become androgen independent (AI). This progression occurs eventually for all patients during the course of conventional hormonal ablation, leading to death within 18 months with no real alleviation with current second and third line chemotherapeutic regimens. As they progress to become more malignant, AI cells develop resistance to many apoptotic programs induced by various stimuli (Cardillo et al., 1997; Newling, 1996). It is highly desirable, therefore, to develop an efficient and safe gene therapy protocol tailor-made to treat prostate cancer including the aggressive, androgen-independent stage.

5.4.1 Improvement and Modification of PSA Enhancer

The native PSA enhancer/promoter (PSE, consisted of −5322 to −2875 and −541 to +11 of PSA gene) inserted into adenovector can indeed direct tissue specific and androgen-inducible expression in PSA expressing cells, but its transcriptional activity is drastically lower than the constitutive CMV promoter. It is likely that a chimeric promoter derived from a composite of key natural enhancer element and artificial transcriptional element would greatly augment the transcriptional potency of native PSE while retaining its tissue specificity. The two most active constructs, designated PSE-BAC and PSE-BC, are created by duplication of the PSA enhancer core and, respectively with or without, insertion of the artificial regulatory element composed of 4 tandem copies of ARE (ARE4) into PSE. The small 390-bp enhancer core containing the AREs described in Huang et al., (1999), was essential for proper functioning of PSA enhancer. This 390-bp region is wholly contained within the larger 455-bp region described in Cleutjens et al., (1997a) and extends from −4326 to −3935 of the larger fragment. The transcriptional activity of PSE-BAC and PSE-BC are dramatically 20-fold higher than PSE in the presence of androgen in LNCaP cells. Expression mediated by both constructs was induced greater than 1000 fold in the presence over the absence of androgen. Importantly, these modified chimeric PSE promoters remained inactive in non-prostate cells. These greatly improved chimeric PSE promoters achieved much higher and specific expression in the PSA expressing prostate cancer cells than the native PSA promoter.

5.4.2 Enhancement of PSE to Improve Expression in AI Prostate Cancer

Since AR and endogenous PSA expression are diminished in CL lines compared to parental LNCaP cells, introduced PSE reporter gene expression is low and refractory to androgen induction. Data suggest that other non-AR factors exist to fully regulate PSE activity. Deletion of the enhancer core (−4326 to −3935) completely abolished the activity of PSE. However, replacing the enhancer core with 4 tandem binding sites of AR (ARE4) did not restore the activity. Interestingly, the activity of the PSE-BC construct with duplication of the enhancer core is consistently about 5-fold higher than PSE in the CL cells in the absence of androgen. This PSE-BC activity is about 5-10% of CMV promoter. Interestingly, when the PSA regulatory sequence from −3935 to −3744 that contains an active PDEF site in PSE-BC was deleted and replaced by ARE4 in the PSE-BAC construct, the 5-fold stimulatory activity of PSE-BC was eliminated.

5.4.3 Trail Mediated Apoptosis of AI Cancer Cell

It has been shown that commonly used prostate cancer cell lines DU145, PC3, and LNCaP are unresponsive to TRAIL-mediated apoptosis (<5% cytotoxicity). After pre-treatment with sub-toxic doses of Act D (50-100 ng/ml), these resistant cells become sensitive to even low doses of TRAIL (5 ng/ml) resulting in 30-60% killing in all three lines (Bonavida et al., 1999). CL1 cells express all the four TRAIL receptors, and are resistant to TRAIL mediated apoptosis as well as to the low priming concentrations of Act D when given alone. However, after 4 h priming with Act D, a significant synergistic augmentation of apoptosis is achieved (p=0.04 for highest doses of Act D+TRAIL over TRAIL alone, p=0.04 for TRAIL vs Act D alone). In fact, when Act D priming time is extend to 24 h, TRAIL mediated apoptosis is further augmented to 70%. Act D appears to induce suppression of anti-apoptotic modifiers expression, such as $BCl-X_L$.

Data support the use of TRAIL in conjunction with low dose Act D to treat advanced AI prostate cancer. However, with a gene therapy approach, addition of Act D prior to vector mediated gene delivery and expression could potentially interfere with optimal TRAIL production. It would appear that administration of Act D after TRAIL gene expression would be more feasible technically. In fact, it was shown that changing the sequence of addition (i.e., adding Act D 24 hr later in the preexistence of TRAIL (T/A) or simultaneous addition (T+A)) did not significantly impair the sensitizing effect of Act D.

5.4.4 Further Manipulation of PSA Enhancer Elements to Enhance Specific Transgene Expression in AD and AI Prostate Cancer Tested in transfections, the absolute activity of two most active constructs, PSE-BC and PSE-BAC, is even higher than the strong CMV promoter in LNCaP cells under optimal androgen concentration. Granted that the activity of PSE-BC is 5 fold higher than PSE in AI CL2 cells, its absolute activity is still quite low (about 10% of CMV) and no longer inducible by androgen. Multiple copies of key transcriptional factor binding sites leads to cooperative and synergistic enhancement of activity in natural promoter settings (Huang et al., 1999; Weintraub et al., 1990) and synthetic promoters (Tan, 1999). Thus, insertion of more copies of PSA enhancer core may further increase the activity in LNCaP and AI CL cells.

5.4.5 Generation of More Copies of Enhancer Core Insertion into PSE

Starting with the PSE-B plasmid (derived from pBS, Stratagene Co.), which contains a unique BstEII at −4326, multiple concatamers (2×, 3×, 4×) of enhancer core, −4326 to −3935, which is flanked by BstEII restriction sites may be inserted into pPSE-B. An equivalent set of multiple enhancer core insertion into pPSE-BA can also be generated. Both luciferase and GFP activity may be the read out for the promoter activity. All of the new modified PSE constructs may be evaluated by Lipofectamine Plus (Gibco Co.) mediated transfection into PSA+ androgen responsive LNCaP and LAPC-4 cells, and androgen independent CL1 and CL2 cells. Promoter activity may be analyzed in the absence of androgen (using 10% charcoal stripped fetal bovine serum) or in the presence of 1 nM R1881, a more stable synthetic androgen. Maximal activation of PSE promoters can be achieved with 1 to 10 nM R1881.

5.4.6 PDEF Binding Site Mutation and Re-Insertion of Even Multiples of PDEF Sites The PDEF site at −3848 (E site) was determined to be the most active for binding comparing to other potential consensus sites in the PSA upstream region (Oettgen et al., 2000). The GGAT sequence is the main determinant for specific recognition and binding by PDEF over other Ets transcriptional factor. This E site may be mutated, replacing the AGAAGCAGGATGTGATAG (SEQ ID NO:32) 18 bases PDEF site with a XhoI site CCCTCGAGCGC (SEQ ID NO:33). Site directed mutagenesis is accomplished by double-stranded method (Chameleon, Stratagene Co.) without further sub-cloning. The 5'GGTTAGGCATAACCCTCGAGCGCAAGAAGTATTTAATGG-3' (SEQ ID NO:34) mutagenic oligonucleotide and a selection oligonucleotide 5'AGCTGCCCACATTTAAAT-3' (SEQ ID NO:35) for elimination of a unique SalI site will be utilized in the mutagenesis method according to manufacturer's instruction. The PDEF deletion may be generated in PSE-BC, which processes the highest transcriptional activity in AI cells. This heightened promoter activity allows more sensitive detection of any diminution caused by the mutation.

Once the PDEF deletion is generated, the inserted XhoI facilitates addition of multiples of PDEF sites, starting with the PDEF dimer sites (synthetic 54-mer oligonucleotide pair). The overhanging sites are created such that insertion of one copy of PDEF dimer destroys the flanking XhoI sites and insertion of 2 or more copies generates one or more internal SalI sites. This feature facilitates screening and analysis of clones. All clones are confirmed by DNA sequencing. The promoter activity is analyzed by transfection into the same cells as specified above under the same conditions. Promoter clones are identified and inserted into gutless Ad.

5.4.7 Production of Gutless Ad (ΔAd) for In Vivo Analysis

The ΔAd production system has been refined utilizing the yeast Flp site-specific recombinase. The main difficulty is the inability to fully disable all helper viruses with the current Flp expression in the 293-Flp production cell line. This problem may be remedied by inducing higher Flp expression using a linked-dihyrofolate reductase (DHFR) selection for gene amplification. Regardless of the status of the ΔAd system, the vectors may be prepared using a similar helper-dependent system (Parks et al., 1996). This system utilizes the 293Cre4 cells to inactivate the helper virus AdLC8cluc by deletion of the viral packaging signal flanked by loxP sites (Cre recombinase target site). Thus, co-propagated ΔAd with retained packaging signal will be preferentially amplified.

The methodology of ΔAd propagation using the pBT plasmids has been described (Tamanoi and Stillman, 1982). The ΔAd containing pBT plasmid contains a pair of PmeI sites flanking the ΔAd sequence. Digestion with PmeI results in precise excision of ΔAd DNA within 3-bp of the 2 viral ITRs (inverted terminal repeat) such that efficient initiation of DNA replication can occur (Collins and Hohn, 1978). The inclusion of a phage lambda cos site (from SuperCosI, Stratagene Co.) in the plasmid backbone allows the use of in vitro lambda packaging to select for large plasmids (Parks et al., 1999, >38.8 kb) such that in vitro lambda packaging yields only ΔAd size large enough to be propagated (>27.7 kb). The plasmid containing the ΔAd-CMVTK DNA backbone has been generated. The ΔAd backbone has several convenient features for assaying functional infectious units and easy subsequent insertion of the prostate specific expression cassette. It contains a CMV-GFP or CMV-lacZ cassette for facile monitoring of ΔAd amplification and final titration of infectious units. The 20-kb human Ori sequence (Jang et al., 1989) was selected as stuffer sequence so that maximal in vivo ΔAd stability (Parks and Graham, 1997) and minimal stable genome size of 27.7-kb (Krysan et al., 1989) can be achieved. The unique NotI restriction site, a rare 8-base enzyme, is adopted for insertion of the PSE expression cassette flanked by 2 NotI sites.

5.4.8 Cloning of the PSE Driven Diagnostic and Therapeutic ΔAd Constructs

The pBS plasmid derived pPSE, pPSE-BC and pPSE-BAC driving the eGFP marker gene (Clontech Co.) expression have been generated. The unique SalI site, immediate 3' to the GFP gene may be utilized for insertion of IRES TKsr39 gene. The internal ribosome entry site (IRES) from encephalomyocarditis virus (EMCV) (Adam et al., 1991) had been shown to provide the most efficient means for co-expressing two genes from the same transcript (Ashkenazi et al., 1999). The EMCV IRES sequence has been obtained from pLNEPN (Ghattas et al., 1991) and is adapted to the TKsr39 coding sequence derived from pAC-CMV-TKsr39 (Gambhir et al., 2000) by DNA PCR™ methods for linkage to the GFP gene. The expression of two genes placed in the same bi-cistronic construct is highly correlative as evaluated by MicroPET imaging assays.

The cloning of active soluble TRAIL gene, amino acids 114 to 281 (Klein et al., 1997) is accomplished by adopting to it with 5' HindIII and 3' EcoRI site by DNA PCR™ from pS1346-TRAIL (Klein et al., 1997). The PCR™ generated TRAIL gene may be sequenced completely to ensure accuracy of the coding sequence. The NotI PSE regulated bi-cistronic expression cassette may be inserted into the pBT plasmid replacing the CMV-TK cassette.

5.4.9 Amplification and Propagation of ΔAd

To generate the ΔAd, the respective pBT plasmid may be digested with PmeI to release the ΔAd DNA which would then be transfected into 6-cm plate of 293Cre4 cells following the Superfection (Qiagen Co.) method. After 24 h, the cells are infected with AdLC8cluc at MOI of 1, and incubated until the monolayer showed complete cytopathic effect (48-72 h). The virus is then released from cells by 3 rounds of freeze thawing. To amplify the ΔAd further, cell-lysates (containing ΔAd) are serially passed on 293Cre4 monolayer cells with addition of helper virus MOI 1 during each round. The propagation and amplification of the ΔAd is determined by GFP or lacZ transferable units using a small portion of the harvested lysates. The titer of contaminating helper virus may be determined by plaque assay on 293 cells. An average of 7 rounds of serial amplifications are required to achieve adequate quantity of ΔAd. The ΔAd can be concentrated and further purified away from helper virus by CsC12 equilibrium density centrifugation. The 36-kb helper virus will have higher density than the smaller genome size ΔAd. The purity of the final ΔAd preparation can be determined by Southern Blot for any contamination of helper virus (<0.1%, Tamanoi and Stillman, 1982).

5.4.10 MicroPET Imaging to Evaluate In Vivo Restricted Expression of ΔAd after Systemic Administration The modified prostate specific promoter (designated here as PSE*) may be used to co-express HSV1-tk PET reporter gene along with the therapeutic gene or the marker GFP gene in the ΔAd (e.g., ΔAd-PSE*-TRAILiresTKs39, ΔAd-PSE*-GFPiresTKs39). Prior to in vivo analysis, ΔAd-PSE*-GFPiresTKsr39 may be shown to mediate prostate specific expression in prostate cancer cells (LNCaP, LAPC-4, and AI CL2 cells) and not in non-prostate cells.

The in vivo tissue restrictive expression of ΔAd-PSE*-GFPiresTKsr39 may be evaluated by injecting $10^8$ to $10^{10}$ infectious units into tail-veins of mice. The ΔAd-PSE*-GFPiresTKsr39 mediated PET image in different organs is assessed and correlated with histological analysis of GFP expression. Systemic administration of Ad with CMV promoter resulted in gene transfer primarily to the murine liver (Gambhir et al., 1998; MacLaren et al., 1999; Gambhir et al, 1999; Chappell et al., 2000). Thus, comparing the in vivo expression pattern of the prostate specific promoters to the CMV promoter in similar Ad constructs provides accurate measurement of tissue selective or restrictive capability of PSE* to prevent expression in non-permissive cells/organs.

5.4.11 MicroPET Imaging to Evaluate Prostate Tumor Specific Expression of ΔAd

The activity of the vectors (i.e., the promoters) may be evaluated in vivo using one of 3 different human prostate tumor models ensuring that crucial clinical stages will be covered. The first model, SC tumors of LNCaP and LAPC4 (Herz and Girard, 1993) cells are established in male mice which represent the androgen responsive, PSA producing tumors. The second tumor model is the AI variants of the first model. Male mice with established LNCaP and LAPC4 tumors may be castrated. The tumors that eventually grow out after initial regression are androgen-independent yet still produce PSA (Wu et al., 1994; Craft et al., 1999; Herz and Girard, 1993). The third group is the CL1 and CL1-GFP aggressive AI tumors that express negligible PSA. The xenografts are established by SC injection of $10^5$ to $10^6$ cells along with Matrigel (not needed for CL tumors) in the flanks of SCID mice (Herz and Girard, 1993). When tumors reached a size of ~53 mm$^3$, mice are injected with a range of ΔAd ($10^8$ to $10^{10}$ infectious units) intra-tumorally. The in vivo activity of the modified PSE* may be compared to the native PSE by comparing the magnitude of intratumoral PET reporter probe retention.

5.4.12 MicroPET Imaging with 18F-FPCV

18F-FPCV as a probe is highly specific for HSV1-TKsr39 resulting in improved sensitivity of PET images (Gambhir et al., 2000). Mice are anesthetized using avertin according to approved protocols. 24 to 48 hr after ΔAd mediated gene transfer, imaging is performed 1 hr after the injection of ~200 μCi of 18F-FPCV via the tail-vein. The 1-hr period allows for uptake and trapping of the tracer by TK expressing cells, and clearance from non-specific sites. Eight bed positions at 7 min/bed for a total scan acquisition time of 56 min are utilized. Images may be reconstructed using Filter Back Projection and subsequently analyzed.

5.5 Example 5—an Androgen Independent Metastatic Tumor Model for Prostate Cancer 5.5.1 Material and Methods 5.5.1.1 In Vitro Androgen Deprivation Treatment The human prostate cancer cell line LNCAP (American Type Culture Collection, Rockville, Md.) was maintained in standard RPMI 1640 medium supplemented with 10% fetal bovine serum, L-glutamine and antibiotics (50 IU/ml penicillin and 50 μg/ml streptomycin). Androgen deprivation was carried out by initial removal of culture medium and washing twice with serum-free RPMI medium. After two washes, cells were further incubated in serum-free medium at 37° C. for 15 min. Subsequently, medium was removed and culture medium was replaced with RPMI 1640 supplemented with 10% charcoal-stripped serum and antibiotics. The LNCaP variants that survived the androgen-deprivation selection process were gradually expanded to a stable line and were designated CL1. Therefore, the CL1 cells represent a pool of androgen resistant variants derived from androgen-dependent parental LNCaP cells.

5.5.1.2 Gene Transfer of Green Fluorescence Protein (GFP)

The GFP gene driven by CMV promoter was inserted into the pCEP plasmid vector (Invitrogen, Carlsbad, Calif.) containing a hygromycin resistance gene. Gene transfection of CL1 was carried out by lipofection using the LIPOFECTAMINE PLUS™ reagent protocol (Life Technologies, Gibco BRL, Gaithersburg, Md.). Briefly, the six-well protocol was implemented using 3 µg DNA that was combined with 6 µl of PLUS reagent, 100 µl of serum-free dilution medium, 4 µl of LIPOFECTAMINE™ reagent and 0.8 ml of transfection medium. This mixture was then added to the cells in the wells and after gentle mixing allowed to incubate at 37° C. at 5% $CO_2$ for 3 h. Fresh medium containing 10% fetal bovine serum (FBS) was added to the transfection medium. After incubating for 24 h the drug resistant colonies were selected and expanded by increasing concentrations of hygromycin (Sigma, St. Louis, Mo.) up to 200 µg/ml. The established CL1-GFP cell line which derived from a pool of hygromycin resistant cells and used for animal study contained 99.9% GFP expression cells as determined by flow cytometry and fluorescence microscopy.

5.5.1.3 Surgical Orthotopic Implantation

Six to eight week old male and female SCID mice (C.B.-167 scid/scid) were obtained and treated according to standard animal protocols. All animals were anesthetized with intraperitoneal ketamine before inoculation with tumor cells. For subcutaneous tumor growth, $1 \times 10^6$ cells were resuspended into 100 µl of phosphate buffered saline (PBS) without any additional growth supplement (e.g., Matrigel) and injected with a 27-gauge needle into the flanks of the SCID mice. For orthotopic, intraprostatic injection, a small 1-cm vertical mid-line incision in the lower abdomen was carried into the peritoneum. Using the seminal vesicles and bladder as an anatomic landmark, the prostate was exposed and identified. Using a 30-gauge needle, $5 \times 10^4$ cells in 5 µl of PBS were injected in dorsal prostate lobes under the prostatic capsule and the mice castrated. The abdominal wall and skin were then closed with fine surgical sutures. Four to five weeks later large tumors were visible and palpable, and when the performance status of the mice began to decline, the mice were sacrificed and necroscopy performed. The prostate, regional lymph nodes, major organs and whole skeleton were harvested for gross inspection, fluoroscopic and standard histologic examinations.

5.5.1.4 Analysis of Primary Tumor, Regional Adenopathy and Distant Metastasis

After procurement, tissues were inspected for gross evidence of tumor involvement, and then prepared for fluoroscopic microscopy, standard light microscopy and for RT-PCR™ analysis. Tissue sections were processed in 1 mm sections for fresh tissue fluorescent microscopy, in O.C.T. and liquid nitrogen for snap-frozen analysis as well as formalin fixation and paraffin embedding for standard histologic examination. Frozen tissue blocks were cut into serial 5 µm sections, mounted and then either visualized under a fluorescent microscope or stained with hematoxylin and eosin for light microscopy.

5.5.1.5 Semi-Quantitative Reverse Transcriptase-Polymerase Chain Reaction (RT-PCR™) Analysis Total RNA was extracted from LNCaP, CL1 culture cells, CL1, and CL1-GFP tumors using acid guanidine isothiocyanate-phenol-chloroform extraction. Reverse transcription of messenger RNA into cDNA was carried out by incubating titrated RNA with AMV reverse transcriptase, primer oligo (dT), dNTP, and RNAse inhibitor at 42° C. for 1 h. One µl of each cDNA sample was amplified utilizing PCR™ in a total volume of 25 µl (30 ng [$^{32}$P]-5'-oligonucleotide, 100 ng 3'-oligonucleotide primer, 2.5 µl modified 10×PCR™ buffer, 1.25 units Taq polymerase, and autoclaved double distilled water to a volume of 25 µl). The PCR™ mixture was amplified for 25 cycles in a DNA Thermocycler (Perkin-Elmer, Norwalk, Conn.). Each cycle consisted of denaturation at 94° C. for one min and annealing/extension at 65° C. for 2 min. The $^{32}$P-labeled PCR™ products were visualized directly by acrylamide gel electrophoresis and autoradiography. The following oligonucleotide primer pair sequences were used:

```
β-Actin:
5'-CAACTCCATCATGAAGTGTGAC-3'
(SEQ ID NO:36)

3'-CTCGCGTTCATGAGGCACACC-5'
(SEQ ID NO:37) (184 bp)

PSA:
5'-TGTCTCGGATCCTGGGAGGCTG-5'
(SEQ ID NO:38)

3'-CTCAGGAATTCGCCACGA-5'
(SEQ ID NO:39) (195 bp)

AR:
5'-CAAGCTCCTGGACTCCTGGCA-3'
(SEQ ID NO:40)

3'-TAGATGGGCTTGACTTTCCC-5'
(SEQ ID NO:41) (140 bp)

EGFF-R:
5'-CTTCTTGCAGCGATACAGCTC-3'
(SEQ ID NO:42)

3'-ATGCTCCAATAAATTCACTGC-5'
(SEQ ID NO:43) (441 bp)

VEGF:
5'-ATGCGGATCAAACCTCACC-3'
(SEQ ID NO:44)

3'-ATCTGGTTCCCGAAACCCTG-5'
(SEQ ID NO:45) (159 bp)

bFGF:
5'-CCCAAGCGGCTGTACTGCAA-3'
(SEQ ID NO:46)

3'-AGCTCTTAGCAGACATTGG-5'
(SEQ ID NO:47) (383 bp)

TGFβ1:
5'-GACTTCCGCAAGGACCTCGGC-3'
(SEQ ID NO:48),

3'-GCGCACGATCATGTTGGACAG-5'
(SEQ ID NO:49) (250 bp)

TGF-β2:
5'-CCTGTCTACCTGCAGCACACTCGA-3',
(SEQ ID NO:50)

3'-GGCGGCATGTCTATTTTGTAAACCTCC
(SEQ ID NO:51) (290 bp)
```

-continued

IL-6:
5'-ATGTAGCCGCCCCACACAGA-3'
(SEQ ID NO:52),

3'-CATCCATCTTTTTCAGCCAT
(SEQ ID NO:53) (159 bp)

BCL-2:
5'-CTTTGAGTTCGGTGGGGTCATGTG-3'
(SEQ ID NO:54),

3'-TGACTTCACTTGTGGCCCAGATAG
(SEQ ID NO:55) (318 bp)

E-cadherin:
5'-CTGAAGTGACTCGTAACGAC-3'
(SEQ ID NO:56),

3'-CATGTCTGCCAGCTTCTTGAAG-5'
(SEQ ID NO:57) (286 bp)

P53:
5'-TGGTACAGTCAGAGCCAACC-3'
(SEQ ID NO:58)

3'-AGCAGTCACAGCACATGACG-5'
(SEQ ID NO:59) (201 bp)

PTEN:
5'-GGACGAACTGGTGTAATGATATG-3'
(SEQ ID NO:60),

3'-TCTACTGTTTTTGTGAAGTACAGC-5'
(SEQ ID NO:61) (671 bp).

5.5.2 Results 5.5.2.1 Gross Necroscopy

CL1 cells rapidly induced palpable tumor formation within two weeks in both intact and castrated male SCID mice via both subcutaneous and intraprostatic injections with a tumor uptake of 100% (5/5 in each group). All mice receiving introprostatic injections developed bulky local tumors at 5 weeks with evidence of aggressive local invasion into adjacent organs, including the bladder, rectum, and seminal vesicles. In addition, 100% of mice receiving introprostatic injections (both castrated and non-castrated), developed gross pelvic and retroperitoneal neoplastic lymphadenopathy. Furthermore, similar gross pathologic features of CL1-GFP tumors were identified in both castrated and intact mice. In contrast, no metastatic disease was seen in any of the mice (both male and female mice) injected subcutaneously.

5.5.2.2 Histology of Primary Tumor, Lymph Nodes and Lung

Microscopic evaluation of primary tumor formation revealed irregular, infiltrating masses of poorly differentiated high-grade, anaplastic tumor cells. Acinar formation was absent, and areas of necrosis were evident. Mitotic figures were conspicuous and there was considerable variation in cellular and nuclear pleomorphism. Severe nuclear anaplasia was present with evidence of hyperchromatic, large nuclei associated with marked vacuolization and a course chromatin pattern. Large, abnormal nucleoli were frequently encountered. Local infiltration and invasion into surrounding tissues were prominent. Regional, pelvic and retroperitoneal lymph nodes showed loss of normal architecture and were nearly completely replaced by masses of tumor cells exhibiting similar histologic features as that of the primary tumor. Distant spread to the lung, seen by microscopy, demonstrated multiple, distinct micrometastatic foci of these large anaplastic cells within the parenchyma.

5.5.2.3 Patterns of Metastasis

Following introprostatic injection of CL1-GFP, the extensive and widespread micrometastatic disease that developed in the lymph nodes, liver, lung, spleen, kidney, brain and bone could be traced and demonstrated by GFP fluorescence activity. Areas of skeletal metastases included the femur and spine. GFP fluorescence microscopy was able to identify micrometastatic disease that could not be identified by light microscopy alone, as well as confirm the findings of gross disease.

5.5.2.4 Molecular Determinants for Malignant Behavior of CL1 Tumors

When compared to LNCaP culture cells, overexpression of b-FGF, IL-6, IL-8, VEGF, TGF-β1, TGF-β2, and EGF-R mRNAs was detected in both the CL1 cell line and CL1 tumors growing in intact and castrated SCID mice. A corresponding result was also found in the protein level determined by Western blot analysis. The same pattern, but to a slightly lesser extent, was seen in tumors grown subcutaneously when compared to those grown orthotopically. In contrast to LNCaP cells, a loss of E-cadherin, diminished levels of p53, PTEN, and an augmented bcl-2 mRNA expression were detected in CL1 cell line and tumors. Despite the long-term growth of CL1 cells in androgen-free culture condition, a low level of androgen receptor mRNA expression was still detected in both the cell line and tumors, but PSA was not detectable.

5.5.3 Discussion

The present animal model utilizes an androgen independent human prostate cancer cell line expressing GFP and demonstrates clinical behavior and molecular changes similar to aggressive androgen-independent prostate cancer in humans. The CL1 cell line features highly locally invasive and metastatic properties, which, as a result of the pre-ex-vivo selection of androgen resistant and aggressive clones, develops in a relatively short time as compared to other androgen-independent prostate cancer tumor models (Thalmann et al., 1994; Klein et al., 1997; Wu et al., 1994).

Previous tumor models have attempted at mimicking the natural progression of human prostate cancer but with limited success. The problem has been developing a tumor that will grow and metastasize spontaneously. Initial studies with LNCaP cell line showed very slow growth (Horoszewicz et al., 1983), and necessitated supplements such as Matrigel or tissue specific fibroblasts to grow subcutaneously (sc) (Wu et al., 1994; Stephenson et al., 1992; Pretlow et al., 1991; Passaniti et al., 1992; Chung, 1993). In addition, these sc-injected tumors had only sporadic metastatic capability (Thalmann et al., 1994). To improve the ability to metastasize orthotopically injected tumor models have been developed with some success (Thalmann et al., 1994; Yang et al., 1999). However, the models are limited by a lengthy latent period from the time of injection and metastasis (Thalmann et al., 1994; Klein et al., 1997), as well as, establishing sc tumors and subsequently transplanting tumor tissue orthotopically (Yang et al., 1999). The CL1 tumor model is unique in that no additional supplements were required for growth, and after direct orthotopic injection of CL1 cells, palpable tumor showing aggressive growth with extensive local invasion and micrometastasis was seen within 4 weeks. The tumor cells could also be easily detected microscopically because of the introduced GFP detection system using fluorescent microscopy. GFP fluorescence enabled the ready detection of micrometastases in the lung, liver, kidney, and bone where no gross tumor was evident. These results are similar to those of Yang et al. (1999), who demonstrated micrometastasis visualized by fluorescence microscopy only. However, the inventors were also able to confirm metastatic disease in the lymph nodes and lung by histological examination as well as in the other organs using RT-PCR™.

Many of the molecular changes in the expression of bcl-2, p53, PTEN, E-cadherin, TGF-β and other angiogenic factors observed in he CL1-GFP cell line reflect changes which have been observed in advanced hormone independent prostate cancer. It appears that the distinct molecular characteristics in CL1 are closely linked to its aggressive behavior. For example, the overexpression of Bcl-2 protein, an inhibitor of cell apoptosis, has been implicated in the development of androgen resistant prostate cancer cells (Raffo et al., 1995). Bcl-2 is also thought to be responsible for the poor response to anti-neoplastic drugs and radiation therapy seen in tumors by blocking apoptotic pathways. Furthermore, abnormal p53 expression has been found in more aggressive tumors and it appears to be an independent predictor of cancer recurrence after radical prostatectomy (Grossfield et al., 1998). Thus, overexpression of bcl-2 (Gao et al., 1999; McDonnell et al., 1992; DiPaola and Aisner, 1999) accompanied by diminished levels of cell cycle regulators such as p53 (DiPaola and Aisner, 1999; McDonnell et al., 1997; Cheng et al., 1999) and PTEN seen in the CL1 tumors might explain the apoptotic resistance to androgen deprivation as seen in clinically advanced CaP. Abnormal expression of the E-cadherin adhesion molecule in CaP correlates with Gleason score, the extent of local invasiveness and bone metastasis reflected in survival and recurrence after radical prostatectomy (Paul et al., 1997; Richmond et al., 1997).

On the other hand, the overexpression of the growth and angiogenic factors EGF-R, VEGF, IL-8, bFGF, TGF-βand IL-6 by the CL1 tumor model are also likely to be responsible for the aggressive growth and metastasis of the CL1 tumor grown in androgen deficient environment (Russell et al., 1998; Scher et al., 1995; MacDonald and Habib, 1992; Szabo and Sandor, 1998). It has been shown that LNCaP cells were refractory to TGF-β1, which was due to lacking of functional receptors (Guo and Kyprianou, 1988). Therefore, the upregulation of TGF-β in CL1 is more likely to act as a paracrine growth factor or an immunosuppressor. Although the characteristics of loss of androgen sensitivity, autocrine/paracrine activity, and tumor progression in CL1 resemble neuroendocrine cells, the immunohistochemical analysis, however, revealed a negative staining for the chromagranin A (Jongsma et al., 2000). Discrete growth mechanisms by growth factors other than androgen have been previously suggested (Koivisto et al., 1997a; 1997b), and are supported by the fact that the biological aggressive behavior and genetic expression took place in the tumor model despite the markedly reduced expression of the androgen receptor.

5.6 Example 6—Gene Therapy of Human Prostate Cancer Xenografts in Pre-Clinical Models To examine the success of the gene therapy vectors expressing HSV TKsr39 as the therapeutic gene, five therapeutic groups may be prepared. These include:
  (1) PSE or PSE-B controlling the expressing of TKsr39. This is the basal (unenhanced) expression level;
  (2) PSE-BC controlling the expression of TKsr39;
  (3) PSE-BAC controlling the expression of TKsr39. Group 2 and 3 are the enhanced level of expression;
  (4) CMV promoter controlling the expression of TKsr39. This group might achieve constitutive expression even in non-target tissue; and
  (5) Negative control group of either buffer administration or unrelated vector not expressing TK.

The inventors contemplate that the enhanced constructs (group 2,3) should achieve higher level of therapeutic gene expression in the targeted tumors than the basal constructs (group 1). Accordingly, the enhanced constructs should achieve more effective therapeutic result with improved tumor regression. The CMV group is expected to mediate high level of TK gene expression in non-targeted organ (e.g., the liver) especially after systemic delivery. In contrast, group 2 and 3 should be specifically expressed in the targeted tumors without significant expression in non-prostate tissue (e.g., the liver) even after systemic delivery. Thus the side effects of the enhanced constructs should be lower than the CMV group.

To evaluate the success of vector delivery of the genetic constructs to prostate cells, three different classes of vectors (studies 1 to 3 below): first generation adenovectors, gutless adenovectors and liposomal vectors, respectively, may be employed. As with many forms of gene delivery, different vector systems can have quite different gene transfer efficiency in vivo.

5.6.1 Gene Therapy with Intratumoral Injection of First Generation Ads

LAPC4 or LAPC9 tumor xenografts can be implanted subcutaneously in the flanks with 3 mm piece of tumor chunk in male SCID mice. When the tumors reach about 5 mm diameter (approximately $10^8$ to $10^9$ cells), 10 µl of Ad vectors may be injected intratumorally x3 sites to achieve more even vector distribution. With the usual Ad titer of $10^{11}$ infectious units/ml (pfu/ml), $10^9$ pfu x3 are delivered to the tumor. Vector administration can probably be repeated in attempt to achieve higher gene transduction. During the peak expression period, 2 to 7 days after vector administration, PET imaging may be performed to quantitate TKsr39 gene expression intratumorally as well as other non-targeted organs (e.g., liver). After gene transduction is achieved, pro-drug ganciclovir may be administered either intravenously (IV) via tail vein or intra-peritoneally (IP) at a dosage of 10 mg/kg to 100 mg/kg once daily for 6 consecutive days. Tumor sizes may be evaluated closely by accurate measurements for all the groups. Treatment side effects may be monitored by blood level of liver transaminases as indication of liver toxicity. At the end of treatment period, residual tumors or tissues may be harvested and evaluated at fine immunohistological level to document treatment efficacy.

5.6.2 Gene Therapy with Intratumoral Injection of Gutless Ads

The experimental setup may be same as in 5.6.1, except that gutless Ads may be evaluated. The PSE-BC and PSE-BAC group of vectors might expect to achieve even more specific and higher level of gene expression than first generation Ads. It is because all residual viral regulatory and coding sequences are removal thus eliminating potential interference of proper functioning of the enhanced constructs (Steinwaerder and Lieber, 2000).

5.6.3 Gene Therapy with Intratumoral Injection of Liposomal Plasmid Constructs

All 5 groups of constructs are generated in plasmid backbones (e.g., pBS, Stratagene Co.). These plasmids can be complexed with cationic lipids according to published methods (Wheeler et al, 1996) and reviewed in Li and Huang (2000). Again similar to the study shown in 5.6.1, 10 µl of liposomal DNA complex may be injected intratumorally. The administration can likely be repeated until optimal expression is achieved. The main advantage of non-viral liposomal DNA complexes is that there may be reduced concerns about immunogenicity generated by repeated administrations in patients. Moreover, limitation of plasmid DNA size may be a constraint in this system.

5.6.4 Gene Therapy to Treat Metastatic Bone Tumors by Systemic Delivery of Gutless Ad Both LAPC4 and LAPC9 tumors can be established and grown in the bone of SCID mice as a bone metastatic model for advanced human prostate cancer. Approximate $10^5$ tumor cells suspension in 2 µl may be injected at the tibial bone of SCID male mice.

When the tumors are palpable (3-5 mm dia.) requiring about 3-4 weeks after injection, 100 µl of gutless Ads ($10^9$ to $10^{10}$ gene transfer units) may be administered IV. The administration can be repeated to achieve more optimal intratumoral gene transduction. The TKsr39 gene transfer to the bone tumors can be monitored by PET imaging. Steps 4-6 are the same as described in 5.6.1.

5.6.5 Gene Therapy to Treat Metastatic Bone Tumors by Systemic Delivery of Liposomal Vectors The liposomal vectors can be delivered IV in 100 µl volume. Optimal gene transduction could be achieved by repeated administrations. Therapeutic outcomes can be evaluated as described above.

5.7 Example 7—Variations in the Sequence of the Core Enhancer Region

In addition to the particular constructs described herein, a variety of suitable enhancer core sequences may be used in the practice of the present invention. These include the sequence from 435 (BstEII site) to 822 (NcoI site) in the PSA enhancer according to Pang et al. (1997):

This sequences is:

(BstEII)

ggtgaccagagcagtctaggtggatgctgtgcaCaCggggtttgtgccactggt-
gagaaacctgagattaggaatcctcaatcttatactgggacaacttgcaaacctgc-
tcagcctttgtctctgatgaagatattatcttcatgatcttggattgaaaacagacct-
actctggaggaacatattgtatTgattgtccttgacagtaaacaaatctgttgtaag-
agacattatctttattatctaggacagtaagcaagcctggatctgagagagatatca-
tcttgcaaggatgcctgctttacaaacatccttgaaacaacaatccagaaaaaaa-
gtgttgctgtctttgctcagaagacacacagatacgtgacagaaccatggtaacc
(SEQ ID NO:62)

(NcoI/BstEII)

Other enhancer core sequences and minor variations thereof, are also expected to function with the constructs of the present invention. These include the corresponding sequence from position 1501 to 1890 Schuur et al., (1997; GenBank Acc. No. U37672):

(BstEII)

ggtgaccagagcagtctaggtggatgctgtgcagaaggggtttgtgccactggtg-
agaaacctgagattaggaatcctcaatcttatactgggacaacttgcaaacctgct-
cagcctttgtctctgatgaagatattatcttcatgatcttggattgaaaacagaccta-
ctctggaggaacatatgtatcgattgtccttgacagtaaacaaatctgttgtaagag-
acattatctttattatctaggacagtaagcaagcctggatctgagagagatatcatc-
ttgcaaggatgcctgctttacaaacatccttgaaacaacaatccagaaaaaaaag-
tgttgctgtctttgctcagaagacacacaga tacgtgacagaaccatgg (NcoI)
(SEQ ID NO:63).

Likewise, the enhancer core sequence and minor variations thereof of the glandular HK2 sequence disclosed by Yu et al., (1999; GenBank Acc. No. AF113169), which has the following corresponding sequence:

ctttgtatctgacggagatattatctttataat--tgggttgaaagcagacctactctgg
aggaacatattgtatttattgtcctgaacagtaaacaaatctgctgtaaaatagac-
gttaactttattatctaaggcagtaagcaaacctagatctgaaggcgataccatcttg-
caaggctatctgctgtacaaatatgcttgaaa (SEQ ID NO:64)

6.0 REFERENCES

The following references, to the extent that they provide exemplary procedural or other details supplementary to those set forth herein, are specifically incorporated herein by reference.

U.S. Pat. No. 4,554,101, issued Nov. 19, 1985.
U.S. Pat. No. 4,683,195, issued Sep. 8, 1992.
U.S. Pat. No. 5,145,684, issued Jun. 28, 1994.
U.S. Pat. No. 5,399,346, issued Mar. 21, 1995.
U.S. Pat. No. 5,399,363, issued Mar. 21, 1995.
U.S. Pat. No. 5,466,468, issued Nov. 14, 1995.
U.S. Pat. No. 5,472,869, issued Dec. 5, 1995.
U.S. Pat. No. 5,543,158, issued Aug. 6, 1996.
U.S. Pat. No. 5,552,157, issued Sep. 3, 1996.
U.S. Pat. No. 5,565,213, issued Oct. 15, 1996.
U.S. Pat. No. 5,567,434, issued Oct. 22, 1996.
U.S. Pat. No. 5,641,515, issued Jun. 24, 1997.
U.S. Pat. No. 5,738,868, issued Apr. 14, 1998.
U.S. Pat. No. 5,741,516, issued Apr. 21, 1998.
U.S. Pat. No. 5,795,587, issued Aug. 18, 1998.
U.S. Pat. No. 5,874,265, issued Feb. 23, 1999.
U.S. Pat. No. 6,110,702, issued Aug. 29, 2000.
European Patent Application Publication No. EP 0273085.
Intl. Pat. Appl. Publ. No. WO 96/14875.

Adam, Ramesh, Miller and Osborne, "Internal initiation of translation in retroviral vectors carrying picornavirus 5' nontranslated regions," *J. Virol.*, 65:4985-4990, 1991.

Alemany, Gomez-Manzano, Balague, Yung, Curiel, Kyritsis and Fueyo, "Gene therapy for gliomas: molecular targets, adenoviral vectors, and oncolytic adenoviruses," *Exp. Cell Res.*, 252:1-12, 1999.

Allen and Choun, "Large unilamellar liposomes with low uptake into the reticuloendothelial system," *FEBS Lett.*, 223:42-46, 1987.

Anderson, *Nature*, 392:25-30, 1998.

Anderson, Swaminathan, Zackon, Tajuddin, Thimmapaya and Weitzman, "Adenovirus-mediated tissue-targeted expression of the HSVtk gene for the treatment of breast cancer," *Gene Ther.*, 6:854-864, 1999.

Ashkenazi, Pai, Fong, Leung, Lawrence, Marsters, Blackie, Chang, McMurtrey, Hebert, DeForge, Koumenis, Lewis, Harris, Bussiere, Koeppen, Shahrokh and Schwall, "Safety and antitumor activity of recombinant soluble Apo2 ligand," *J. Clin. Invest.*, 104:155-162, 1999.

Aumüller, Seitz, Lilja, Abrahamsson, von der Kammer and Scheit, "Species- and organ-specificity of secretory proteins derived from human prostate and seminal vesicles," *Prostate*, 17:31-40, 1990.

Balazsovits et al., "Analysis of the effect of liposome encapsulation on the vesicant properties, acute and cardiac toxicities, and antitumor efficacy of doxorubicin," *Cancer Chemother. Pharmacol.*, 23:81-86, 1989.

Benvenisty and Reshef, "Direct introduction of genes into rats and expression of the genes," *Proc. Natl. Acad. Sci. USA.;* 83(24): 9551-9555, 1986.

Bonavida, Ng, Jazirehi, Schiller and Mitutani, "Selectivity of TRAIL-mediated apoptosis of cancer cells and synergy with drugs: The trail to non-toxic cancer therapeutics (review)," *Int. J. Oncol.*, 15:793-802, 1999.

Bonham et al., "An assessment of the antisense properties of RNase H-competent and steric-blocking oligomers," *Nucleic Acids Res* 1995 Apr. 11; 23(7):1197-1203, 1995.

Bruhn, Munnerlyn and Grosschedl, "ALY, a context-dependent coactivator of LEF-1 and AML-1, is required for TCR alpha enhancer function," *Genes and Dev.*, 11:640-653, 1997.

Capecchi, "High efficiency transformation by direct microinjection of DNA into cultured mammalian cells," *Cell*, 22(2):479-488, 1980.

Cardillo, Berchem, Tarkington, Krajewski, Krajewski, Reed, Tehan, Ortega, Lage and Gelmann, "Resistance to apoptosis and upregulation of Bcl-2 in benign prostatic hyperplasia after androgen deprivation," *J. Urol.*, 145:12-16, 1997.

Carey, "The enhanceosome and transcriptional synergy," *Cell*, 92:5-8, 1998.

Catalona, Smith, Ratliff, Dodds, Coplen, Yuan, Petros, Andriole, et al., "Measurement of prostate-specific antigen in serum as a screening test for prostate cancer," *N. Engl. J. Med.*, 324:1156-1161, 1991.

Cavailles, Dauvois, L'Horset, Lopez, Hoare, Kushner and Parker, *EMBO J*, 14:3741-3751, 1995.

Cepek, Chasman and Sharp, *Genes Dev.*, 10:2079-2088, 1996.

Chakravarti, LaMorte, Nelson, Nakajima, Schulman, Juguilon, Montminy and Evans, *Nature*, 383:99-103, 1996.

Chamberlain, Whitacre and Miesfeld, *J. Biol. Chem.*, 271: 26772-26778, 1996.

Chandran, Roy, Mishra, "Recent trends in drug delivery systems: Liposomal drug delivery system—preparation and characterisation," *Indian J. Exp. Biol.*, 35(8):801-809, 1997.

Chang, Kokontis and Liao, *Proc. Natl. Acad. Sci. USA*, 85:7211-7215, 1988b.

Chang, Kokontis and Liao, *Science*, 240:324-326, 1988a.

Chang, Saltzman, Yeh, Young, Keller, Lee, Wang and Mizokami, *Crit. Rev. Eukaryotic Gene Expr.*, 5:97-125, 1995.

Chang, Wang, DeLuca, Ross and Shih, *Proc. Natl. Acad. Sci. USA*, 89:5946-5950, 1992.

Chappell, Edelman and Mauro, "A 9-nt segment of a cellular mRNA can function as an internal ribosome entry site (IRES) and when present in linked multiple copies greatly enhances IRES activity," *Proc. Natl. Acad. Sci. USA*, 97:1536-1541, 2000.

Chen and Okayama, "High-efficiency transformation of mammalian cells by plasmid DNA," *Mol. Cell. Biol.*, 7:2745-2752, 1987.

Cheng, Sebo, Cheville, Pisansky, Slezak, Bergstralh, Pacelli, Neumann, Zincke and Bostwick, "p53 protein overexpression is associated with increased cell proliferation in patients with locally recurrent prostate carcinoma after radiation therapy," *Cancer*, 85:1293, 1999.

Cheng, Sun, Pretlow, Culp and Yang, *J. Natl. Cancer Inst.*, 88:607-611, 1996.

Chi, Lieberman, Ellwood and Carey, *Nature*, 377:254-257, 1995.

Chomczynski and Sacchi, "Single step method of RNA isolation by acid guanidinium thio-cyanate-phenol-chloroform extraction," *Anal. Biochem.*, 162:156-159, 1987.

Christensen, Johansen, Marker, Thomsen, "Circulating intracellular adhesion molecule-1 (ICAM-1) as an early and sensitive marker for virus-induced T cell activation," *Clin. Exp. Immunol.*, 102(2):268-273, 1995.

Chung, "Implications of stroma-epithelial interaction in human prostate cancer growth, progression and differentiation," *Cancer Biology*, 4:183, 1993.

Claessens, Alen, Devos, Peeters, Verhoeven and Rombauts, *J. Biol. Chem.*, 271:19013-19016, 1996.

Cleutjens, van der Korput, Ehren-van Eekelen, Sikes, Fasciana, Chung and Trapman, "A 6-kb promoter fragment mimics in transgenic mice the prostate-specific and androgen-regulated expression of the endogenous prostate-specific antigen gene in humans," *Mol. Endocrinol.*, 11:1256-1265, 1997b.

Cleutjens, van der Korput, van Eekelen, van Rooij, Faber and Trapman, "An androgen response element in a far upstream enhancer region is essential for high, androgen-regulated activity of the prostate-specificantigen promoter," *Mol. Endocrinol.*, 11: 148-161, 1997a.

Cleutjens, van Eekelen, van der Korput, Brinkmann and Trapman, "Two androgen response regions cooperate in steroid hormone regulated activity of the prostate-specific antigen promoter," *J. Biol. Chem.*, 271:6379-6388, 1996.

Coffin, "Retroviridae and their replication," In: *Virology*, Fields et al., Eds., New York, Raven Press, pp. 1437-1500, 1990.

Collins and Hohn, "Cosmids: a type of plasmid gene-cloning vector that is packageable in vitro in bacteriophage lambda heads," *Proc. Natl. Acad. Sci. USA*, 75:4242-4246, 1978.

Corey, "Peptide nucleic acids: expanding the scope of nucleic acid recognition," *Trends Biotechnol.*, 15(6):224-229, 1997.

Coune, "Liposomes as drug delivery system in the treatment of infectious diseases: potential applications and clinical experience," *Infection*, 16(3):141-147, 1988.

Coupar et al., "A general method for the construction of recombinant vaccinia virus expressing multiple foreign genes," *Gene*, 68:1-10, 1988.

Couvreur et al., "Nanocapsules, a new lysosomotropic carrier," *FEBS Lett.*, 84:323-326, 1977.

Couvreur et al., "Tissue distribution of antitumor drugs associated with polyalkylcyanoacrylate nanoparticles," *J. Pharm. Sci.*, 69(2):199-202, 1980.

Couvreur, "Polyalkyleyanoacrylates as colloidal drug carriers," *Crit. Rev. Ther. Drug Carrier Syst.*, 5:1-20, 1988.

Craft, Shostak, Carey and Sawyers, "A mechanism for hormone-independent prostate cancer through modulation of androgen receptor signaling by the HER-2/neu tyrosine kinase," *Nat. Med.*, 5:280-85, 1999.

Cunningham et el., *Can. Res.*, 56:4475-4482, 1996.

Curiel, Agarwal, Wagner, Cotten, "Adenovirus enhancement of transferrin-polylysine-mediated gene delivery," *Proc. Natl. Acad. Sci. USA*, 88(19):8850-8854, 1991.

De Vos, Schmitt, Verhoeven and Stunnenberg, *Nucleic Acids Res.*, 22:1161-1166, 1994.

Deguchi, Doi, Ehara, Ito, Takahashi, Nishino, Fujihiro, Kawamura, Komeda, Horie, et al., "Detection of micrometastatic prostate cancer cells in lymph nodes by reverse transcriptase-polymerase chain reaction," *Cancer Res.*, 53:5350-5354, 1993.

Dignam, Lebovitz and Roeder, *Nucleic Acids Res.*, 11:1475-1489, 1983.

DiPaola and Aisner, "Overcoming bcl-2- and p53-mediated resistance in prostate cancer," *Semin. Oncol.*, 26(1 Suppl 2):112, 1999.

Doesburg, Kuil, Berrevoets, Steketee, Faber, Mulder, Brinkmann and Trapman, *Biochemistry*, 36:1052-1064, 1997.

Douglas, Davis, Illum, "Nanoparticles in drug delivery," *Crit. Rev. Ther. Drug Carrier Syst.*, 3(3):233-261, 1987.

Dubensky et al., "Direct transfection of viral and plasmid DNA into the liver or spleen of mice," *Proc. Nat. Acad. Sci. USA*, 81:7529-7533, 1984.

Dueholm, Motawia, Pedersen, Nielsen, Lundt, "Synthesis of 3'-alkylthio-2',3'-dideoxy nucleosides with potential anti-HIV activity from 2-deoxy-D-ribose, using a phosphorus pentoxide reagent," *Arch. Pharm. (Weinheim)*, 325(9):597-601, 1992.

Eglitis and Anderson, "Retroviral vectors for introduction of genes into mammalian cells," *Biotechniques* 6(7):608-614, 1988.

Emami and Carey, *EMBO J.*, 11:5005-5012, 1992.

Evans, *Science*, 240:889-895, 1988.

Faller and Baltimore, "Liposome encapsulation of retrovirus allows efficient super infection of resistant cell lines," *J. Virol.*, 49(1):269-272, 1984.

Falvo, Thanos and Maniatis, "Reversal of intrinsic DNA bends in the IFN beta gene enhancer by transcription factors and the architectural protein HMG I(Y)," *Cell*, 83:1101-1111, 1995.

Fechheimer et al., "Transfection of mammalian cells with plasmid DNA by scrape loading and sonication loading," *Proc. Natl. Acad. Sci. USA*, 84:8463-8467, 1987.

Ferkol, Lindberg, Chen, Perales, Crawford, Ratnoff, Hanson, "Regulation of the phosphoenolpyruvate carboxykinase/human factor IX gene introduced into the livers of adult rats by receptor-mediated gene transfer," *FASEB J.*, 7(11):1081-1091, 1993.

Fondell, Ge and Roeder, *Proc. Natl. Acad. Sci. USA*, 93:8329-8333, 1996.

Fraley et al., "Entrapment of a bacterial plasmid in phospholipid vesicles: Potential for gene transfer," *Proc. Natl. Acad. Sci. USA*, 76:3348-3352, 1979.

Fresta and Puglisi, "Application of liposomes as potential cutaneous drug delivery systems. In vitro and in vivo investigation with radioactively labelled vesicles," *J. Drug Target*, 4(2):95-101, 1996.

Friedmann, "Progress toward human gene therapy," *Science*, 244:1275-1281, 1989.

Fromm, Taylor, Walbot, "Expression of genes transferred into monocot and dicot plant cells by electroporation," *Proc. Natl. Acad. Sci. USA*, 82(17):5824-5828, 1985.

Gabizon and Papahadjopoulos, "Liposomes formulations with prolonged circulation time in blood and enhanced uptake by tumors," *Proc. Natl. Acad. Sci. USA*, 85:6949-6953, 1988.

Gaddipati, McLeod, Heidenberg, Sesterhenn, Finger, Moul and Srivastava, "Frequent detection of codon 877 mutation in the androgen receptor gene in advanced prostate cancers," *Cancer Res.*, 54:2861-2864, 1994.

Gambhir, Barrio, Phelps, Iyer, Namavari, Satyamurthy, Wu, Green, Bauer, MacLaren, Nguyen, Berk, Chemy and Herschman, "Imaging adenoviral-directed reporter gene expression in living animals with positron emission tomography," *Proc. Natl. Acad. Sci. USA*, 96:2333-2338, 1999.

Gambhir, Barrio, Wu, Iyer, Namavari, Satyamurthy, Bauer, Parrish, MacLaren, Borghei, Green, Sharfstein, Berk, Chemy, Phelps and Herschman, "Imaging of Adenoviral Directed Herpes Simplex Virus Type 1 Thymidine Kinase Gene Expression in Mice with Ganciclovir," *J. Nucl. Med.*, 39:2003-2011, 1998.

Gambhir, Bauer, Black, Liang, Kokoris, Barrio, Iyer, Namavari, Phelps and Herschman, "A mutant herpes simplex virus type 1 thymidine kinase reporter gene shows improved sensitivity for imaging reporter gene expression with positron emission tomography," *Proc. Natl. Acad. Sci. USA*, 97:2785-2790, 2000.

Gao, Ossowski and Ferrari, "Activation of Rb and decline in adrogen receptor protein precede retinoic acid-induced apoptosis in androgen-dependent LNCaP cells and their androgen-independent derivative," *J. Cell. Physiol.*, 179:336, 1999.

Ghattas, Sanes and Majors, "The encephalomyocarditis virus internal ribosome entry site allows efficient coexpression of two genes from a recombinant provirus in cultured cells and in embryos," *Mol. Cell Biol.*, 11:5848-5859, 1991.

Ghosh and Bachhawat, "Targeting of liposomes to hepatocytes," In: *Liver diseases, targeted diagnosis and therapy using specific receptors and ligands*, Wu and Wu Eds., New York, Marcel Dekker, pp. 87-104, 1991.

Glass, Rose and Rosenfeld, *Curr. Opin. Cell Biol.*, 9:222-232, 1997.

Gomez-Foix et al., "Adenovirus-mediated transfer of the muscle glycogen phosphorylase gene into hepatocytes confers altered regulation of glycogen metabolism," *J. Biol. Chem.*, 267(35):25129-25134, 1992.

Good and Nielsen, "Progress in developing PNA as a gene-targeted drug," *Antisense Nucl. Acid Drug Dev.*, 7(4):431-437, 1997.

Gopal, "Gene transfer method for transient gene expression, stable transfection, and cotransfection of suspension cell cultures," *Mol. Cell. Biol.*, 5:1188-1190, 1985.

Gotoh, Ko, Shirakawa, Cheon, Kao, Miyamoto, Gardner, Ho, Cleutjens, Trapman, Graham and Chung, "Development of prostate-specific antigen promoter-based gene therapy for androgen-independent human prostate cancer," *J. Urol.*, 160:220-229, 1998.

Graham and Prevec, "Adenovirus-based expression vectors and recombinant vaccines," *Biotechnology*, 20:363-390, 1992.

Graham and van der Eb, "Transformation of rat cells by DNA of human adenovirus 5," *Virology*, 54(2):536-539, 1973.

Grossfeld, Olumi, Connolly, Chew, Gibney, Bhargava, Waldman and Carroll, "Locally Recurrent Tumors Following Either Radiation Therapy or Radical Prostatectomy Have Changes in Ki-67 Labeling Index, p53 and bcl-2 Immunoreactivity," *J. Urol.*, 159:1437, 1998.

Grunhaus and Horwitz, "Adenovirus as cloning vector," *Sem. in Virol.*, 3:237-252, 1992.

Guo and Kyprianou, "Overexpression of transforming growth factor (TGF) beta 1 type II receptor restores TGF-beta1 sensitivity and signaling in human prostate cancer cells," *Cell Growth and Diff.*, 9:185, 1988.

Hanvey, Peffer, Bisi, Thomson, Cadilla, Josey, Ricca, Hassman, Bonham, Au, et al., "Antisense and antigene properties of peptide nucleic acids," *Science*, 258(5087):1481-1485, 1992.

Hardy, Kitamura, Harris-Stansil, Dai and Phipps, "Construction of adenovirus vectors through Cre-lox recombination," *J. Virol.*, 71:1842-1849, 1997.

Harland and Weintraub, "Translation of mammalian mRNA injected into *Xenopus* oocytes is specifically inhibited by antisense RNA," *J. Cell Biol.*, 101:1094-1099, 1985.

Heath and Martin, "The development and application of protein-liposome conjugation techniques," *Chem. Phys. Lipids*, 40:347-358, 1986.

Heath et al., "Liposome-mediated delivery of pteridine antifolates to cells: in vitro potency of methotrexate and its alpha and gamma substituents," *Biochim. Biophys. Acta,* 862:72-80, 1986.

Henry-Michelland et al., "Attachment of antibiotics to nanoparticles; Preparation, drug-release and antimicrobial activity in vitro," *Int. J. Pharm.,* 35:121-127, 1987.

Herman, Adler, Aguilar-Cordova, Rojas-Martinez, Woo, Timme, Wheeler, Thompson and Scardino, "In situ gene therapy for adenocarcinoma of the prostate: a phase I clinical trial," *Human Gene Therapy,* 10:1239-1249, 1999.

Hermonat and Muzyczka, "Use of adenoassociated virus as a mammalian DNA cloning vector: Transduction of neomycin resistance into mammalian tissue culture cells," *Proc. Natl. Acad. Sci. USA,* 81:6466-6470, 1984.

Herz and Gerard, "Adenovirus-mediated transfer of low density lipoprotein receptor gene acutely accelerates cholesterol clearance in normal mice," *Proc. Natl. Acad. Sci. USA* 90:2812-2816, 1993.

Herz and Girard, "Adenovirus mediated transfer of lipoprotein receptor gene acutely accelerates cholesterol clearance in normal mice," *Proc. Natl. Acad. Sci. USA,* 90:2812-2816, 1993.

Hitt et al., *Methods Mol. Genet.,* 7:13-30, 1995.

Hitt, Bett, Addison, Prevec and Graham, "Techniques for human adenovirus vector construction and characterization," *Methods Mol. Genet.,* 7:13-30, 1995.

Hollenberg, Weinberger, Ong, Cerelli, Oro, Lebo, Thompson, Rosenfeld and Evans, *Nature,* 318:635-641, 1985.

Hong, Kohli, Trivedi, Johnson and Stallcup, *Proc. Natl. Acad. Sci. USA,* 93:4948-4952, 1996.

Hoover et al., Eds., "Remington's Pharmaceutical Sciences," 15th Edition, Mack Publishing Co., Easton, Pa., pp. 1035-1038 and 1570-1580, 1975.

Hori and Carey, *Curr. Opin. Genet. & Dev.,* 4:236-244, 1994.

Horoszewicz, Leong, Kawinski, Karr, Rosenthal, Chu, Mirand and Murphy, "LNCaP model of human prostatic carcinoma," *Cancer Res.,* 43:1809, 1983.

Horwich et al. "Synthesis of hepadenovirus particles that contain replication-defective duck hepatitis B virus genomes in cultured HuH7 cells," *J. Virol.,* 64:642-650, 1990.

Huang, Shostak, Tarr, Sawyers and Carey, "Cooperative assembly of androgen receptor into a nucleoprotein complex that regulates the prostate-specific antigen enhancer," *J. Biol. Chem.,* 274:25756-25768, 1999.

Hyrup and Nielsen, "Peptide nucleic acids (PNA): synthesis, properties and potential applications," *Bioorg. Med. Chem.,* 4(1):5-23, 1996.

Imaizumi et al., "Liposome-entrapped superoxide dismutase ameliorates infarct volume in focal cerebral ischemia," *Acta. Neurochirurgica Suppl.,* 51:236-238, 1990b.

Imaizumi et al., "Liposome-entrapped superoxide dismutase reduces cerebral infarction in cerebral ischemia in rats," *Stroke,* 21(9):1312-1317, 1990a.

Ing, Beekman, Tsai, Tsai and O'Malley, *J. Biol. Chem.,* 267:17617-17623, 1992.

Jacq, Brou, Lutz, Davidson, Chambon and Tora, *Cell,* 79:107-117, 1994.

Jang, Davies, Kaufman and Wimmer, "Initiation of protein synthesis by internal entry of ribosomes into the 5' non-translated region of encephalomyocarditis virus RNA in vivo," *J. Virol.,* 63:1651-1660, 1989.

Jones, Mettlin, Murphy et al., "Patterns of care for carcinoma of the prostate gland: Results of a national survey of 1984 and 1990," *J. Am. Coll. Surg.,* 180:545, 1995.

Jongsma, Oomen, Noordzij, Romijn, van Der Kwast, Schroder and van Steenbrugge, "Androgen-independent growth is induced by neuropeptides in human prostate cancer cell lines," *Prostate,* 42:34, 2000.

Jooss, Yang, Fisher and Wilson, "Transduction of dendritic cells by DNA viral vectors directs the immune response to transgene products in muscle fibers," *J. Virol.,* 72:4212-4223, 1998.

Kallio, Palvimo, Mehto and Janne, *J. Biol. Chem.,* 269:11514-11522, 1994.

Kaneda, Iwai, Uchida, "Introduction and expression of the human insulin gene in adult rat liver," *J. Biol. Chem.,* 264(21):12126-12129, 1989.

Kang, Martins and Sadowski, *J. Biol. Chem.,* 268:9629-9635, 1993.

Kasper, Rennie, Bruchovsky, Sheppard, Cheng, Lin, Shiu, Snoek and Matusik, *J. Biol. Chem.,* 269:31763-31769, 1994.

Kato et al., "Expression of hepatitis β virus surface antigen in adult rat liver," *J. Biol. Chem.,* 266:3361-3364, 1991.

Kim, Lin, Barr, Chu, Leiden and Parmacek, "Transcriptional targeting of replication-defective adenovirus transgene expression to smooth muscle cells in vivo," *J. Clin. Invest.,* 100:1006-1014, 1997.

Kim, Qin, Gong, Stevens, Luo, Nussenzweig and Roeder, *Nature,* 383:542-547, 1996.

Klein, Kornstein, Sanford, Fromm, *Nature,* 327:70-73, 1987.

Klein, Reiter, Redulla, Moradi, Zhu, Brothman, Lamb, Marcelli, Belldegrun, Witte and Sawyers, "Progression of metastatic human prostate cancer to androgen independence in immunodeficient SCID mice," *Nat. Med.,* 3:402-408, 1997.

Klein, Wolf, Wu, Sanford, "High-velocity microprojectiles for delivering nucleic acids into living cells. 1987," *Biotechnology,* 24:384-386, 1992.

Klobeck et al., *Nucl. Acids Res.,* 17:3981, 1989.

Koivisto, Kononen, Palmberg, Tammela, Hyytinen, Isola, Trapman, Cleutjens, Noordzij, Visakorpi and Kallioniemi, "Androgen receptor gene amplification: a possible molecular mechanism for androgen deprivation therapy failure in prostate cancer," *Cancer Res.,* 57:314-319, 1997a.

Koivisto, Visakorpi, Rantala and Isola, "Increased cell proliferation activity and decreased cell death are associated with the emergence of hormone refractory recurrent prostate cancer," *J. Pathol.,* 183:51, 1997b.

Krysan, Haase and Calos, "Isolation of human sequences that replicate autonomously in human cells," *Mol. Cell. Biol.,* 9:1026-1033, 1989.

Kuiper, de Ruiter, Trapman, Boersma, Grootegoed and Brinkmann, *Biochem. J,* 291:95-101, 1993.

Kyte and Doolittle, 1982.

Langley, Zhou and Wilson, *J. Biol. Chem.,* 270:29983-29990, 1995.

Lasic, "Novel applications of liposomes," *Trends Biotechnol.,* 16(7):307-321, 1998.

Latham, Searle, Mautner and James, "Prostate-specific antigen promoter/enhancer driven gene therapy for prostate cancer: construction and testing of a tissue-specific adenovirus vector," *Cancer Research,* 60:334-341, 2000.

Le Gal La Salle et al., "An adenovirus vector for gene transfer into neurons and glia in the brain," *Science,* 259:988-990, 1993.

Lee, Jin, Lee, Yoon, Park, Heo and Choi, "Development of a new plasmid vector with PSA-promoter and enhancer expressing tissue-specificity in prostate carcinoma cell lines," *Anticancer Research,* 20:417-422, 2000.

Lefstin and Yamamoto, *Nature,* 392:885-888, 1998.

Levrero et al., "Significance of anti-HBx antibodies in hepatitis B virus infection," *Hepatology,* 13(1):143-149, 1991.

Li and Huang, *Gene Ther.,* 7:31-34, 2000.

Lieber, He, Kirillova and Kay, "Recombinant adenoviruses with large deletions generated by Cre-mediated excision exhibit different biological properties compared with first-generation vectors in vitro and in vivo," *J. Virol.,* 70:8944-8960, 1996.

Limonta, Dondi, Marelli, Moretti, Negri-Cesi and Motta, *J. Steroid Biochem. Mol. Biol.,* 53:401-405, 1995.

Lopez-Berestein et al., "Liposomal amphotericin B for the treatment of systemic fungal infections in patients with cancer: a preliminary study" *J. Infect. Dis.,* 2151:704, 1985a.

Lopez-Berestein et al., "Protective effect of liposomal-amphotericin B against *C. albicans* infection in mice," *Cancer Drug Delivery,* 2:183, 1985b.

Lu, Carraher, Zhang, Armstrong, Lerner, Rogers and Steiner, "Delivery of adenoviral vectors to the prostate for gene therapy," *Cancer Gene Ther.,* 6:64-72, 1999.

Lubahn, Joseph, Sar, Tan, Higgs, Larson, French and Wilson, *Mol. Endocrinol.,* 2:1265-1275, 1988.

Luke and Coffey, "Human androgen receptor binding to the androgen response element of prostate specific antigen," *J. Androl.,* 15:41-51, 1994.

Lundwall, *Biophys. Biochem. Res. Comm.,* 161:1151-1159, 1989.

MacDonald and Habib, "Divergent responses to epidermal growth factor in hormone sensitive and insensitive human prostate cancer cell lines," *Br. J. Cancer,* 65:177, 1992.

MacLaren, Gambhir, Satyamurthy, Barrio, Sharfstein, Toyokuni, Wu, Berk, Chemy, Phelps and Herschman, "Repetitive, non-invasive imaging of the dopamine D2 receptor as a reporter gene in living animals," *Gene Ther.,* 6:785-791, 1999.

Margalit, "Liposome-mediated drug targeting in topical and regional therapies," *Crit. Rev. Ther. Drug Carrier Syst.,* 12(2-3):233-261, 1995.

McDonnell, Navone, Troncoso, Pisters, Conti, von Eschenbach, Brisbay and Logothetis, "Expression of bcl-2 oncoprotein and p53 protein accumulation in bone marrow metastases of androgen independent prostate cancer," *J. Urol.,* 157:569, 1997.

McDonnell, Troncoso, Brisbay, Logothetis, Chung, Hsieh, Tu and Campbell, "Expression of proto-oncogene bcl-2 in the prostate and its association with emergence of androgen-independent prostate cancer," *Cancer Res.,* 52:6940, 1992.

McEwan and Gustafsson, *Proc. Natl. Acad. Sci. USA,* 94:8485-8490, 1997.

Misrahi, Atger, D'Auriol, Loosfelt, Meriel, Fridlansky, Guiochon-Mantel, Galibert and Milgrom, *Biochem. Biophys. Res. Commun.,* 143:740-748, 1987.

Mocellini et al., *Prostate,* 22:291, 1993.

Mori and Fukatsu, "Anticonvulsant effect of DN-1417 a derivative of thyrotropin-releasing hormone and liposome-entrapped DN-1417 on amygdaloid-kindled rats," *Epilepsia,* 33(6):994-1000, 1992.

Morsy, Gu, Motzel, Zhao, Lin, Su, Allen, Franlin, Parks, Graham, Kochanek, Bett and Caskey, "An adenoviral vector deleted for all viral coding sequences results in enhanced safety and extended expression of a leptin transgene," *Proc. Natl. Acad. Sci. USA,* 95:7866-7871, 1998.

Muller et al., "Efficient transfection and expression of heterologous genes in PC12 cells," *Cell, Biol.,* 9(3):221-229, 1990.

Muller, Young, Pendergast, Pondel, Landau, Littman and Witte, *Mol. Cell. Biol.,* 11:1785-1792, 1991.

Muzyczka and McLaughlin, "Use of adeno-associated virus as a mammalian transduction vector," In: *Current Communications in Molecular Biology: Viral Vectors,* Glzman and Hughes, Eds., Cold Spring Harbor Laboratory Press, Cold Spring Harbor, N.Y., pp. 39-44, 1988.

Navarro, Millecamps, Geoffroy, Robert, Valin, Mallet and Gal La Salle, "Efficient gene transfer and long-term expression in neurons using a recombinant adenovirus with a neuron-specific promoter," *Gene Ther.,* 6:1884-1892, 1999.

Newling, "The management of hormone refractory prostate cancer," *Eur. Urol.,* 29:69-74, 1996.

Nicolau and Gersonde, "Incorporation of inositol hexaphosphate into intact red blood cells, I. fusion of effector-containing lipid vesicles with erythrocytes," *Naturwissenschaften* (Germany), 66(11):563-566, 1979.

Nicolau and Sene, "Liposome-mediated DNA transfer in eukaryotic cells," *Biochem. Biophys. Acta,* 721:185-190, 1982.

Nicolau et al., "Liposomes as carriers for in vivo gene transfer and expression," *Methods Enzymol.,* 149:157-176, 1987.

Nielsen et al., "DNA analogues with nonphosphodiester backbones," *Annu. Rev. Biophys. Biomol. Struct.,* 24:167-183, 1995.

Nielsen, DiGiovanni, Christensen, Knepper, Harris, "Cellular and subcellular immunolocalization of vasopressin-regulated water channel in rat kidney," *Proc. Natl. Acad. Sci. USA,* 90(24):11663-11667, 1993.

Norton, Waggenspack, Varnum, Corey, "Targeting peptide nucleic acid-protein conjugates to structural features within duplex DNA," *Bioorg. Med. Chem.,* 3(4):437-445, 1995.

Oettgen, Finger, Sun, Akbarali, Thamrongsak, Boltax, Grall, Dube, Weiss, Brown, Quinn, Kas, Endress, Kunsch and Libermann, "PDEF, a novel prostate epithelium-specific ets transcription factor, interacts with the androgen receptor and activates prostate-specific antigen gene expression," *J. Biol. Chem.,* 275:1216-1225, 2000.

Onate, Tsai, Tsai and O'Malley, *Science,* 270:1354-1357, 1995.

Pang et al., *Hum. Gene Ther.,* 6:1417-1426, 1995.

Pang, Dannull, Kaboo, Xie, Tso, Michel, deKernion and Belldegrun, "Identification of a positive regulatory element responsible for tissue-specific expression of prostate-specific antigen," *Cancer Res.,* 57:495-499, 1997.

Pang, Taneja, Dardashti, Cohan, Kaboo, Sokoloff, Tso, Dekernion and Belldegrun, "Prostate tissue specificity of the prostate-specific antigen promoter isolated from a patient with prostate cancer," *Hum. Gene Ther.,* 6:1417-1426, 1995.

Parks and Graham, "A helper-dependent system for adenovirus vector production helps define a lower limit for efficient DNA packaging," *J. Virol.,* 71:3293-3298, 1997.

Parks, Bramson, Wan, Addison and Graham, "Effects of stuffer DNA on transgene expression from helper-dependent adenovirus vectors," *J. Virol.,* 73:8027-8034, 1999.

Parks, Chen, Anton, Sankar, Rudnicki and Graham, "A helper-dependent adenovirus vector system: Removal of helper virus by Cre-mediated excision of the viral packaging signal," *PNAS,* 93:13565-13570, 1996.

Passaniti, Isaacs, Haney, Adler, Cujdik, Long and Kleinman, "Stimulation of human prostatic carcinoma tumor growth in athymic mice and control of migration in culture by extracellular matrix," *Int. J. Cancer,* 51:318, 1992.

Pastore, Morral, Zhou, Garcia, Parks, Kochanek, Graham, Lee and Beaudet, "Use of a liver-specific promoter reduces immune response to the transgene in adenoviral vectors," *Hum. Gene Ther.,* 10:1773-1781, 1999.

Patel, Zisman, Pantuck, Tsui, Paik, Caliliw, Sheriff, Wu, deKernion, Tso and Belldegrun, "CL1-GFP: an androgen independent metastatic tumor model for prostate cancer," *J. Urol.,* 164(4):1420-1425, 2000.

Paul, Ewing, Jarrard and Isaacs, "The cadherin cell-cell adhesion pathway in prostate cancer progression," *Br. J. Urol.,* 79:supp 37, 1997.

Pearson and Lipman, *Proc. Natl. Acad. Sci. USA.,* 85:2444-2448, 1988.

Perales et al., *Proc. Natl. Acad. Sci. USA,* 91:4086-4090, 1994.

Pikul et al., "In vitro killing of melanoma by liposome-delivered intracellular irradiation, *Arch. Surg.,* 122(12): 1417-1420, 1987.

Pinto-Alphandary, Balland, Couvreur, "A new method to isolate polyalkylcyanoacrylate nanoparticle preparations," *J. Drug Target,* 3(2):167-169, 1995.

Potter et al., "Enhancer-dependent expression of human κ immunoglobulin genes introduced into mouse pre-B lymphocytes by electroporation," *Proc. Natl. Acad. Sci. USA,* 81:7161-7165, 1984.

Pretlow, Delmoro, Dilley, Spadafora and Pretlow, "Transplantation of human prostatic carcinoma into nude mice in matrigel," *Cancer Res.,* 51:3814, 1991.

Quintanar-Guerrero, Allemann, Doelker, Fessi, "Preparation and characterization of nanocapsules from preformed polymers by a new process based on emulsification-diffusion techinque," *Phamr. Res.,* 15(7): 1056-1062, 1998.

Rachez, Suldan, Ward, Chang, Burakov, Erdjument-Bromage, Tempst and Freedman, *Genes Dev.,* 12:1787-1800, 1998.

Raffo, Perlman, Chen, Day, Streitman and Buttyan, "Overexpression of bcl-2 protects prostate cancer cells from apoptosis in vitro and confers resistance to androgen depletion in vitro," *Cancer Res.,* 55:4438, 1995.

Ragot et al., "Efficient adenovirus-mediated transfer of a human minidystrophin gene to skeletal muscle of mdx mice," *Nature,* 361:647-650, 1993.

Renneisen et al., "Inhibition of expression of human immunodeficiency virus-1 in vitro by antibody-targeted liposomes containing antisense RNA to the env region," *J. Biol. Chem.,* 265(27):16337-16342, 1990.

Rich et al., "Development and analysis of recombinant adenoviruses for gene therapy of cystic fibrosis," *Hum. Gene Ther.,* 4:461-476, 1993.

Richmond, Karayiannakis, Nagafuchi, Kaisary, Pignatelli, "Aberrent E-cadherin and alpha-catenin expression in prostate cancer: correlation with patient survival," *Cancer Res.,* 57:3189, 1997.

Ridgeway, "Mammalian expression vectors," In: *Vectors: A survey of molecular cloning vectors and their uses,* Rodriguez R L, Denhardt D T, ed., Stoneham: Butterworth, pp. 467-492, 1988.

Riegman, Vlietstra, van der Korput, Brinmann and Trapman, "The promoter of the prostate-specific antigen gene contains a functional androgen responsive element," *Mol. Endocrinology,* 5:1921-1930, 1991.

Rippe et al., "DNA-mediated gene transfer into adult rat hepatocytes in primary culture," *Mol. Cell. Biol.,* 10:689-695, 1990.

Rodriguez, Schuur, Lim, Henderson, Simons and Henderson, "Prostate attenuated replication competent adenovirus (ARCA) CN706: a selective cytotoxic for prostate-specific antigen-positive prostate cancer cells," *Cancer Res.,* 57:2559-2563, 1997.

Rosenfeld et al., "Adenovirus-mediated transfer of a recombinant al-antitrypsin gene to the lung epithelium in vivo," *Science,* 252:431-434, 1991.

Rosenfeld et al., "In vivo transfer of the human cystic fibrosis transmembrane conductance regulator gene to the airway epithelium," *Cell,* 68:143-155, 1992.

Rundlett, Wu and Miesfeld, *Mol. Endocrinol.,* 4:708-714, 1990.

Russell, Bennett and Stricker, "Growth factor involvement in progression of prostate cancer," *Clin. Chem.,* 44:705, 1998.

Sadar, "Androgen-independent induction of prostate-specific antigen gene expression via cross-talk between the androgen receptor and protein kinase A signal transduction pathways," *J. Biol. Chem.,* 274:7777-7783, 1999.

Sadovsky, Webb, Lopez, Baxter, Fitzpatrick, Gizang-Ginsberg, Cavailles, Parker and Kushner, *Mol. Cell. Biol.,* 15:1554-1563, 1995.

Sawyers, Callahan and Witte, *Cell,* 70:901-910, 1992.

Schaffner, Barrios, Shaker, Rajagopalan, Huang, Tindall, Young, Overbeek, Lebovitz and Liebermam, "Transgenic mice carrying a PSArasT24 hybrid gene develop salivary gland and gastrointestinal tract neoplasms," *Lab Invest.,* 72:283-290, 1995.

Scheller, Hughes, Golden and Robins, *J. Biol. Chem.,* 273: 24216-24222, 1998.

Scher, Sarkis, Reuter, Cohen, Netto, Patrylak, Lianes, Fuks, Mendelsohn and Cordon-Cardo, "Changing pattern of expression of the epidermal growth factor rectpor and transforming growth factor alpha in the progression of prostatic neoplasms," *Clin. Cancer Res.,* 1:545, 1995.

Schiedner et al., *Nat. Genet.,* 18(2):180-183, 1998.

Schiedner, Morral, Parks, Wu, Koopmans, Langston, Graham, Beaudet and Kochanek, "Genomic DNA transfer with a high-capacity adenovirus vector results in improved in vivo gene expression and decreased toxicity," *Nat. Genet.,* 18:180-183, 1998.

Schuur et al., *J. Biol. Chem.,* 271:7043-7051, 1997.

Schuur, Henderson, Kmetec, Miller, Lamparski and Henderson, "Prostate-specific antigen expression is regulated by an upstream enhancer," *J. Biol. Chem.,* 271:7043-7051, 1996.

Schwab, Chavany, Duroux, Goubin, Lebeau, Helene, Saison-Behmoaras, "Antisense oligonucleotides adsorbed to polyalkylcyanoacrylate nanoparticles specifically inhibit mutated Ha-ras-mediated cell proliferation and tumorigenicity in nude mice," *Proc. Natl. Acad. Sci. USA,* 91(22): 10460-10464, 1994.

Sculier et al., "Pilot study of amphotericin B entrapped in sonicated liposomes in cancer patients with fungal infections," *J. Cancer Clin. Oncol.,* 24(3):527-538, 1988.

Snoek, Rennie, Kasper, Matusik and Bruchovsky, *J. Steroid Biochem. Mol. Biol.,* 59:243-250, 1996.

Spitzweg, Zhang, Bergert, Castro, McIver, Heufelder, Tindall, Young and Morris, "Prostate-specific antigen (PSA) promoter-driven androgen-inducible expression of sodium iodide symporter in prostate cancer cell lines," *Cancer Res.*, 59:2136-2141, 1999.

Starr, Matsui, Thomas and Yamamoto, *Genes Dev.*, 10:1271-1283, 1996.

Steiner, Zhang, Carraher and Lu, "In vivo expression of prostate-specific adenoviral vectors in a canine model," *Cancer Gene Therapy*, 6:456-464, 1999.

Steinwaerder and Lieber, *Gene Ther.*, 7:556-567, 2000.

Stephenson, Dinney, Gohji, Ordonez, Killion and Fidler, "Metastatic model for human prostate cancer using orthotopic implantation in nude mice," *J. Natl. Cancer Inst.*, 84:951, 1992.

Stratford-Perricaudet and Perricaudet, "Gene transfer into animals: the promise of adenovirus," p. 51-61, In: *Human Gene Transfer*, Cohen-Haguenauer and Boiron, Eds., Editions John Libbey Eurotext, France, 1991.

Stratford-Perricaudet et al., "Evaluation of the transfer and expression in mice of an enzyme-encoding gene using a human adenovirus vector," *Hum. Gene Ther.*, 1:241-256, 1990.

Sun, Pan and Balk, *Nucleic Acids Res.*, 25:3318-3325, 1997.

Suzuki, Shin, Fjuikura, Matsuzaki, Takata, "Direct gene transfer into rat liver cells by in vivo electroporation," *FEBS Lett.*, 425(3):436-440, 1998.

Szabo and Sandor, "The diagnostic and prognostic value of tumor angiogenesis," *Eur. J. Surgery Supplement*, 582:99, 1998.

Takakura, "Drug delivery systems in gene therapy," *Nippon Rinsho*, 56(3):691-695, 1998.

Tamanoi and Stillman, "Function of adenovirus terminal protein in the initiation of DNA replication," *PNAS*, 79:2221-2225, 1982.

Tan, "Thesis," University of California, Los Angeles, Molecular Biology Institute, 1999.

Taplin, Bubley, Shuster, Frantz, Spooner, Ogata, Keer and Balk, "Mutation of the androgen-receptor gene in metastatic androgen-independent prostate cancer," *N. Engl. J. Med.*, 332:1393-1398, 1995.

Thalmann, Anezinis, Chang, Zhau, Kim, Hopwood, Pathak, von Eschenbach and Chung, "Androgen-independent cancer progression and bone metastasis in the LNCaP model of human prostrate cancer," *Cancer Res.*, 54:2577, 1994.

Thanos and Maniatis, "Virus induction of human IFN beta gene expression requires the assembly of an enhanceosome," *Cell*, 83:1091-1100, 1995.

Truong-Le, August, Leong, "Controlled gene delivery by DNA-gelatin nanopspheres," *Hum. Gene Ther.*, 9(12):1709-1717, 1998.

Tur-Kaspa et al., "Use of electroporation to introduce biologically active foreign genes into primary rat hepatocytes," *Mol. Cell. Biol.*, 6:716-718, 1986.

Vanbever, Fouchard, Jadoul, De Morre, Preat, Marty, "In vivo noninvasive evaluation of hairless rat skin after high-voltage pulse exposure," *Skin Parmacol. Appl. Skin Physiol.*, 11(1):23-34, 1998.

Verma and Somia, Nature, 389(6648):239-242, 1997.

Wagner, Matteucci, Lewis, Gutierrez, Moulds, Froehler, "Antisense gene inhibition by oligonucleotides containing C-5 propyne pyrimidines," *Science*, 260(5113):1510-1513, 1993.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," *Proc. Natl. Acad. Sci. USA*, 89(13):6099-6103, 1992.

Warriar, Page, Koutsilieris and Govindan, *J. Steroid Biochem. Mol. Biol.*, 46:699-711, 1993.

Wei, Willis, Tilton, Looney, Lord, Barth and Frelinger, "Tissue-specific expression of the human prostate-specific antigen gene in transgenic mice: implications for tolerance and immunotherapy," *Proc. Natl. Acad. Sci. USA*, 94:6369-6374, 1997.

Weintraub, Davis, Lockshon and Lassar, "MyoD binds cooperatively to two sites in a target enhancer sequence: occupancy of two sites is required for activation," *Proc. Natl. Acad. Sci. USA*, 87:5623-5627, 1990.

Wheeler et al., *Proc. Natl. Acad. Sci. USA*, 93:11454-11459, 1996.

Wong and Neumann, "Electric field mediated gene transfer," *Biochim. Biophys. Res. Commun.*, 107(2):584-587, 1982.

Wong et al., "Appearance of β-lactamase activity in animal cells upon liposome mediated gene transfer," *Gene*, 10:87-94, 1980.

Wong, Zhou, Sar and Wilson, *J. Biol. Chem.*, 268:19004-19012, 1993.

Wu and Wu, "Evidence for targeted gene delivery to HepG2 hepatoma cells in vitro," *Biochemistry*, 27:887-892, 1988.

Wu and Wu, "Receptor-mediated in vitro gene transfections by a soluble DNA carrier system," *J. Biol. Chem.*, 262:4429-4432, 1987.

Wu and Wu, *Adv. Drug Delivery Rev.*, 12:159-167, 1993.

Wu, Hsieh, Gleave, Brown, Pathak and Chung, "Derivation of androgen-independent human LNCaP prostatic cancer cellsublines: role of bone stromal cells," *Int. J. Cancer*, 57:406-412, 1994.

Yang et al., "In vivo and in vitro gene transfer to mammalian somatic cells by particle bombardment," *Proc. Natl. Acad. Sci. USA*, 87:9568-9572, 1990.

Yang, Jiang, Sun, Hasegawa, Baranov, Chishima, Shimada, Moosa and Hoffman, "A fluorescent orthotopic bone metastasis model of human prostate cancer," *Cancer Res.*, 59:791, 1999.

Yeh and Chang, *Proc. Natl. Acad. Sci. USA*, 93:5517-5521, 1996.

Young, Andrews, Montgomery and Tindall, "Tissue-specific and hormonal regulation of human prostate-specific glandular kallikrein," *Biochemistry*, 31:818-824, 1992.

Young, Qiu, Prescott and Tindall, "Overexpression of a partial human androgen receptor in *E. coli*: characterization of steroid binding, DNA binding, and immunological properties," *Mol. Endocrinology*, 4:1841-1849, 1990.

Zambaux, Bonneaux, Gref, Maincent, Dellacherie, Alonso, Labrude, Vigneron, "Influence of experimental paparmeters on the characteristics of poly(lactic acid) nanoparticles prepared by a double emulsion method," *J. Controlled Release*, 50(1-3):31-40, 1998.

Zelenin et al., "High-velocity mechanical DNA transfer of the chloramphenicol acetyltransferase gene into rodent liver, kidney and mammary gland cells in organ explants and in vivo," *FEBS Lett.*, 280:94-96, 1991.

Zhang, Murtha and Young, *Biochem. Biophys. Res. Commun.*, 231:784-788, 1997a.

Zhang, Zhang, Murtha, Zhu, Hou and Young, "Identification of two novel cis-elements in the promoter of the prostate-specific antigen gene that are required to enhance androgen receptor-mediated transactivation," *Nucleic Acids Res.*, 25:3143-150, 1997b.

Zhau, Li and Chung, *Cancer*, 88:2995-3001, 2000.

Zou et al., *Mol. Ther.*, 2:105-113, 2000.

zur Muhlen, Schwarz, Mehnert, "Solid lipid nanoparticles (SLN) for controlled drug delivery—drug release and release mechanism," *Eur. J. Pharm. Biopharm.*, 45(2): 149-155, 1998.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An isolated polynucleotide comprising:

a prostate specific enhancer sequence having at least four androgen response elements in tandem wherein each of said elements independently has the sequence of SEQ ID NO:1, SEQ ID NO:2, SEQ ID NO:3, or SEQ ID NO:4;

at least the sequence of one prostate specific promoter; and a nucleic acid sequence that encodes a heterologous polypeptide, wherein said enhancer sequence and said promoter sequence are operably linked to the nucleic acid sequence that encodes the heterologous polypeptide.

2. The isolated polynucleotide of claim 1, wherein said enhancer sequence comprises the sequence of SEQ ID NO:3.

3. The isolated polynucleotide of claim 2, wherein said enhancer sequence comprises no more than 4 androgen response elements.

4. The isolated polynucleotide of claim 1, wherein said promoter is a prostate specific antigen promoter or a human kallekrein 2 proximal promoter.

5. The isolated polynucleotide of claim 1, wherein said at least four androgen response elements are positioned within said enhancer sequence as direct tandem repeats.

6. The isolated polynucleotide of claim 1, wherein said at least four androgen response elements are positioned within said enhancer sequence in inverted tandem fashion.

7. The isolated polynucleotide of claim 1, wherein at least a first one and a second one of said at least 4 androgen response elements are positioned within said enhancer sequence as direct tandem repeats, and at least a third one of said at least 4 androgen response elements is positioned within said enhancer sequence in an inverted orientation relative to said first one and said second one of said androgen response elements.

8. The isolated polynucleotide of claim 1, wherein at least a first one and a second one of said at least 4 androgen response elements are positioned within said enhancer sequence as direct tandem repeats, and at least a third one and a fourth one of said at least 4 androgen response elements are positioned within said enhancer sequence in an inverted orientation relative to said first one and said second one of said androgen response elements.

9. The isolated polynucleotide of claim 1, wherein at least one of said isolated-androgen response elements comprises the sequence of SEQ ID NO:1 or SEQ ID NO:2.

10. The isolated polynucleotide of claim 1, wherein at least one of said isolated androgen response elements comprises the sequence of SEQ ID NO:4.

11. The isolated polynucleotide, of claim 1, wherein said enhancer sequence comprises the sequence of SEQ ID NO: 5.

12. The isolated polynucleotide of claim 1, further comprising the sequence of any one of SEQ ID NO:62, SEQ ID NO:63, or SEQ ID NO:64.

13. The isolated polynucleotide of claim 1, wherein each of said androgen response elements consists of from 15 to about 35 nucleotides.

14. The isolated polynucleotide of claim 13, wherein each of said androgen response elements consists of from 15 to about 25 nucleotides.

15. The isolated polynucleotide of claim 14, wherein each of said androgen response elements consists of from 15 to about 20 nucleotides.

16. The isolated polynucleotide of claim 15, wherein each of said androgen response elements consists of from 15 to about 18 nucleotides.

17. The isolated polynucleotide of claim 1, wherein said promoter is a PSA promoter.

18. The isolated polynucleotide of claim 1, wherein each of said at least 4 androgen response elements is separated from the other androgen response elements in said enhancer sequence by an intervening sequence of from 1 to about 20 nucleotides.

19. The isolated polynucleotide of claim 18, wherein each of said at least 4 androgen response elements is separated from the other androgen response elements in said enhancer sequence by an intervening sequence of from about 5 to about 15 nucleotides.

20. The isolated polynucleotide of claim 19, wherein each of said at least 4 androgen response elements is separated from the other androgen response elements in said enhancer sequence by an intervening sequence of from about 8 to about 12 nucleotides.

21. The isolated polynucleotide of claim 1, wherein said enhancer is separated from the promoter sequence by an intervening sequence of from 1 to about 39 nucleotides.

22. The isolated polynucleotide of claim 21, wherein said intervening sequence is from about 5 to about 30 nucleotides.

23. The isolated polynucleotide of claim 22, wherein said intervening sequence is from 10 to about 20 nucleotides.

24. The isolated polynucleotide, of claim 1, wherein said promoter is a proximal promoter comprising a sequence of from about 50 to about 1000 nucleotides in length.

25. The isolated polynucleotide of claim 24, wherein said proximal promoter comprises a sequence of from 100 to about 500 nucleotides; in length.

26. The isolated polynucleotide of claim 25, wherein said proximal promoter comprises a sequence or from 200 to about 400 nucleotides in length.

27. The isolated polynucleotide of claim 1, wherein said enhancer sequence comprises the sequence of SEQ ID NO:65.

28. The isolated polynucleotide of claim 1, further comprising the sequence of a prostate specific antigen (PSA) enhancer or a human kallekrein 2 enhancer.

29. The isolated polynucleotide of claim 27, wherein said-enhancer sequence comprises the sequence of SEQ ID NO:5.

30. A vector comprising the polynucleotide of claim 1.

31. The vector of claim 30, wherein said vector is a plasmid.

32. The vector of claim 31, wherein said plasmid is an expression vector or a transcription vector.

33. A viral vector capable of transfecting mammalian cells, wherein the vector comprises the polynucleotide of claim 1.

34. The viral vector of claim 33, wherein said vector is a retroviral, adenoviral, adeno-associated viral, or herpes viral vector.

35. The viral vector of claim 34, wherein said vector is a gutless adenoviral vector or a recombinant adeno-associated viral vector.

36. An in vitro host cell comprising the polynucleotide of claim 1.

37. The host cell of claim 36, wherein said host cell is a mammalian host cell.

38. The host cell of claim 37, wherein said mammalian host cell is a human host cell.

39. The host cell of claim 38, wherein said human host cell is a prostate cell.

40. The host cell of claim 39, wherein said human host cell is a prostate epithelial, tumor or carcinoma cell.

41. A composition comprising the isolated polynucleotide of claim 1.

42. The composition of claim 41, further comprising a pharmaceutical excipient.

43. The composition of claim 42, further comprising a lipid, a liposome, a lipofection complex, a nanoparticle, or a nanocapsule.

44. The composition of claim 42, wherein said pharmaceutical excipient is formulated for administration to a human.

45. An in vitro non-human mammalian host cell containing the polynucleotide of claim 1.

46. The isolated polynucleotide of claim 1, wherein at least four of the androgen response elements are capable of engaging in a cooperative and synergistic binding of an androgen receptor.

47. The polynucleotide of claim 1 further comprising a native PSA core enhancer operably positioned in relation to the prostate specific enhancer sequence.

48. The isolated polynucleotide of claim 1, wherein the enhancer consists of a polynucleotide of the formula 5'-$N_{x1}$-$ARE_1$-$N_{x2}$-$ARE_2$-$N_{x2}$-$ARE_3$-$N_{x2}$-$ARE_4$-$N_{x3}$-3', wherein:
   each N is a nucleotide independently selected from C, A, T, or G;
   x1 is an integer from 1 to 39;
   each x2 is independently an integer from 1 to 20;
   x3 is independently an integer from 1 to 39; and
   ARE1, ARE2, ARE3, and ARE4 are each an androgen response element independently having the sequence of SEQ ID NO:1, SEQ ID NO:2, SEQ ID NO:3, or SEQ ID NO:4.

49. The isolated polynucleotide of claim 1, wherein the heterologous polypeptide is TRAIL, diphtheria toxin A-chain, ricin A chain, cytosine deaminase, thymidine kinase, sodium iodide symporter, thymidine kinase SR39, *Pseudomonas* exotoxin, C-CAM1, PTEN, E-cadherin, p16, p53, pHyde, PML, IL-1, IL-2, IL-12, GM-CSF, IFNa, IFNβ, or IFNγ.

50. The isolated polynucleotide of claim 1, wherein the heterologous polypeptide is a cytotoxin, a transcription factor, an apoptotic factor, a tumor suppressor, a kinase, a cytokine, a lymphokine, or a protease.

51. A gene expression enhancer, said enhancer comprising at least four androgen response elements wherein each of said elements independently has the sequence of SEQ ID NO:1, SEQ ID NO:2, SEQ ID NO:3, or SEQ ID NO:4, with the proviso that at least one of the elements has the sequence of SEQ ID NO:1.

52. The enhancer of claim 51, wherein the enhancer consists of a polynucleotide of the formula 5'-$N_{x1}$-$ARE_1$-$N_{x2}$-$ARE_2$-$N_{x2}$-$ARE_3$-$N_{x2}$-$ARE_4$-$N_{x3}$-3', wherein:

each N is a nucleotide independently selected from C, A, T, or G;
x1 is an integer from 1 to 39;
each x2 is independently an integer from 1 to 20;
x3 is independently an integer from 1 to 39; and
ARE1, ARE2, ARE3, and ARE4 are each an androgen response element independently having the sequence of SEQ ID NO:1, SEQ ID NO:2, SEQ ID NO:3, or SEQ ID NO:4, with the proviso that at least one of the elements has the sequence of SEQ ID NO:1.

53. An isolated polynucleotide comprising:

an prostate specific enhancer sequence having at least four androgen response elements in tandem wherein each of said elements independently has the sequence of SEQ ID NO:1, SEQ ID NO:2, SEQ ID NO:3, or SEQ ID NO:4;

at least the sequence of one prostate specific promoter; and a nucleic acid sequence that encodes a heterologous polypeptide, wherein said enhancer sequence and said promoter sequence are operably linked to the nucleic acid sequence that encodes the heterologous polypeptide; with the proviso that at least one of the androgen response elements has the sequence of SEQ ID NO:1.

* * * * *

UNITED STATES PATENT AND TRADEMARK OFFICE
CERTIFICATE OF CORRECTION

PATENT NO. : 7,267,978 B1
APPLICATION NO. : 10/110681
DATED : September 11, 2007
INVENTOR(S) : Michael F. Carey, Arie S. Belldegrun and Lily Wu It is certified that error appears in the above-identified patent and that said Letters Patent is hereby corrected as shown below:

Title page of the issued patent:

(75) Inventors:
Michael F. Carey, Sherman Oaks, CA (US); Arie S. Belldegrun, Los Angeles, CA (US); Lilly Wu, Northridge, CA (US)

should read:

Item (75) Inventors:
Michael F. Carey, Sherman Oaks, CA (US); Arie S. Belldegrun, Los Angles, CA (US); Lily Wu, Northridge, CA (US)

Signed and Sealed this

Sixth Day of May, 2008

JON W. DUDAS
*Director of the United States Patent and Trademark Office*

SEQUENCE LISTING

```
<160> NUMBER OF SEQ ID NOS: 67

<210> SEQ ID NO 1
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 1
agaacagcaa gtgct                                                     15

<210> SEQ ID NO 2
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 2
agaacagcaa gtact                                                     15

<210> SEQ ID NO 3
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 3
ggaacatatt gtatt                                                     15

<210> SEQ ID NO 4
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 4
ggaacatatt gtatc                                                     15

<210> SEQ ID NO 5
<211> LENGTH: 157
<212> TYPE: DNA
```

```
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 5
ccatggtaac cgggatcct ctagaactag tggatctgca gaacagcaag tgctagctga      60
tcagctagca cttgctgttc tgcaagatca gctagcactt gctgttctgc aagctcagct    120
agcacttgct gttctgcaag atcccccggg cccatgg                              157

<210> SEQ ID NO 6
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE
<220> FEATURE:
<221> NAME/KEY: misc_feature
<222> LOCATION: (7)..(9)
<223> OTHER INFORMATION: N = C, G, A, or T

<400> SEQUENCE: 6
ggwacannnt gttct                                                      15

<210> SEQ ID NO 7
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 7
ggaagatatt gtatc                                                      15

<210> SEQ ID NO 8
<211> LENGTH: 16
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 8
ggaacatatt gttatt                                                     16

<210> SEQ ID NO 9
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 9
ggatgctgtg cagaa                                                      15

<210> SEQ ID NO 10
<211> LENGTH: 15
<212> TYPE: DNA
<213> ORGANISM: Artificial Sequence
```

```
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 10
ggatgctgtg cacac                                                          15

<210> SEQ ID NO 11
<211> LENGTH: 41
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 11
ctgcagcgga gtactgtcct ccggtttgtg ccactggtga g                             41

<210> SEQ ID NO 12
<211> LENGTH: 41
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 12
cggaggacag tactccgctg caggactgct ctggtcaccc t                             41

<210> SEQ ID NO 13
<211> LENGTH: 39
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 13
gtcgacggag tactgtcctc cgcctgctca gcctttgtc                                39

<210> SEQ ID NO 14
<211> LENGTH: 40
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 14
cggaggacag tactccgtcg acgattgagg attcctaatc                               40

<210> SEQ ID NO 15
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 15
actgttcaaa cttgcaaacc tgc                                                 23
```

```
<210> SEQ ID NO 16
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 16
gcaggtttgc aagtttgaac agt                                              23

<210> SEQ ID NO 17
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 17
actgggacgg actgcaaacc tgc                                              23

<210> SEQ ID NO 18
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 18
gcaggtttgc agtccgtccc agt                                              23

<210> SEQ ID NO 19
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 19
actgggacaa cttgcgggac tgc                                              23

<210> SEQ ID NO 20
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 20
gcagtcccgc aagttgtccc agt                                              23

<210> SEQ ID NO 21
<211> LENGTH: 51
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE
```

<400> SEQUENCE: 21
gtcgacgtcg accggagtac tgtcctccgt cgacgaaaac agacctactc t    51

<210> SEQ ID NO 22
<211> LENGTH: 51
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 22
gtcgacggag gacagtactc cggtcgacgt cgacgacaaa ggctgagcag g    51

<210> SEQ ID NO 23
<211> LENGTH: 36
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 23
cggagtactg tcctccgatt gtccttgaca gtaaac    36

<210> SEQ ID NO 24
<211> LENGTH: 36
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 24
cggaggacag tactccgcca gagtaggtct gttttc    36

<210> SEQ ID NO 25
<211> LENGTH: 41
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 25
ctgcagcgga gtactgtcct ccgctgagag agatatcatc t    41

<210> SEQ ID NO 26
<211> LENGTH: 41
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 26
cggaggacag tactccgctg caggataata aagataatgt c    41

<210> SEQ ID NO 27
<211> LENGTH: 41
<212> TYPE: DNA

```
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 27
ctgcagcgga gtactgtcct ccgacgtgac agaaccatgg a                    41

<210> SEQ ID NO 28
<211> LENGTH: 41
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 28
cggaggacag tactccgctg cagacagcaa cacctttttt t                    41

<210> SEQ ID NO 29
<211> LENGTH: 59
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 29
gctctagacc accatggact acaaggacga cgacgacaag gccgaagtgc agttagggc    59

<210> SEQ ID NO 30
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 30
ccctctagac ggccgagggt agaccct                                     27

<210> SEQ ID NO 31
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 31
tttccttgca gtacagcatg ttctagc                                     27

<210> SEQ ID NO 32
<211> LENGTH: 18
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 32
agaagcagga tgtgatag                                               18
```

<210> SEQ ID NO 33
<211> LENGTH: 11
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 33
ccctcgagcg c                                                          11

<210> SEQ ID NO 34
<211> LENGTH: 39
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 34
ggttaggcat aaccctcgag cgcaagaagt atttaatgg                            39

<210> SEQ ID NO 35
<211> LENGTH: 18
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 35
agctgcccac atttaaat                                                   18

<210> SEQ ID NO 36
<211> LENGTH: 22
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 36
caactccatc atgaagtgtg ac                                              22

<210> SEQ ID NO 37
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 37
ctcgcgttca tgaggcacac c                                               21

<210> SEQ ID NO 38
<211> LENGTH: 22
<212> TYPE: DNA
<213> ORGANISM: Artificial Sequence
<220> FEATURE:
<221> NAME/KEY: misc_feature
<222> LOCATION: ()..()

-continued

<223> OTHER INFORMATION: SYNTHETIC OLIGONUCLEOTIDE

<400> SEQUENCE: 38
tgtctcggat cctgggaggc tg                                         22

<210> SEQ ID NO 39
<211> LENGTH: 18
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 39
ctcaggaatt cgccacga                                              18

<210> SEQ ID NO 40
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 40
caagctcctg gactcctggc a                                          21

<210> SEQ ID NO 41
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 41
tagatgggct tgactttccc                                            20

<210> SEQ ID NO 42
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 42
cttcttgcag cgatacagct c                                          21

<210> SEQ ID NO 43
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 43
atgctccaat aaattcactg c                                          21

<210> SEQ ID NO 44
<211> LENGTH: 19

```
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 44
atgcggatca aacctcacc                                            19

<210> SEQ ID NO 45
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 45
atctggttcc cgaaaccctg                                           20

<210> SEQ ID NO 46
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 46
cccaagcggc tgtactgcaa                                           20

<210> SEQ ID NO 47
<211> LENGTH: 19
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 47
agctcttagc agacattgg                                            19

<210> SEQ ID NO 48
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 48
gacttccgca aggacctcgg c                                         21

<210> SEQ ID NO 49
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 49
```
gcgcacgatc atgttggaca g                                              21

<210> SEQ ID NO 50
<211> LENGTH: 24
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 50
cctgtctacc tgcagcacac tcga                                           24

<210> SEQ ID NO 51
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 51
ggcggcatgt ctattttgta aacctcc                                        27

<210> SEQ ID NO 52
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 52
atgtagccgc cccacacaga                                                20

<210> SEQ ID NO 53
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 53
catccatctt tttcagccat                                                20

<210> SEQ ID NO 54
<211> LENGTH: 24
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 54
ctttgagttc ggtggggtca tgtg                                           24

<210> SEQ ID NO 55
<211> LENGTH: 24
<212> TYPE: DNA
<213> ORGANISM: Artificial Sequence
<220> FEATURE:
<221> NAME/KEY: misc_feature

```
<222> LOCATION: ()..()
<223> OTHER INFORMATION: SYNTHETIC OLIGONUCLEOTIDE

<400> SEQUENCE: 55
tgacttcact tgtggcccag atag                                              24

<210> SEQ ID NO 56
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 56
ctgaagtgac tcgtaacgac                                                   20

<210> SEQ ID NO 57
<211> LENGTH: 22
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 57
catgtctgcc agcttcttga ag                                                22

<210> SEQ ID NO 58
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 58
tggtacagtc agagccaacc                                                   20

<210> SEQ ID NO 59
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 59
agcagtcaca gcacatgacg                                                   20

<210> SEQ ID NO 60
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 60
ggacgaactg gtgtaatgat atg                                               23

<210> SEQ ID NO 61
```

```
<211> LENGTH: 24
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 61
tctactgttt ttgtgaagta cagc                                            24

<210> SEQ ID NO 62
<211> LENGTH: 392
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 62
ggtgaccaga gcagtctagg tggatgctgt gcacacgggg tttgtgccac tggtgagaaa     60
cctgagatta ggaatcctca atcttatact gggacaactt gcaaacctgc tcagcctttg    120
tctctgatga agatattatc ttcatgatct tggattgaaa acagacctac tctggaggaa    180
catattgtat tgattgtcct tgacagtaaa caaatctgtt gtaagagaca ttatctttat    240
tatctaggac agtaagcaag cctggatctg agagagatat catcttgcaa ggatgcctgc    300
tttacaaaca tccttgaaac aacaatccag aaaaaaagtg ttgctgtctt tgctcagaag    360
acacacagat acgtgacaga accatggtaa cc                                  392

<210> SEQ ID NO 63
<211> LENGTH: 390
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 63
ggtgaccaga gcagtctagg tggatgctgt gcagaagggg tttgtgccac tggtgagaaa     60
cctgagatta ggaatcctca atcttatact gggacaactt gcaaacctgc tcagcctttg    120
tctctgatga agatattatc ttcatgatct tggattgaaa acagacctac tctggaggaa    180
catattgtat cgattgtcct tgacagtaaa caaatctgtt gtaagagaca ttatctttat    240
tatctaggac agtaagcaag cctggatctg agagagatat catcttgcaa ggatgcctgc    300
tttacaaaca tccttgaaac aacaatccag aaaaaaaag tgttgctgt ctttgctcag     360 aagacacaca gatacgtgac agaaccatgg                                     390

<210> SEQ ID NO 64
<211> LENGTH: 203
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 64
ctttgtatct gacggagata ttatctttat aatgggttga aagcagacct actctggagg     60
aacatattgt atttattgtc ctgaacagta aacaaatctg ctgtaaaata gacgttaact    120
```

```
ttattatcta aggcagtaag caaacctaga tctgaaggcg ataccatctt gcaaggctat      180
ctgctgtaca aatatgcttg aaa                                              203

<210> SEQ ID NO 65
<211> LENGTH: 65
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE
<220> FEATURE:
<221> NAME/KEY: misc_feature
<222> LOCATION: (1)..(65)
<223> OTHER INFORMATION: N = C, G, A, or T; First N can be from 1 to 39
      nucleotides,
<220> FEATURE:
<221> NAME/KEY: misc_feature
<222> LOCATION: (1)..(65)
<223> OTHER INFORMATION: second N can be from 1 to 20 nucleotides,
<220> FEATURE:
<221> NAME/KEY: misc_feature
<222> LOCATION: (1)..(65)
<223> OTHER INFORMATION: third N can be from 1 to 20 nucleotides,
<220> FEATURE:
<221> NAME/KEY: misc_feature
<222> LOCATION: (1)..(65)
<223> OTHER INFORMATION: fourth N can be from 1 to 20 nucleotides,
<220> FEATURE:
<221> NAME/KEY: misc_feature
<222> LOCATION: (1)..(65)
<223> OTHER INFORMATION: last N can be from 1 to 39 nucleotides.

<400> SEQUENCE: 65
nagaacagca agtgctnaga acagcaagtg ctnagaacag caagtgctna gaacagcaag      60 tgctn                                                                  65

<210> SEQ ID NO 66
<211> LENGTH: 49
<212> TYPE: DNA
<213> ORGANISM: Artificial Sequence
<220> FEATURE:
<221> NAME/KEY: misc_feature
<222> LOCATION: ()..()
<223> OTHER INFORMATION: SYNTHETIC OLIGONUCLEOTIDE
<220> FEATURE:
<221> NAME/KEY: misc_feature
<222> LOCATION: (1)..(49)
<223> OTHER INFORMATION: N = C, G, A, or T; First N can be from 1 to 39
      nucleotides,
<220> FEATURE:
<221> NAME/KEY: misc_feature
<222> LOCATION: (1)..(49)
<223> OTHER INFORMATION: second N can be from 1 to 20 nucleotides,
<220> FEATURE:
<221> NAME/KEY: misc_feature
<222> LOCATION: (1)..(49)
<223> OTHER INFORMATION: third N can be from 1 to 20 nucleotides,
<220> FEATURE:
<221> NAME/KEY: misc_feature
<222> LOCATION: (1)..(49)
<223> OTHER INFORMATION: last N can be from 1 to 39 nucleotides.

<400> SEQUENCE: 66
nagaacagca agtgctnaga acagcaagtg ctnagaacag caagtgctn                  49

<210> SEQ ID NO 67
<211> LENGTH: 81
<212> TYPE: DNA
<213> ORGANISM: Artificial Sequence
<220> FEATURE:
```

```
<221> NAME/KEY: misc_feature
<222> LOCATION: ()..()
<223> OTHER INFORMATION: SYNTHETIC OLIGONUCLEOTIDE
<220> FEATURE:
<221> NAME/KEY: misc_feature
<222> LOCATION: (1)..(81)
<223> OTHER INFORMATION: N = C, G, A, or T; First N can be from 1 to 39
      nucleotides,
<220> FEATURE:
<221> NAME/KEY: misc_feature
<222> LOCATION: (1)..(81)
<223> OTHER INFORMATION: second N can be from 1 to 20 nucleotides,
<220> FEATURE:
<221> NAME/KEY: misc_feature
<222> LOCATION: (1)..(81)
<223> OTHER INFORMATION: third N can be from 1 to 20 nucleotides,
<220> FEATURE:
<221> NAME/KEY: misc_feature
<222> LOCATION: (1)..(81)
<223> OTHER INFORMATION: fourth N can be from 1 to 20 nucleotides,
<220> FEATURE:
<221> NAME/KEY: misc_feature
<222> LOCATION: (1)..(81)
<223> OTHER INFORMATION: fifth N can be from 1 to 20 nucleotides,
<220> FEATURE:
<221> NAME/KEY: misc_feature
<222> LOCATION: (1)..(81)
<223> OTHER INFORMATION: last N can be from 1 to 39 nucleotides.

<400> SEQUENCE: 67
nagaacagca agtgctnaga acagcaagtg ctnagaacag caagtgctna gaacagcaag      60
tgctnagaac agcaagtgct n                                               81
```